United States Patent [19]

Thiele et al.

[11] Patent Number: 5,602,102

[45] Date of Patent: Feb. 11, 1997

[54] DIPEPTIDYL PEPTIDASE-I INHIBITORS AND USES THEREOF

[75] Inventors: Dwain L. Thiele, Coppell; Peter E. Lipsky, Dallas; Michael J. McGuire, Irving, all of Tex.

[73] Assignee: Board of Regents, The Univ. of TX System, Austin, Tex.

[21] Appl. No.: 890,422

[22] Filed: May 29, 1992

[51] Int. Cl.$^6$ .................................................. A61K 38/05
[52] U.S. Cl. ............................. 514/19; 562/575; 562/445
[58] Field of Search ........................... 514/19; 424/94.65; 562/575, 445

[56] References Cited

U.S. PATENT DOCUMENTS

| | | | |
|---|---|---|---|
| 4,752,602 | 6/1988 | Lipsky et al. | 514/19 |
| 5,047,401 | 9/1991 | Lipsky et al. | 514/19 |
| 5,068,223 | 11/1991 | Lipsky et al. | 514/19 |
| 5,223,486 | 6/1993 | Gordon | 514/18 |
| 5,403,919 | 4/1995 | Butcher | 530/388.22 |

FOREIGN PATENT DOCUMENTS

PCT/US93/
05093  10/1993  WIPO .......................... C12N 15/57

OTHER PUBLICATIONS

Thiele, D. L., and P. E. Lipsky (1990), The action of leucyl–leucine methyl ester on cytotoxic lymphocytes requires uptake by a novel dipeptide–specific facilitated transport system and dipeptidyl peptidase I–mediated conversion to membranolytic products, *J. Exp. Med.*, 172:183–194, published in USA.

Salvesen, G., and J. J. Enghild (1990), An unusual specificity in the activation of neutrophil serine proteinase zymogens, *Biochemistry*, 29:5304, published in USA.

Vanderslice, P., C. S. Craik, J. A. Nadel, and G. H. Caughey (1989), Molecular cloning of dog mast cell tryptase and a related protease: structural evidence of a unique mode of serine protease activation, *Biochemistry*, 28:4148, published in USA.

Reynolds, D. S., R. L. Stevens, W. S. Lane, M. H. Carr, K. F. Austen, and W. Serafin (1990), Different mouse mast cell populations express various combinations of at least six distinct mast cell serine proteases, *Proc. Natl. Acad. Sci. USA* 87:3230, published in USA.

Shaw, E., and G. D. J. Green (1981), Inactivation of thiol proteases with peptidyl diazomethyl ketones in Methods in Enzymology edited by S. P. Colowick and L. Lorand, 80:820, Academic Press, New York, published in USA.

Green, G. D. J., and E. Shaw (1981), Peptidyl diazomethyl ketones are specific inactivators of thiol proteinases, *J. Biol. Chem.*, 256:1923, published in USA.

Shaw, E. (1990) Cysteinyl proteinases and their selective inactivation in Advances in enzymology and related areas of molecular biology edited by A. Meister, 63:271, Interscience Publications, J. Wiley and Sons, New York, published in USA.

McDonald, J. K., P. X. Callahan, B. B. Zeitman, and S. Ellis (1969) Inactivation and degradation of glucagon by dipeptidyl aminopeptidase I (cathepsin C) of rat liver including a comparative study of secretin degradation, *J. Biol. Chem.*, 244:6199, published in USA.

Raff, R. F., E. Severns, R. Storb, P. Martin, T. Graham, B. Sandmaier, F. Schuening, G. Sale, and F. R. Appelbaum (1988), L–Leucyl–l–leucine methyl ester treatment of canine marrow and peripheral blood cells, *Transplantation*, 46:655, published in USA.

McDonald, J. K., B. B. Zeitman, T. J. Reilly, and S. Ellis (1969), New observations on the substrate specificity of cathepsin C (dipeptidyl aminopeptidase I), *J. Biol. Chem.*, 244:2693, published in USA.

Thiele, D. L., Charley, M. R., Calomeni, J. A. and Lipsky, P. E., Lethal graft–vs–host disease across major histocompatibility barriers: Requirement for leucyl–leucine methyl ester sensitive cytotoxic T cells, *J. Immunol* 138:51–57, 1987, published in USA.

Thiele, S. L., Calomeni, J. A. and Lipsky, P. E., Leucyl–Leucine methyl ester treatment of donor cells permits establishment of immunocompetent parent→F1 chimeras that are selectively tolerant of host alloantigens, *J. Immunol.*, 139:2137–2137–2142, 1987, published in USA.

Blazar, B. R., Thiel, D. L. and Vallera, D. A., Pretreatment of murine donor grafts with L–leucyl–L–leucine methyl ester: Elimination of graft–versus–host disease without detrimental effects on engraftment, *Blood,* 75:798–805, 1990, published in USA.

McGuire, M. J., Lipsky, P. E., and Thiele, D. L., Purification and characterization of human dipeptidyl peptidase I (DPPI). *FASEB J*, 5:A827, 1991, published in Europe.

Thiele, D. L. and Lipsky, P. E., Apoptosis is an essential step in leucyl–leucine methyl ester (Leu–Leu–OMe) mediated killing of cytotoxic lymphocytes and myeloid cells, *FASEB J*, 5:A973, 1991, published in Europe.

Thompson, S. A., P. R. Andrews, and R. P. Hanzlik (1986), Carboxyl–modified amino acids and peptides as protease inhibitors, *J. Med. Chem.*, 29:104–111, published in USA.

(List continued on next page.)

*Primary Examiner*—Elizabeth C. Weimar
*Assistant Examiner*—David Lukton
*Attorney, Agent, or Firm*—Denise L. Mayfield

[57] ABSTRACT

Therapeutic agents and methods for the treatment of immunologically mediated diseases and malignancies of myeloid cell or lymphoid cell origin. These particular methods utilize the characterization of particular activation mechanisms important to the progression of these pathologies in humans. Selective inhibition of cell types responsible for precipitating these disorders in humans are provided with therapeutic agents which include peptides capable of inhibiting dipeptidyl peptidase-I activation of proenzymes present primarily in cytotoxic T-cells and myeloid cells, such as Gly—Phe—$CHN_2$. Antisense oligonucleotides are also characterized which are specific for human dipeptidyl peptidase-I gene which may be used in the treatment of the described disorders.

7 Claims, 20 Drawing Sheets

OTHER PUBLICATIONS

Thiele, D. L. and P. E. Lipsky (1985), Modulation of Human natural killer cell function by L-leucine methyl ester: monocyte-dependent depletion from human peripheral blood mononuclear cells, *J. Immunol.*, 134:786-793, published in USA.

Senior, R. M., E. J. Campbell, (1984), Cathepsin G in human mononuclear phagocytes: comparisons between monocytes and U937 moncyte-like cells, *J. Immunol.*, 132:2547-2551, published in USA.

Angliker, H., P. Wikstrom, H. Kirschke and E. Shaw (1989), The inactivation of the cysteinyl exopeptidases cathepsin H and C by affinity-labelling reagents, *Biochem. J.*, 262:63-68, published in Great Britain.

Lathe, R., (1985), Synthetic oligonucleotide probes deduced from amino acid sequence data theoretical and practical considerations, *J. Mol. Biol.*, 183:1-12, published in Europe.

Ishidoh, K. D. Muno, N. Sato and E. Kominami (1991), Molecular Cloning of cDNA for rat cathepsin D, *J. Biol. chem.*, 256(25):16312-16317, Sep. 5, 1991, published in USA.

Enzyme System Products, 6497 Sierra Lane, Dublin, CA 9468, published in USA.

McGuire, Michael J., Lipsky, Peter E., and Thiele, Dwain L., Purification and characterization of dipeptidyl peptidase I[1] from human spleen, *Archives of Biochem. Biophys.*, 295(2):001-009, 1992, published in USA.

Dialog searches produced in USA.

McGuire et al., "Purification and Characterization of Human Dipeptidyl Peptidase I (DPPI)," *The Faseb Journal*, Part I: Abstracts of the 75th Annual Meeting, Atlanta, Georgia, Apr. 21-25, 1991, Abstract No. 2655.

Thiele and Lipsky, "Mechanism of L-Leucyl-L-Leucine Methyl Ester-Mediated Killing of Cytotoxic Lymphocytes: Dependence on a Lysosomal Thiol Protease, Dipeptidyl Peptidase I, That is Enriched in These Cells," *Proc. Natl. Acad. Sci. USA*, 87(1):83-87, 1990.

Falanga et al., "Inhibition of Cancer Procoagulant by Peptidyl Diazomethyl Ketones and Peptidyl Sulfonium Salts," *Thrombosis Research*, 54:389-398, 1989.

Green and Shaw, "Peptidyl Diazomethyl Ketones Are Specific Inactivators of Thiol Proteinases," *J. Biol. chem.*, 256(4):1923-1928, 1981.

Imperiali and Abeles, "Inhibition of Serine Proteases by Peptidyl Fluoromethyl Ketones," *Biochemistry*, 25:3760-3767, 1986.

Ishidoh et al., "Molecular Cloning of cDNA for Rat Cathepsin C," *J. Biol. Chem.*, 266(25):16312-16317, 1991.

McGuire et al., "Purification and Characterization of Dipeptidyl Peptidase I from Human Spleen," *Arch. Biochem. Biophys.*, 295(2):280-288, 1992.

McGuire et al., "Generation of Active Myeloid and Lymphoid Granule Serine Proteases Requires Processing by the Granule Thiol Protease Dipeptidyl Peptidase I," *J. Biol. Chem.*, 268(4):2458-2467, 1993.

Randell Inflammation 12, 67, 1988.

Crawford Biochem J 253, 751, 1988.

| H | XLPTSXDVRNV | HGINFVSPVR | NQASCGSCYS | FASMGMLEAR | IRILTXNSQT |
|---|---|---|---|---|---|
| R | LPESWDWRNV | RGINFVSPVR | NQESCSGCYS | FASLGMLEAR | IRILTNNSQT |
| H | PILSPQEVVS | ......... | .......Y | AQDFGLVEEA | SFPYTXXD-- |
| R | PILSPQEVVS | CSPYAQGCDG | GFPYLIAGKY | AQDFGVVEEN | CFPYTATDAP |
| H | ......Y | YSSEYHYVGG | FYGGMNEALM | KLELVRHGPM | AVAFEYVYDF |
| R | CKPKENCLRY | YSSEYYYVGG | FYGGCNEALM | KLELVKHGPM | AVAFEVHDDF |
| H | LHY ...... | ......... | ......... | ......... | ......... |
| R | LHYHSGIYHH | TGLSDPFNPF | ELTNHAVLIV | GYGKDPVTGL | DYWIVKNSWG |
| H | ......... | ......... | ESIAMAAIPI | PKL | |
| R | SQWGESGYFR | LRRGTDECAI | | | |

Fig. 2

ADAPTER PRIMER FOR FIRST STRAND cDNA SYNTHESIS:

_Mlu 1_     _Spe 1_
5'-GGC-CAC-GCG-TCG-ACT-AGT-AC(T)$_{17}$-3'
    _Not 1 half-site_    _Sal 1_

UNIVERSAL ADAPTER PRIMER FOR cDNA AMPLIFICATION:

_Mlu 1_     _Spe 1_
5'-CUA-CUA-CUA-CUA-GGC-CAC-GCG-TCG-ACT-AGT-AC-3'
               _Not 1 half-site_    _Sal 1_

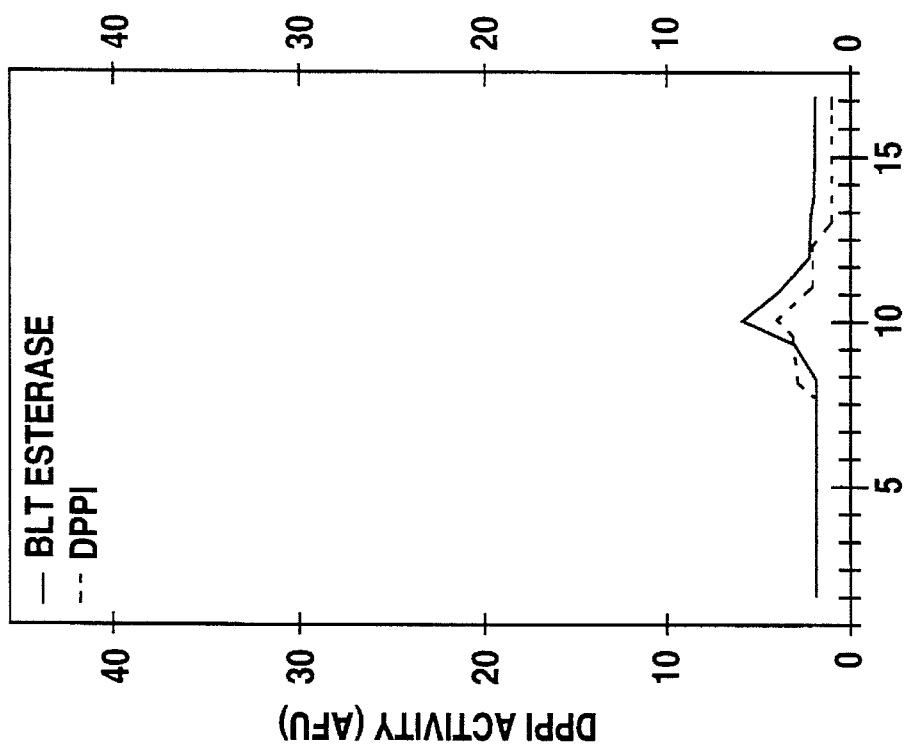
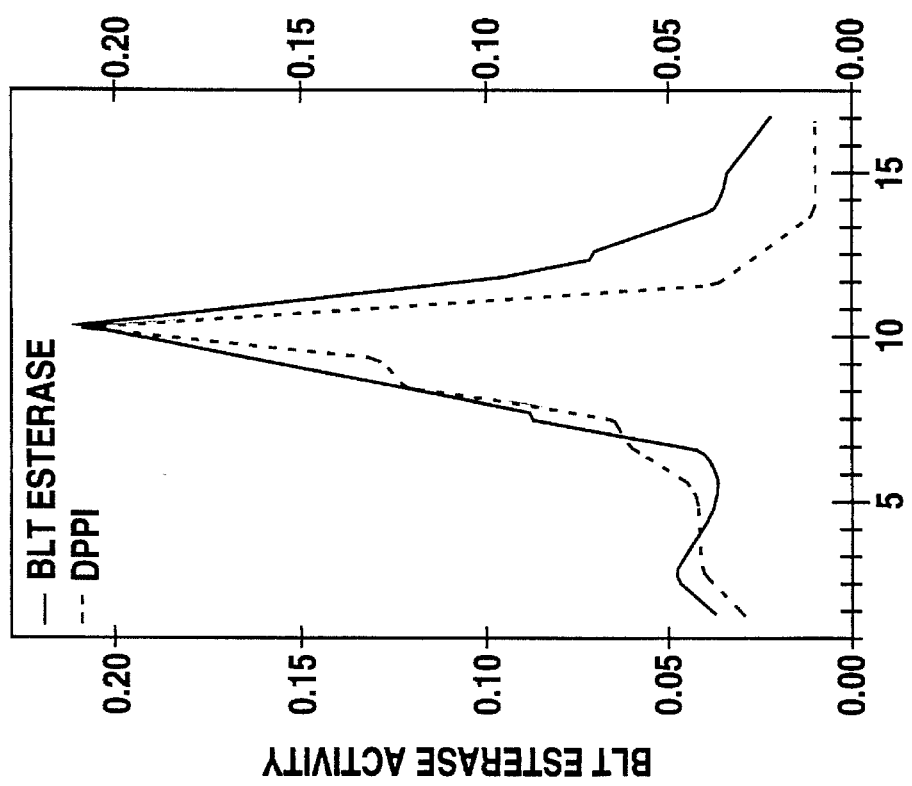
Fig. 11A
Fig. 11B

DP8A: 5'-GC-ATC-ATT-CAT-ICC-ICC-ATA-3'

DPPI 12: 5'-CC-AAA-GTC-CTG-GGC-ATA-3'

AMINO ACID SEQUENCES SURROUNDING THE ACTIVATION DIPEPTIDES OF GRANULE SERINE PROTEASES SYNTHESIZED BY BONE MARROW DERIVED CELLS

| PROTEASE | CELL TYPE | ACTIVATION DIPEPTIDE | | AMINO-TERMINUS OF ACTIVE PROTEASE | | | |
|---|---|---|---|---|---|---|---|
| | | -2 | -1 | 1 | 2 | 3 | 4 |
| HUMAN GRANZYME A | CTL, NK | GLU | LYS | ILE | ILE | GLY | GLY |
| HUMAN GRANZYME B | CTL, NK | GLY | GLU | ILE | ILE | GLY | GLY |
| HUMAN CATHEPSIN G | MYELOID | GLY | GLU | ILE | ILE | GLY | GLY |
| HUMAN PMN ELASTASE | MYELOID | SER | GLU | ILE | VAL | GLY | GLY |
| HUMAN MYELOBLASTIN | MYELOID | ALA | GLU | ILE | VAL | GLY | GLY |
| MURINE GRANZYME A | CTL, NK | GLU | ARG | ILE | ILE | GLY | GLY |
| MURINE GRANZYME B | CTL, NK | GLY | GLU | ILE | ILE | GLY | GLY |
| MURINE GRANZYMES C-G | CTL, NK | GLU | GLU | ILE | ILE | GLY | GLY |
| MURINE TRYPTASE | MAST | GLU | GLU | ILE | VAL | GLY | GLY |

Fig. 21

DIPEPTIDYL PEPTIDASE-I INHIBITORS AND USES THEREOF

BACKGROUND OF THE INVENTION

The government has certain rights in the present invention pursuant to NIH grant AI 24639.

1. Field of the Invention

The present invention relates to the field of immune disease treatments and therapeutic agents. The invention also relates to the identification of the human dipeptidyl peptidase-I gene and the preparation of antisense oligonucleotides thereto. Methods of treating immunologically-mediated diseases and malignancies of myeloid cell or cytotoxic lymphocyte origin are also related to the field of the present invention, particularly methods using particular enzyme inhibitors or antisense oligonucleotides specific for inhibiting the expression of human dipeptidyl peptidase-I.

2. Description of the Related Art

Dipeptidyl peptidase-I (DPPI), previously known as cathepsin C, is a lysosomal enzyme that is present in high levels in natural killer cells, cytotoxic lymphocytes, cytotoxic lymphocyte precursors, and myeloid cells. Cytotoxic lymphocytes and myeloid cells have been shown to contain high levels of dipeptidyl peptidase-I (DPPI) within the specialized cytoplasmic granules of these cells.[5-7] While DPPI has long been noted to be present at higher levels in spleen and other lymphoid organs as compared to liver or other solid organs,[8] it was only with the elucidation of the role of DPPI in Leu—Leu—OMe-mediated toxicity that this enzyme appeared to be a phenotypic marker of myeloid cells and cytotoxic lymphocytes.

DPPI activity has been examined in populations of purified lymphocytes, myeloid cells and cells of non-bone marrow origin. The amount of DPPI activity in these cell types was found by the present inventors to exceed that of non-cytotoxic lymphocytes, B cells and cells of non-bone marrow origin by up to 20-fold.

DPPI isolated from rat, bovine and porcine tissues has been previously shown to be a lysosomal hydrolase capable of sequentially removing dipeptides from the amino-terminus of suitable substrates.[10-13] Highly purified human splenic DPPI has also been shown to demonstrate this substrate specificity. From these reports, the present inventors have determined that a peptide or protein must have an unblocked amino-terminus and the terminal residue cannot be arginine or lysine in order to be a suitable substrate for human DPPI. In addition, the bond to be cleaved must not involve a proline residue. It is clear that with these few limitations, DPPI has a broad substrate range.

DPPI has been characterized as the only known members of the papain enzyme family that exhibits only exopeptidase activity. DPPI has also been characterized as an unusually large molecule, having a molecular weight of 200,000 Da. The other non-DPPI lysosomal thiol proteases are generally monomeric proteins with molecular weights less than 30,000 Da. As a member of the thiol-dependent peptide hydrolases, DPPI is inhibited by general thiol-modifying reagents, such as n-ethylmaleimide, mercurial salts and iodoacetate, by thiol protease inhibitors such as the cystatins and specifically by the active site directed inhibitor, glycylphenylalanine diazomethane.[17-19]

In addition to the above-described hydrolytic activity, these forms of DPPI have also been shown to catalyze the polymerization of dipeptide amides and esters.[6,7,9,20-24] This polymerization activity is favored at neutral to alkaline pH, but exhibits a substrate specificity comparable to an acidic hydrolytic activity. The ability of DPPI to polymerize dipeptide esters mediates the toxicity of Leu—Leu—OMe, as this molecule is known to be polymerized to longer peptide chain lengths and is responsible for the toxicity observed with this dipeptide ester within DPPI-enriched cells.[6-7] These extended (Leu—Leu)$_n$—OMe polymers, are capable of lysing red blood cells and may have similar effects on the intracellular components of the cells that are sensitive to Leu—Leu—OMe.[6,7,9]

The role of DPPI in such toxicity was identified by the present inventors through the use of specific inhibitors of DPPI activity, in particular Gly—Phe—$CHN_2$. While the DPPI dependence of Leu—Leu—OMe toxicity characterized by the present inventors provided the initial motivation for the purification and characterization of this enzyme, the high level of DPPI expression in lymphocytes with cytolytic potential and myeloid cells suggested that an unknown, yet potentially important role for DPPI existed in the function of lymphocytes and myeloid cells. The pattern of DPPI expression and its spectrum of enzymatic activity suggested to the present inventors that DPPI played a role in the post-translational processing and activation of a family of serine proteases expressed only in cells of bone marrow origin.

Lymphocytes with cytolytic potential, natural killer cells, mast cells, and granulocytes express distinct members of a family of serine proteases that have not been identified in other cell types.[25-84] These distinct members of the serine protease family of enzymes include the granzymes (found in lymphocytes, natural killer cells), mast cell tryptase and chymase (found in mast cells), leukocyte elastase, cathepsin G, and myeloblastin (found in granulocytes) (Table 1).

TABLE 1

Serine Proteases of Bone Marrow Derived Cells

| Protease | Cell Type |
|---|---|
| granzymes | cytotoxic T lymphocytes, natural killer cells |
| tryptase | mast cells |
| chymase | mast cells |
| elastase | granulocytes, immature myelomonocytic cells |
| cathepsin G | granulocytes, immature myelomonocytic cells |
| myeloblastin | granulocytes, immature myeloid cells |

While these enzymes share some structural and catalytic features with pancreatic serine proteases, such as trypsin, they have other features that make them unique. The pancreatic serine proteases are stored within the pancreatic exocrine cells in an inactive proenzyme or zymogen form,[49,50] and are synthesized with a typical signal sequence that directs them into lumen of the endoplasmic reticulum. When the signal peptide is cleaved off the nascent protein chain, an "activation" peptide is retained which limits proteolytic activity until the protease is secreted from the cell. The presence of the "activation" peptide is common among the pancreatic proteases. The length of the activation peptide varies from 6 to 20 residues, but always ends with an arginine or lysine.[51-53] Therefore, each of the pancreatic proteases can be isolated as a zymogen and activated by treatment with trypsin. The proteases of the complement or clotting cascades are similarly secreted as "inactive" zymogens into the circulation that are activated by cleavage at a specific arginine or lysine (trypsin-sensitive) residue.[54]

In contrast to the pancreatic serine proteases, the serine proteases of bone marrow cells have only recently been isolated in an inactive zymogen form.[55] The inactive zymogen form of these enzymes does not accumulate in cells. Rather, they are transient proteins that limit the activity of the enzyme between the site of synthesis and the cytoplasmic granule, the site where active proteases accumulate. The structure of the synthetic intermediates of these serine proteases was originally deduced from genomic or cDNA cloning studies. All of these serine protease genes contain sequences encoding a typical signal peptide that directs them into the endoplasmic reticulum, followed by a dipeptide predicted to serve as the activation peptide, and then the amino-terminus of the mature enzyme.[25-48] These features are illustrated by the junction sequences of human cathepsin G (HCG), leukocyte elastase (HLE), myeloblastin (MYB), and granzyme A (HGA) (Table 2). The amino-terminus of the active form of each enzyme isolated from cells is underlined. The consensus signal peptidase cleavage site and the cleavage site required to obtain the mature enzyme are marked by arrows.

TABLE 2

Amino Acid Sequences Near the Mature N-Termini of Bone Marrow Serine Proteases

| Protease | Signal Sequence | | | | Dipeptide | | N-Terminus | | | |
|---|---|---|---|---|---|---|---|---|---|---|
| | −6 | −5 | −4 | −3 | −2 | −1 | 1 | 2 | 3 | 4 |
| HCG | Gly | Ala | Glu | Ala | Gly | Glu | +e,fra Ile+ee | Ile | Gly | Gly |
| HLE | Thr | Ala | Leu | Ala | Ser | Glu | +e,fra Ile+ee | Val | Gly | Gly |
| MYB | Ala | Ala | Arg | Ala | Ala | Glu | +e,fra Ile+ee | Val | Gly | Gly |
| HGA | Glu | Asp | Val | Cys | Glu ↑ | Lys | +e,fra Ile+ee ↑ | Ile | Gly | Gly |

It is clear from the sequences shown above that, with the exception of granzyme A, the processing of these serine protease enzymes could not be carried out by a trypsin-like protease. Therefore, a distinct mechanism must exist for the activation of the serine proteases. Inspection of the deduced amino acid sequences of the serine proteases associated with bone marrow derived cells suggested to the inventors that in each case, the dipeptide "activation" peptide would be a suitable substrate for DPPI.

Salvesen and Enghild demonstrated the transient presence of a dipeptide-bearing form of elastase and cathepsin G in U-937 cells[80]. This form was judged not to be catalytically active based on failure to interact with an affinity matrix, aprotinin-agarose. However, there was no direct measurement of hydrolysis of specific peptide or protein substrates. In addition, the enzyme responsible for the dipeptide processing and activation of these serine proteases has not been identified. The identification of the enzyme responsible for the processing/activation of serine proteases was, however, believed to be important to characterizing and controlling the cell-mediated cytotoxicity caused by cell types found by the present inventors to have high concentrations of these enzymes.

Cell mediated cytotoxicity has been shown to be a major component of immune responses directed against allogeneic tissues.[3,6] Defining the role of cytotoxic lymphocytes during evolution of alloimmune responses is made difficult in part because of the heterogeneity of functions mediated by phenotypically similar lymphocytes. Whereas studies of both human and murine T-cells have indicated that the bulk of T cytokine production and helper function is mediated by CD4(+) T-cells, and as the majority of cytotoxic effector cells are CD8(+), a number of exceptions to this generalization have been noted. For example, in alloimmune responses, both T-cytokine and T-cytotoxic responses directed against Class II MHC differences have been shown to be mediated by CD4(+)T-cells, whereas isolated Class I MHC differences stimulate cytokine and cytotoxic responses from CD8(+)T-cells.[9,10] Therefore, expression of CD8 or CD4 cannot be used to identify T-cell subsets which specifically manifest cytotoxic activity.[9-11]

Approaches based on differential screening of cDNA libraries have identified "CTL specific" serine proteases including granzymes A–G in the mouse and granzyme A and granzyme B in the human.[12-18] Transcription of genes for these proteases precedes acquisition of cytolytic effector function during primary in vitro mixed lymphocyte cultures (MLC).[19]

The present Inventors postulate a role for effector cells expressing the granzyme A gene in allograft rejection.

However, a specific role for granzymes in CTL effector function has been difficult to demonstrate directly. For example, whereas inhibitors of granzyme A or B activity have been shown to impair CTL lytic function, virtually all such inhibitors act on broad classes of serine proteases.[23] Thus, it is not clear that granzymes are the sole target of these inhibitors. Although purified granzymes have not been demonstrated to have direct lytic activity, granzyme A may play other roles, such as in CTL-mediated degradation of target cell DNA,[24] or in modifying the activity of other granule associated effector molecules.[25] Granzyme A gene expression in infiltrating lymphocytes has already been reported to be a useful marker of human cardiac rejection.[22] Granzymes may also play a role in mediating rapid detachment of activated lymphocytes from targets.[26] Granzyme A may be a growth factor for B or T-cells[27,28] or may be active in the degradation of extracellular matrix proteins.[29] Thus, while it is clear that granzymes are expressed uniquely by cells with cytotoxic potential, their precise role in cytolysis remains to be identified.

Target cell injury induced by CTL is characterized by a pattern of early nuclear condensation and DNA fragmentation that is not observed following complement-mediated lysis.[39] While perforin containing granules and chromatographically purified perforin have been reported in one study to induce DNA degradation,[40] other investigators have not been able to induce target cell DNA fragmentation even with highly purified perforin preparations.[41] A number of investigators have suggested that CTL mediated lysis may involve multiple mechanisms.[10] Moreover, while granzyme and perforin expressing granular effector cells appear to be the predominate mediators of spontaneous natural killer cell function and alloantigen-specific CTL function generated in primary in vitro MLC, agranular allospecific CTL without detectable granzyme A or perforin activity have been reported to be induced following in vivo intraperitoneal priming with allogeneic cells.[43]

It appeared to the present inventors that use of specific inhibitors of DPPI enzymatic activity of or the development of a specific antisense oligonucleotide directed against the expression of DPPI would provide a selective and potent means of controlling the processing of the serine proteases, and thereby the cellular damage induced thereby, in pathologies which involved the activity of cells of bone marrow origin. Such was supported by the observations of the inventors that DPPI was important to the function of several types of cell damage mediated by lymphocytes, or by myeloid cells via granule serine protease mediated mechanisms.

It appeared to the present inventors that specific forms of antisense therapy directed toward inhibiting the expression of the human DPPI gene or the human DPPI protein would provide a potential therapy for the treatment of many human diseases linked to the action or malfunction of cytotoxic lymphocytes on cells of myeloid lineage, such as leukemia, GVHD, graft rejection, and the like. However, neither the protein or the gene for human DPPI had been characterized. Only recently has the sequence for the rat DPPI protein and rat cDNA clone been reported[79]. However, prior to purification of human DPPI, the human DPPI protein, which had not yet been characterized, could not be used to determine if any homology with the rat DPPI protein existed. Therefore, significant technical difficulties remained in both isolating the human protein and isolating the human gene which encodes the protein, before the types of specific oligonucleotide DPPI inhibitors contemplated by the inventors could be synthesized.

In light of the present inventors' work regarding the important role of DPPI in the activation of cells of bone marrow origin and the role of DPPI dependent effector on mechanisms in several human pathologies, the development of particular antisense oligonucleotides specific for binding the human DPPI gene and/or RNA would provide an important therapeutic tool in the treatment of immunologically related diseases.

SUMMARY OF THE INVENTION

The present invention provides the identification of an important human protein, dipeptidyl peptidase-I, and the characterization of this protein at the gene level. Even more importantly, methods found effective for inhibiting the cytotoxic activity in tissues with cells having high concentrations of human dipeptidyl peptidase-I are disclosed in the present application. These methods are demonstrated by the present inventors to provide selective potential treatments for inflammatory diseases as well as malignancies and other disorders of myeloid cell origin.

More specifically, the methods of the invention employ chemical agents shown to be capable of selectively inhibiting DPPI activity in natural killer cells, cytotoxic T-lymphocytes, and myeloid cells. Some of these agents may be more particularly described as thiol modifying agents in terms of their biochemical activity. These compounds are shown by the inventors to have a high inhibitor specificity for human dipeptidyl peptidase-I, thus rendering DPPI incapable of processing granule serine protease "proenzymes" to their enzymatically active forms, thus inhibiting the actions of these enzymes in tissue detruction or other effector functions of cytotoxic lymphocytes or myeloid, while preserving and fostering non-myeloid cell growth and maturation.

While the human dipeptidyl peptidase-I inhibitors of the invention may encompass a variety of different compounds, both molecular and enzymatic, specific examples of such inhibitors include agents defined by the structure:

NH$_2$—CH(R$_1$)—CO—NH—CH(R$_2$)—CO—X wherein R$_1$ is H, —CH$_2$OH, —CH(CH$_3$)$_2$, —CH$_2$CH(CH$_3$)$_2$, or a lower alkyl; R$_2$ is a lower alkyl, —CH$_2$CH(CH$_3$)$_2$, —CH$_2$Ph, or CH$_2$(p-hydroxyphenyl) or other uncharged alkyl; and X is —CHN$_2$, —CH$_2$F, or —CH$_2$S(CH$_3$)$_2$, and wherein said agent selectively inhibits DPPI activity in natural killer cells, cytotoxic T-lymphocytes and myeloid cells. Most preferably, the lower alkyl is defined as an alkyl chain of 1 to 6 carbons. By way of example, such agents may include:

glycyl-phenylalanine diazomethane

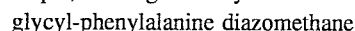
Gly—Phe—CH$_2$F

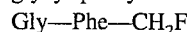
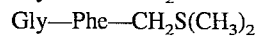
Gly—Phe—CH$_2$S(CH$_3$)$_2$

Ser—Leu—CHN$_2$

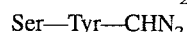
Ser—Tyr—CHN$_2$

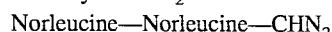
Norleucine—Norleucine—CHN$_2$

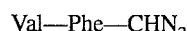
Val—Phe—CHN$_2$

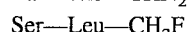
Ser—Leu—CH$_2$F

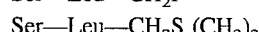
Ser—Leu—CH$_2$S (CH$_3$)$_2$

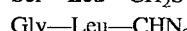
Gly—Leu—CHN$_2$

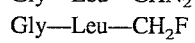
Gly—Leu—CH$_2$F

Most preferably, the human dipeptidyl peptidase-I inhibitors of the present invention are glycyl-phenylalanine diazomethane, Gly—Phe—CH$_2$F, Gly—Phe—CH$_2$S(CH$_3$)$_2$, Ser—Leu—CHN$_2$, Ser—Tyr—CHN$_2$, Norleucine—Norleucine—CHN$_2$, Val—Phe—CHN$_2$, Ser—Leu—CH$_2$F, Ser—Leu—CH$_2$S (CH$_3$)$_2$, Gly—Leu—CHN$_2$, and Gly—Leu—CH$_2$F. The most preferred human dipeptidyl peptidase-I inhibitor of the present invention is glycyl-phenylalanine diazomethane (Gly—Phe—CHN$_2$).

In still another aspect of the present invention, a human dipeptidyl peptidase protein isolatable from human spleen tissue is isolated and characterized. The human protein has been identified to have a blocked amino terminus. The sequence of human DPPI has been defined by the present inventors as including at least part of the human sequence defined herein in FIG. 2. The human peptide dipeptidyl peptidase-I identified and partially sequenced by the present inventors has a native molecular weight of about 200,000 daltons composed of eight 24 kDa subunits and a pI of 5.4. The enzymatic activity of this protein has been shown by the present inventors to be specifically inhibited by several agents, most particularly the DPPI inhibitor, Gly—Phe—CHN$_2$.

The dipeptidyl peptidase-I inhibitors of the present invention also include particular oligonucleotides, specifically, antisense oligonucleotides, which inhibit the expression of the human DPPI gene. These antisense oligonucleotides may therefore be used in the treatment of inflammatory disease and malignancy of myeloid cell origin. These oligonucleotides, particularly antisense oligonucleotides, are defined by the present inventors as having a sequence which is complementary to a sequence of the messenger RNA that encodes DPPI.

While an oligonucleotide of a variety of lengths which includes a sequence complimentary to the human dipeptidyl peptidase-I gene may be employed in the practice of the present invention, antisense oligonucleotide species which include a length of between 15-mer and 50-mer as the size of the oligonucleotide are most preferred. The most preferred forms of the antisense oligonucleotides are contemplated to be those of a 17-mer to 24-mer length. By way of example, these 17 mer-to 24-mer antisense oligonucleotides include the following:

(1) 5'-AC-AAA-GTT-GAT-GCC-ATG-3' (17-mer)

(2) 5'-TT-GAT-TCC-ATG-IAC-ATT-3' (17-mer)

(3) 5'-CC-AAA-GTC-CTG-GGC-ATA-3' (17-mer)

(4) 5'-CC-AAA-ATC-TTG-IGC-ATA-3' (17-mer)

(5) 5'-CC-AAA-GTC-CTG-IGC-ATA-3' (17-mer)

(6) 5'-CC-AAA-ATC-CTG-IGC-ATA-3' (17-mer)

(7) 5'-CC-AAA-GTC-TTG-IGC-ATA-3' (17-mer)

(8) 5'-GC-ATC-ATT-CAT-ICC-ICC-ATA-3' (20-mer)

(9) 5'-TTC-AAA-GGC-AAC-TGC-CAT-GGG-3' (21-mer)

(10) 5'-CTA-CAA-TTT-AGG-AAT-CGG-TAT-GGC-3' (24-mer)

These oligonucleotides were used as primers for PCR which were amplified for detection of the human DPPI gene.

As used in defining the oligonucleotides of the present invention, the abbreviation "I" stands for inosine. Inosine has the capability to base pair with any of the 5 possible nucleotides that naturally occurs in DNA or RNA. The referenced antisense oligonucleotides were determined employing information obtained by the inventors regarding the particular protein sequence of human dipeptidyl peptidase-1 protein fragments. Additional oligonucleotides will be defined upon the determination of the cDNA sequence of human DPPI.

In still another aspect of the present invention, a method for inhibiting malignancies of myeloid cell origin in an animal is provided. The method, most preferably, will comprise treating the animal with a pharmacologically effective amount of an inhibitor of dipeptidyl peptidase-I sufficient to suppress cytotoxic T-lymphocyte activity in the animal. As the human dipeptidyl peptidase-I inhibitors described herein have been found to be effective in inhibiting proliferation of cells of myeloid origin, it is contemplated that the method may be effective in the treatment of a malignancy defined as myeloid leukemia. Again, the dipeptidyl peptidase inhibitors may constitute a thiol modifying reagent. The inhibitors most preferred in the described method include those listed above, and most preferably glycyl-phenylalanine diazomethane, Gly—Phe—CH$_2$F, Gly—Phe—CH$_2$S(CH$_3$)$_2$, Gly—Phe—CHN$_2$, Ser—Tyr—CHN$_2$, Norleucine—Norleucine—CHN$_2$, Val—Phe—CHN$_2$, Ser—Leu—CHN$_2$ or Ser—Leu—CH$_2$F, Ser—Leu—CH$_2$S(CH$_3$)$_2$.

Alternatively, the dipeptidyl peptidase-I inhibitor of the present invention may constitute an oligonucleotide which is capable of specifically inhibiting the synthesis of human dipeptidyl peptidase-I. This oligonucleotide is more particularly defined as an antisense oligonucleotide which inhibits synthesis by inhibiting the expression of a human dipeptidyl peptidase-I gene. This antisense oligonucleotide may be even further defined as having a sequence complementary to the messenger RNA that encodes DPPI. Examples of particular antisense oligonucleotides contemplated for use in the method include those defined as antisense oligonucleotides #1–#10 as described supra. Again, other sequences will be determined upon the even further characterization of the human cDNA, according to those methods described in the present disclosure and results reported herein.

In one most preferred application of the described method, the dipeptidyl peptidase-I inhibitor is Gly—Phe—CHN$_2$. The present inventors propose that the described method will be useful in the treatment of an animal such as a human or a rat.

In still another aspect of the present invention, a method for treating an immunologically mediated disease in an animal is provided. This method, in a most general application, comprises treating the animal with a pharmacologically effective amount of a dipeptidyl peptidase-I inhibitor sufficient to inhibit cytoxic T lymphocyte or natural killer cell activity. The immunologically mediated disease to be treated in the afore-described method may constitute, for example, organ allograft rejection, graft versus host disease, or an alloimmune disease. By way of example, a dipeptidyl peptidase-I inhibitor defined in the list provided above, or more preferably as glycyl-phenylalanine diazomethane, Gly—Phe—CH$_2$F, Gly—Phe—CH$_2$S(CH$_3$)$_2$, Ser—Leu—CHN$_2$, Ser—Tyr—CHN$_2$, Norleucine—Norleucine—CHN$_2$, Val—Phe—CHN$_2$, Ser—Leu—CH$_2$F, or Ser—Leu—CH$_2$S(CH$_3$)$_2$, may be employed as the agent of choice in the method. Most preferably, the dipeptidyl peptidase inhibitor of choice is glycyl-phenylalanine diazomethane. It is contemplated that the pharmacologically effective amount of the dipeptidyl peptidase-I inhibitor to be employed, where the inhibitor is Gly—Phe—CHN$_2$, is between about 3 mg/kg to about 30 mg/kg.

While any number of tissue or organ allograft rejections may be treated according to the described invention, it is contemplated that the method may have particular utility in treating and inhibiting a kidney, heart or skin rejection in an animal, such as in a human.

Where the method is employed to treat an immunologically mediated disease, such as an autoimmune disease, the inventors contemplate utility of the method in the treatment of inflammatory diseases mediated by cytotoxic lymphocytes or effector cells of myeloid origin.

In still another aspect of the present invention, a cancer chemotherapeutic agent for the treatment of malignancies of myeloid cell or cytoxic lymphocyte origin is provided. The agent is more fully defined as comprising an oligonucleotide capable of inhibiting human dipeptidyl peptidase-I in myeloid or lymphoid origin malignant cells or as a protease inhibitor. Most preferably, the cancer chemotherapeutic agent comprises an antisense oligonucleotide which is capable of specifically inhibiting the expression of a human dipeptidyl peptidase-I gene. By way of example, such an antisense oligonucleotide is demonstrated as including a sequence complementary to the messenger RNA that encodes DPPI. In one most preferred aspect of the cancer chemotherapeutic agent, the inventors contemplate particular utility for use thereof in the treatment of leukemia.

The present invention also provides a specific cDNA useful for detecting a human dipeptidyl peptidase-I gene. This cDNA may be described as consisting essentially of a complete or partial nucleotide sequence, encoding an N-terminal fragment of DPPI, most particularly human DPPI. The present invention will also provide an expression vector which includes the cDNA of human dipeptidyl peptidase-I. This expression vector is described as most preferably comprising the vector pGEM3Zf or pCB6.

In still another aspect of the invention, a method for inhibiting a bone marrow graft rejection in an immunosuppressed patient is provided. The method comprises pretreating the bone marrow graft with a therapeutically effective amount of an antisense oligonucleotide capable of specifically inhibiting the expression of a human dipeptidyl peptidase-I gene, and administering the pretreated bone marrow graft to the immunosuppressed patient. The particular antisense oligonucleotide capable of inhibiting human dipeptidyl peptidase-I is further defined as resistant to nuclease degradation.

The antisense oligonucleotide contemplated as useful in the methods described herein is further defined as capable of inhibiting dipeptidyl peptidase-I activation of serine protease proenzymes. By way of example, the serine protease proenzymes include the granzymes, myeloblastin, tryptase, chymase cathepsin G and leukocyte elastase.

The present invention also provides a method for preparing an about 1,000-fold purified human dipeptidyl peptidase-I. This method, in a most preferred aspect, comprises obtaining a human spleen tissue, homogenizing the tissue in an acidic hypotonic homogenization buffer in a ratio of 5 ml buffer per 1 gram tissue, obtaining a pellet and a first supernatant from the homogenate, reextracting the pellet from the tissue homogenate in a volume of the acidic hypotonic homogenization buffer with Triton X-100 of about 2.5 ml per gram of the pellet, and saving a second supernatant, combining the first supernatant and the second supernatant, heating the combined supernatants to about 55°–60° C. for about 30 minutes, cooling the heated supernatant to room temperature and adjusting the pH to about 7.5, passing the combined supernatant sample over a concanavalin A-agarose column, eluting dipeptidyl peptidase-I from the column and collecting the chromatographed sample, passing the chromatographed sample over a mercurial affinity chromatography column and collecting a human dipeptidyl peptidase-I fraction, and concentrating the human dipeptidyl peptidase-I fraction on a high capacity anion exchange resin and resolving the fraction by gel filtration to provide an about 1,000-fold purified preparation of human dipeptidyl peptidase-I. The yield of human dipeptidyl peptidase-I purified protein according to the afore-described method is about 100 micrograms of a 1,000-fold purified human dipeptidyl peptidase-I per 100 grams of human spleen tissue processed.

Other human tissues may be used to extract the human DPPI according to the afore-described method. However, the yield of human DPPI per gram tissue may vary.

The following list includes abbreviations used throughout the description of the present invention:

DPPI=dipeptidyl peptidase-I
CB, CD, CG, CH=cathepsin B, D, G, H
PMN=peripheral mononuclear leukocytes
HCG=human cathepsin G
HLE=human leukocyte elastase
MYB=myeloblastin
HGA=granzyme A
I=inosine
NK=natural killer cell
CTL=cytotoxic T lymphocytes
SpC=spleen cells
PEL=peritoneal exudate lymphocytes
MLC=mixed lymphocyte culture
PMSF=phenylmethylsulfonylfluoride
TLCK=1-chloro-3-tosylamido-7-amino-2-heptanone
TPCK=Tosylamino-2-phenylethyl chloromethyl ketone
BMC=bone marrow stem cell
E:T=effector to target ratio

BRIEF DESCRIPTION OF THE DRAWINGS

EL4 Sn=supernatant of phorbol dibutyrate stimulated EL4 rat cells

MNA=methoxynaphthylamine

β-NA=β-naphthylamine

BCIP/NBT=bromochloroindolephosphate --nitroblue tetrazolium--

FIG. 2. Alignment of the tryptic peptide sequences of MLC=mixed leukocyte culture human DPPI with the sequence of rat DPPI enzyme.

AFU=arbitrary fluorescence unit

NBT=nitroblue tetrazolium

Figure 3:
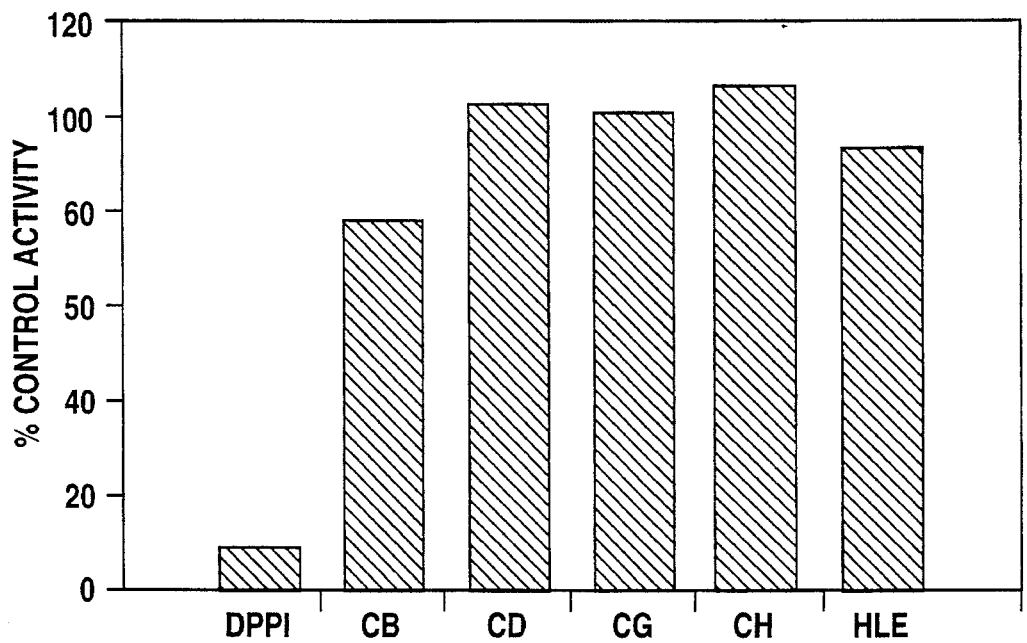

FIG. 3. U-937 cell enzymes inhibitor specificity (DPPI, CB, CD, CG, CH, HLE). Gly—Phe—$CHN_2$ specifically inhibits DPPI. U-937 cells were cultured in the presence of 3 µM Gly—Phe—$CHN_2$ or diluent (0.15% DMSO, control) for one hour. A cell extract was prepared and assayed for the activity of both cytoplasmic and lysosomal/granule protease activities.

Figure 4:
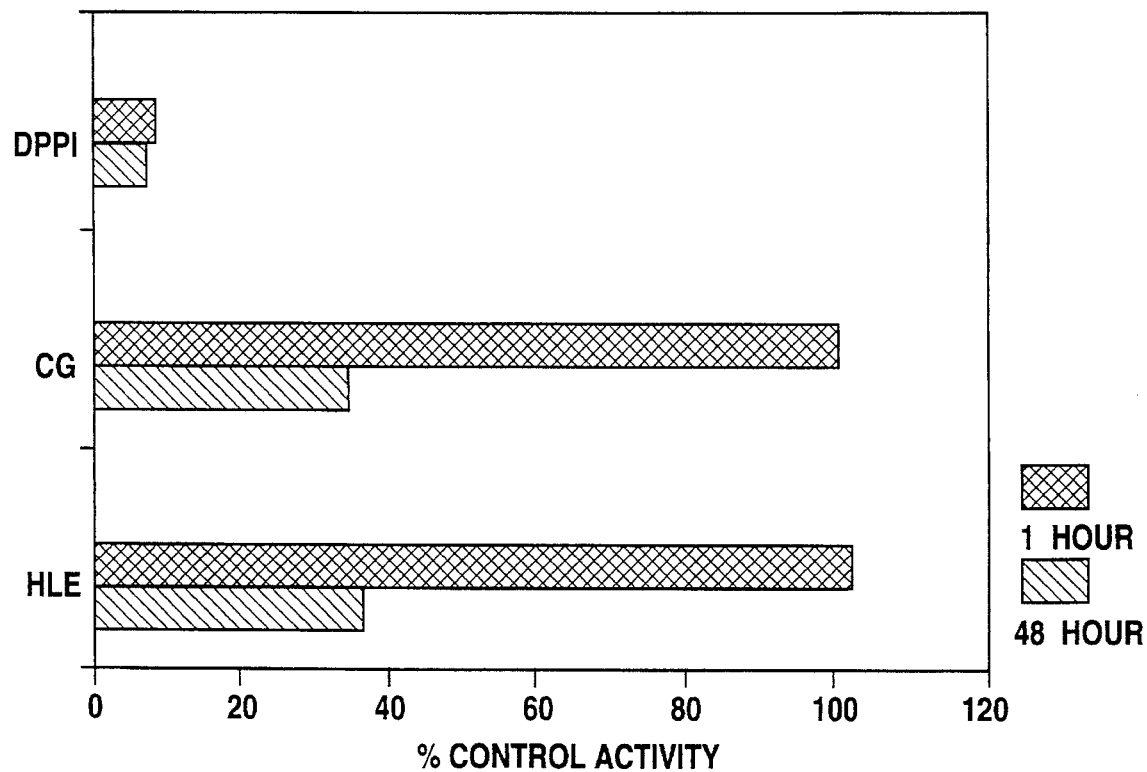

FIG. 4. Short vs. long term effects of Gly—Phe—$CHN_2$, a DPPI inhibitor, on dipeptidyl peptidase-I, cathepsin G and elastase activities in U-937 cells. Cells were incubated for 48 hours in the presence or absence of 3 µM Gly—Phe—$CHN_2$.

Figure 5A:
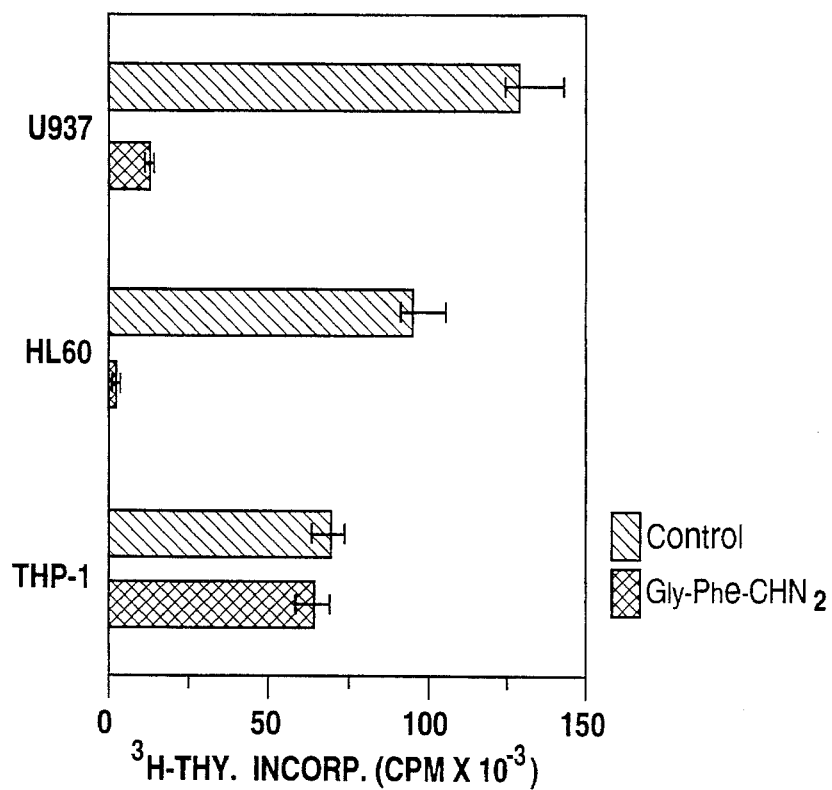
Figure 5B:
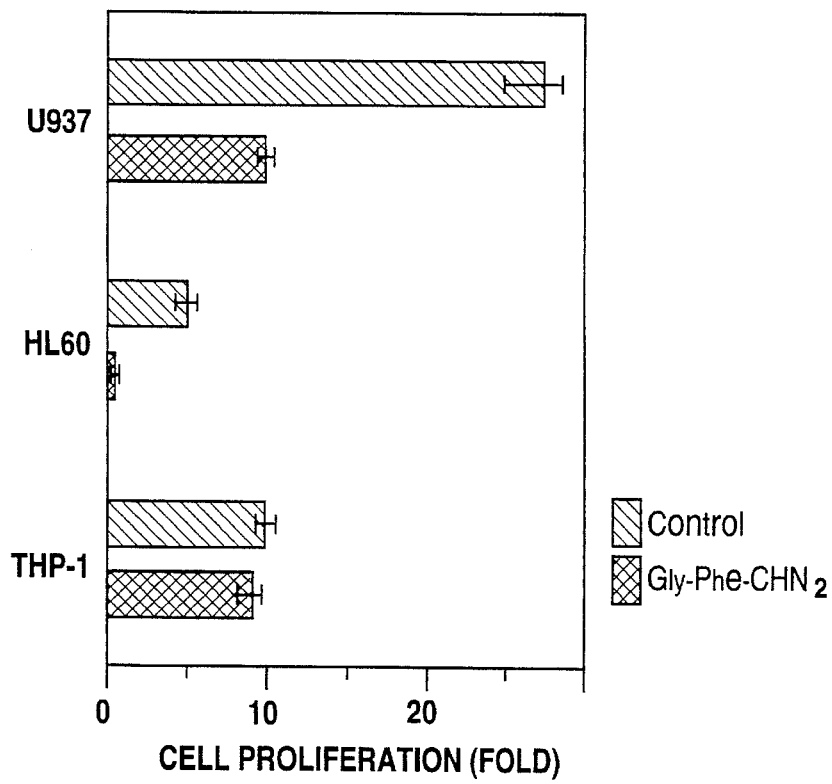

FIGS. 5A and 5B. FIG. 5B shows inhibition of myeloid cell proliferation after 4 days exposure to Gly—Phe—$CHN_2$. Long term cultures were incubated with 3 µM Gly—Phe—$CHN_2$. FIG. 5A $^3$H-thymidine incorporation was measured during the last 8 hours of culture. HL60 is a relatively undifferentiated myeloid cell line, THP-1 is a myeloid tumor cell line.

Figure 6A:
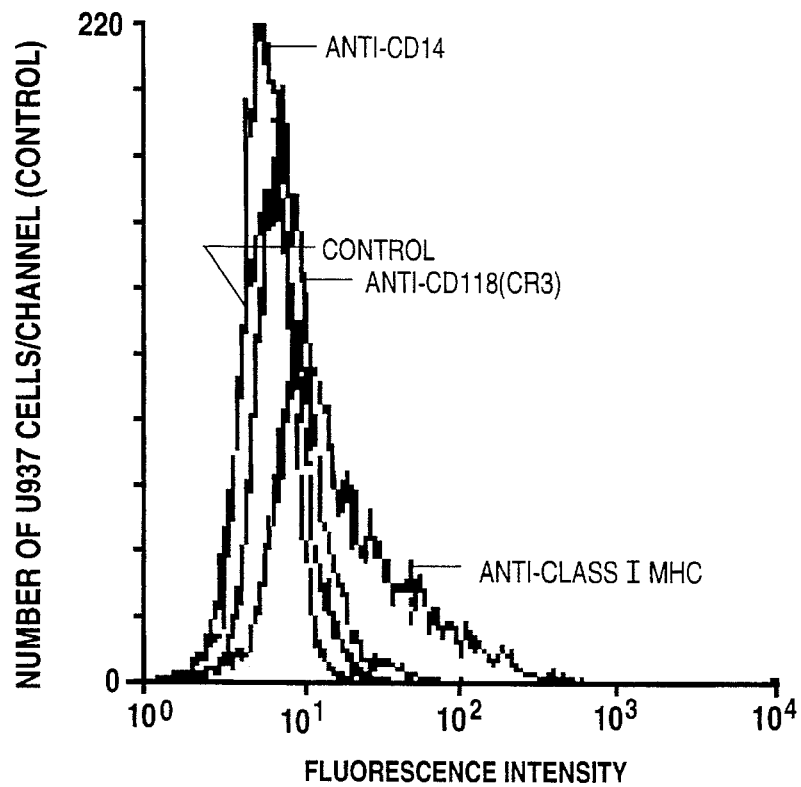
Figure 6B:
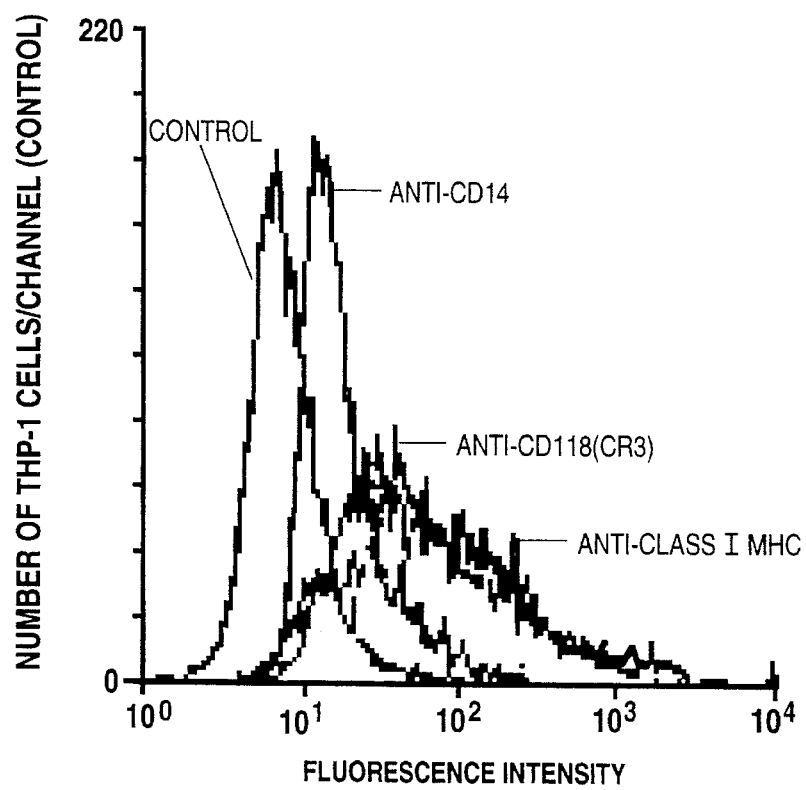
Figure 6C:
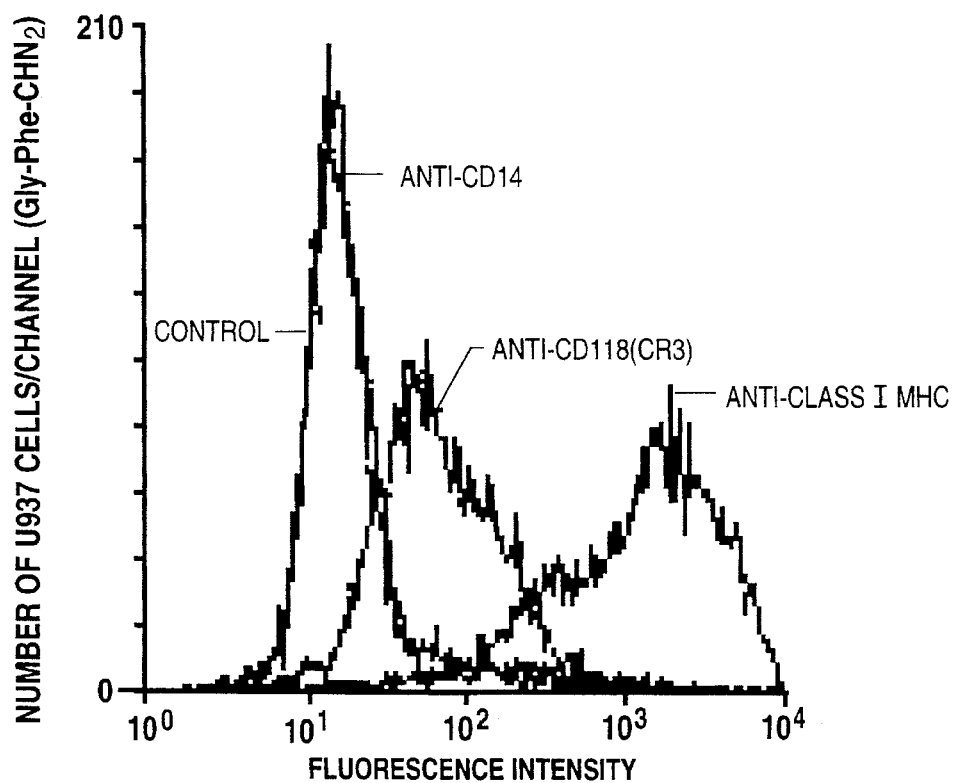
Figure 6D:
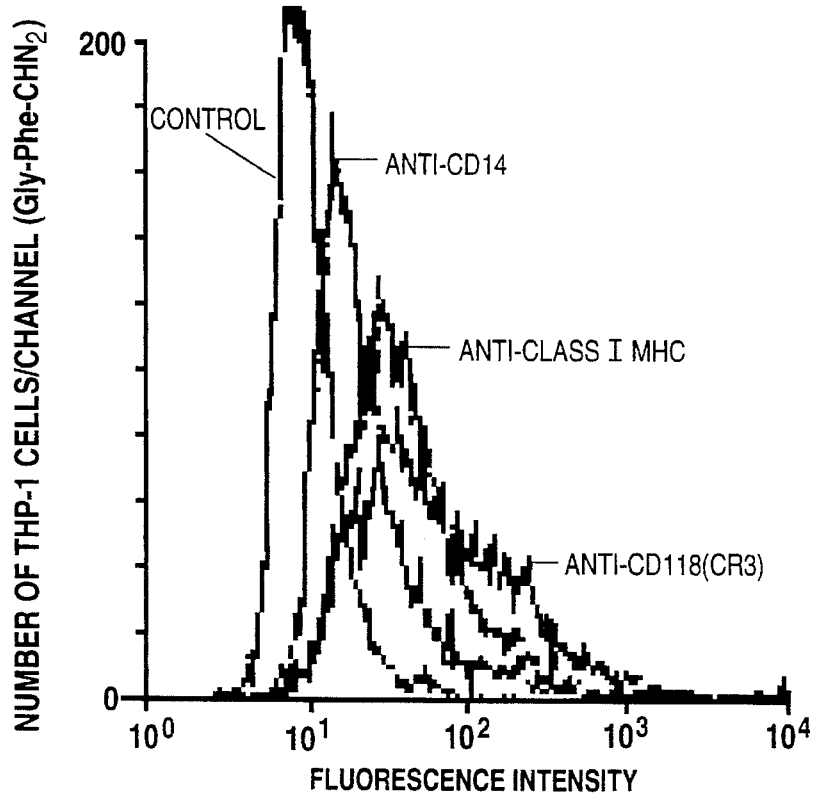

FIGS. 6A–6D. FIG. 6A and 6D show Gly—Phe—$CHN_2$ has no effect on expression of antigens in the myeloid tumor cell line THP-1. FIG. 6A and 6C show that Gly—Phe—$CHN_2$ induces antigenic expression in the U-937 cell line characteristic of differentiation to monocytes.

Figures 7, 8:
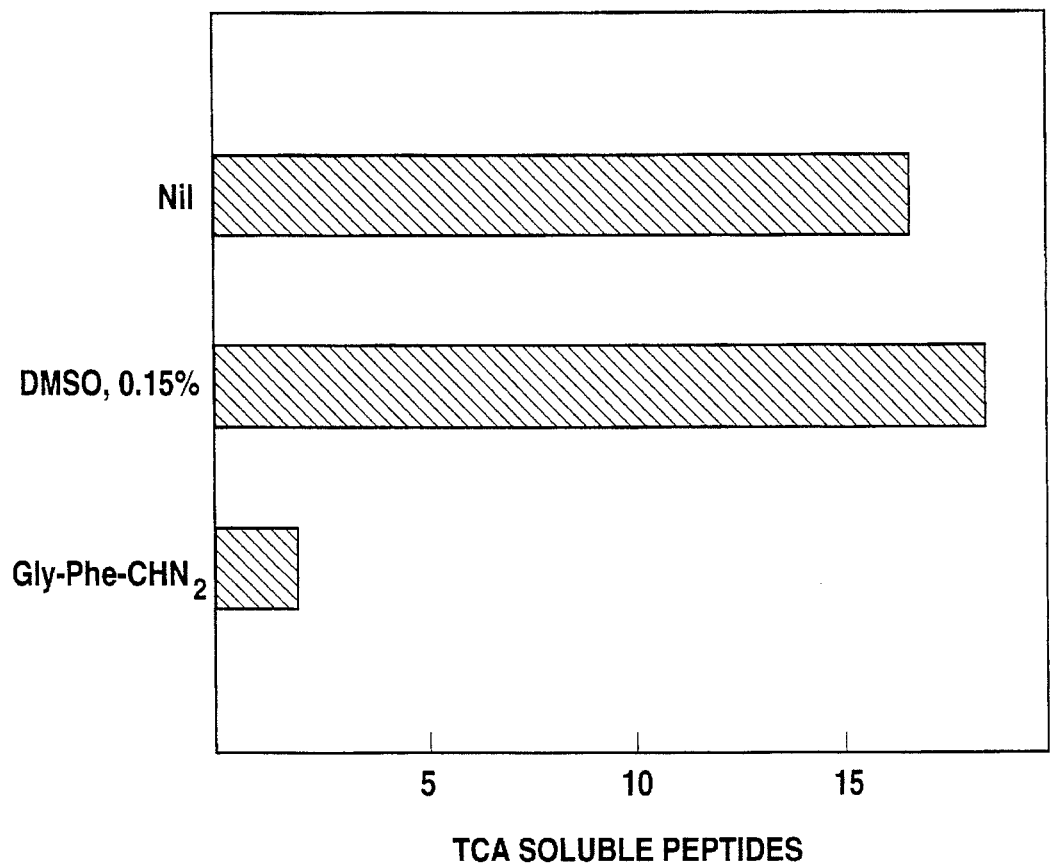

FIG. 7. Serine protease activity in Gly—Phe—$CHN_2$ treated cells as assayed using casein as a substrate instead of synthetic peptide substrates.

FIG. 8. 3' Race System Primers (G1BCO BRL)

Figure 9B:
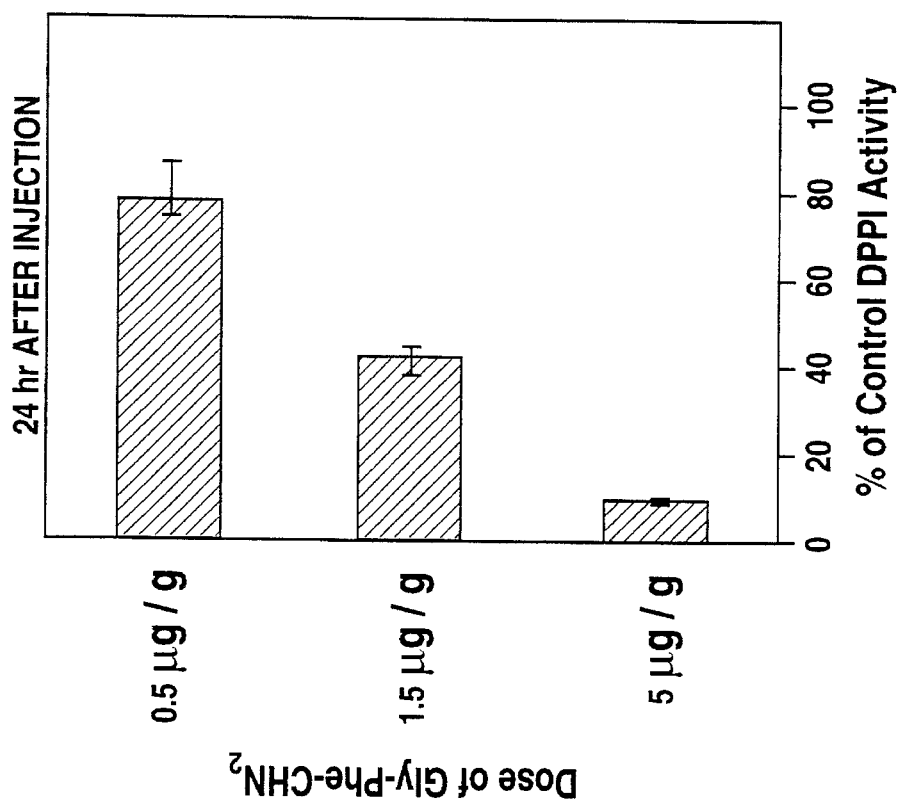
Figure 9A:
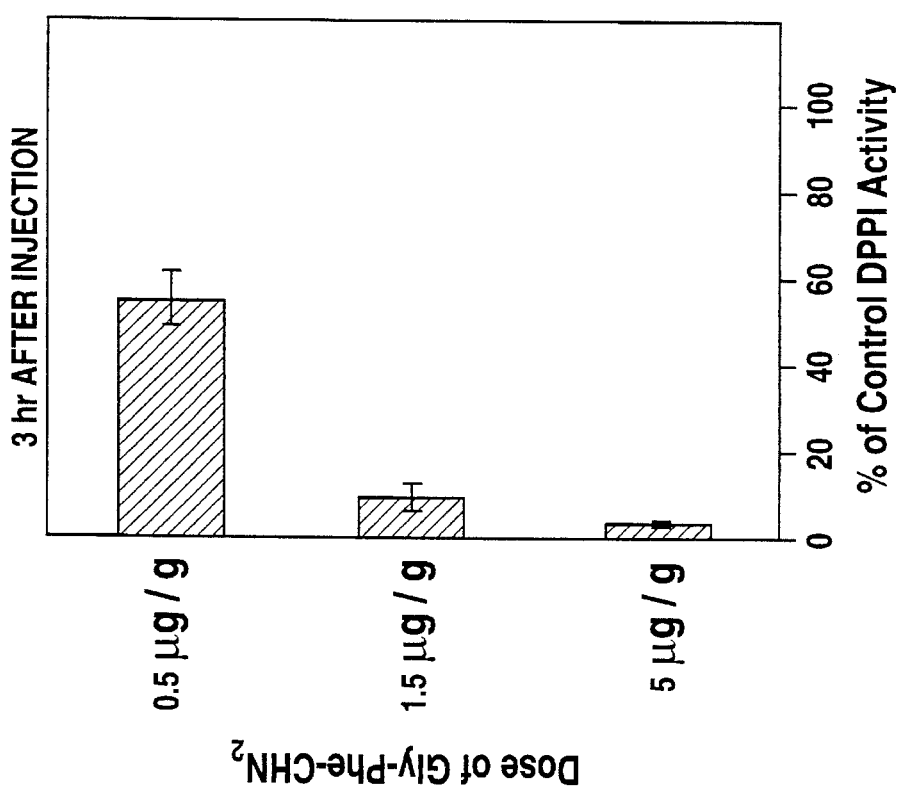

FIGS. 9A and 9B. FIG. 9A demonstrates inhibition of DPPI activity in murine spleen cells 3 hours after intraperitoneal injections of 0.5–5 µg/g Gly—Phe—$CHN_2$. FIG. 9B demonstrates inhibition of DPPI activity in murine spleen cells 24 hours after intraperitoneal injections of 0.5–5 µg/g Gly—Phe—$CHN_2$.

Figure 10B:
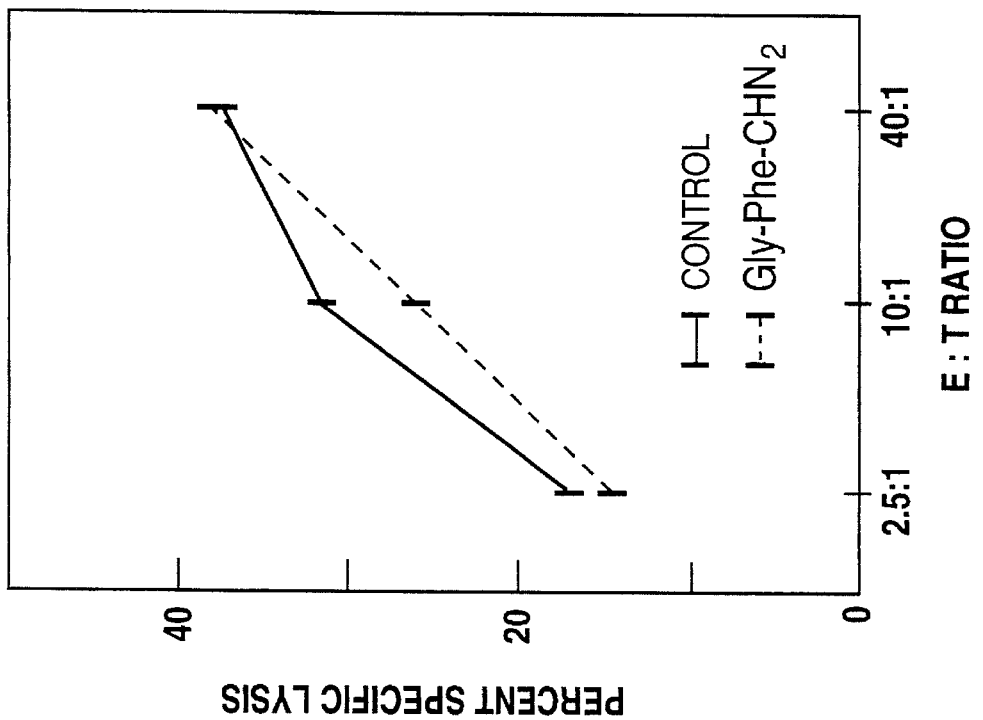
Figure 10A:
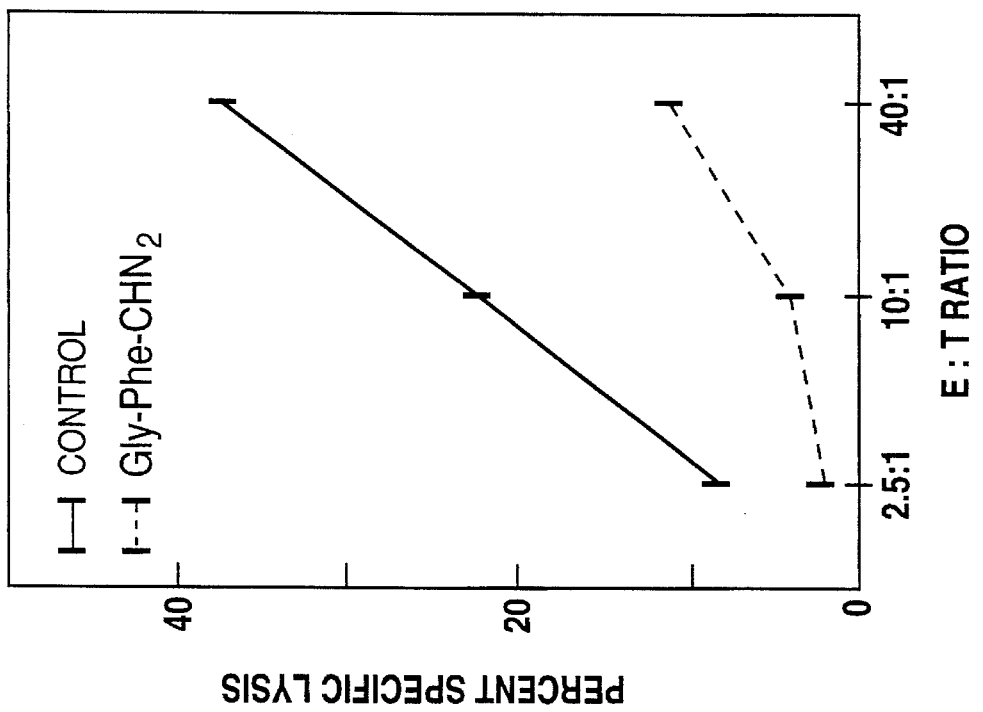

FIGS. 10A and 10B. FIG. 10A (no additional culture) shows cells that 24 hours before CTL assay, washed and placed into cultures free of Gly—Phe—$CHN_2$. FIG. 10B (cultured in 2% EL4 Sr and no inhibitor×24hr) shows CTL activity returned to levels similar to that seen with control cultures.

FIGS. 11A and 11B. FIG. 11A shows control PBL activity. FIG. 11B shows Leu—Leu—OMe treated PBL. Granzyme A (BLT esterase) activity and DPPI activity co-isolate in the same granular fraction within lymphokine activated cells.

Figures 12, 13A, 13B:
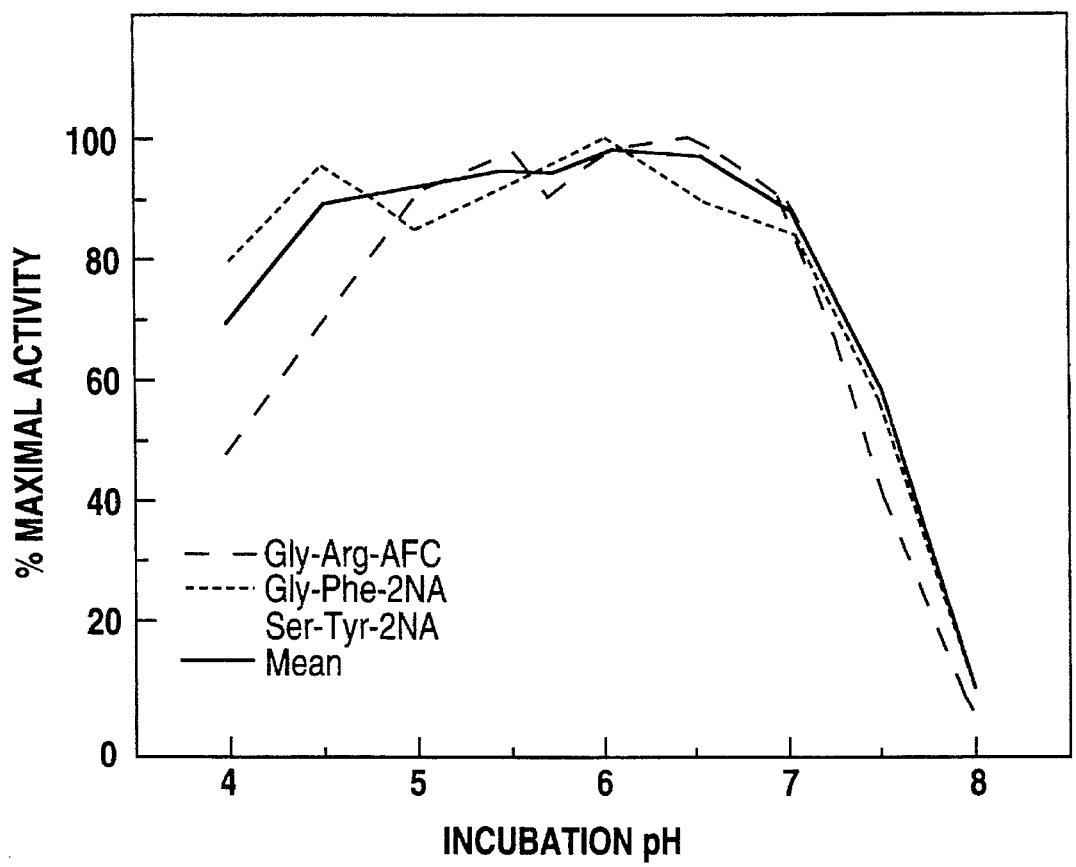

FIG. 12. Effect of pH on the rate of substrate hydrolysis. Purified human DPPI was assayed for the hydrolysis of synthetic peptide substrates over a pH range of 4 to 8. Assay buffers used were: acetic acid/sodium acetate for pH 4.0 to 5.5; sodium phosphate mono/dibasic for pH 5.7 to 8.0.

FIGS. 13A–13B. The oligonucleotide probes used to screen a λgt11 library for the gene that encodes DPPI. The probes are a 17-mer and a 20-mer used to screen duplicate lifts of plated λgt11 library. FIG. 13 A=DP8A 5'-GC-ATC-ATT-CAT-ICC-ICC-ATA-3'; FIG. 13B=DP12 5'-CC-AAA-GTC-CTG-GGC-ATA-3'.

Figure 14B:
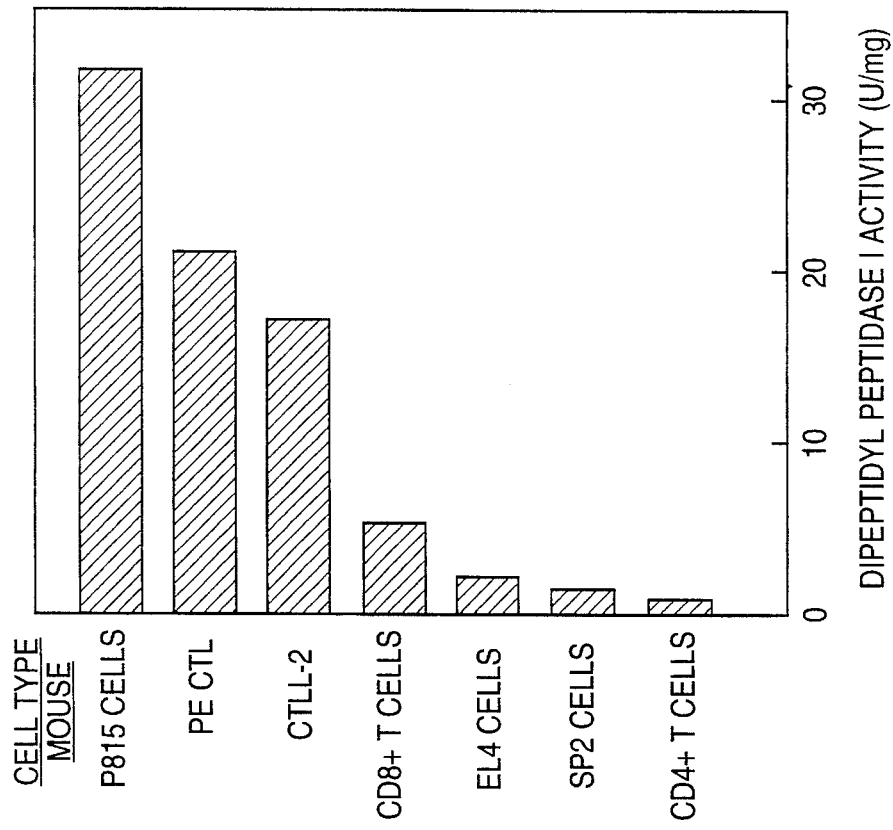
Figure 14A:
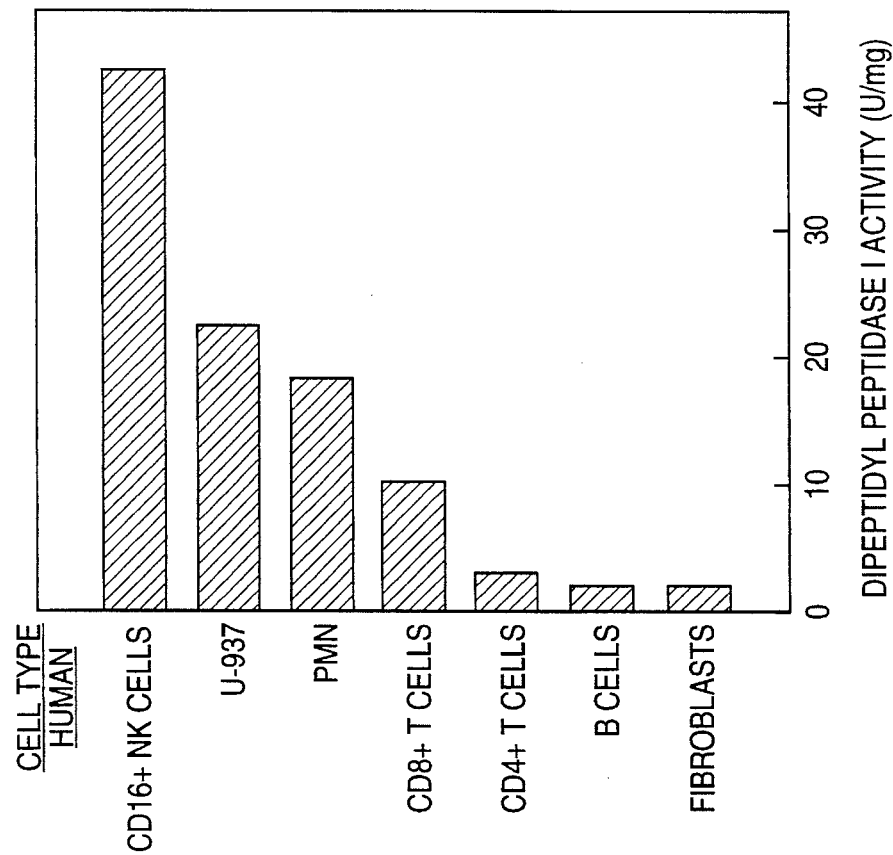

FIGS. 14A and 14B. FIG. 14A demonstrates DPPI Activity levels in human cells and cell lines. FIG. 14B demonstrates DPPI activity levels in murine cells and cell lines. DPPI activity was determined by the hydrolysis of Gly—Phe—βNA as described previously. The results are expressed as nmol βNA produced/min/mg soluble protein.

Figures 15A, 15B:
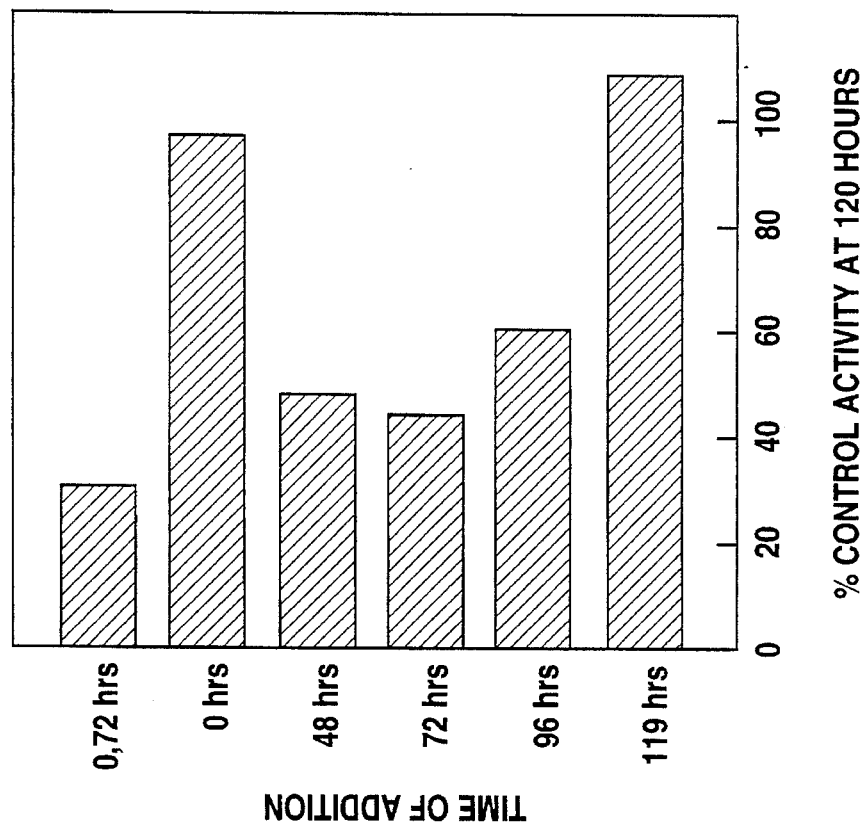

FIGS. 15A–15B. Effect of Gly—Phe—$CHN_2$ on the generation of BLT esterase activity in murine CD8(+) alloantigen-stimulated T-cells. Gly—Phe—$CHN_2$ (3 µM) or 0.15% methyl sulfoxide was added at the times indicated to lymphocytes cultured as described herein. All cells were harvested after 120 hours and assayed for DPPI and BLT esterase activity as well as protein. FIG. 15A=DPPI; FIG. 15B=BLT esterase.

Figure 16:
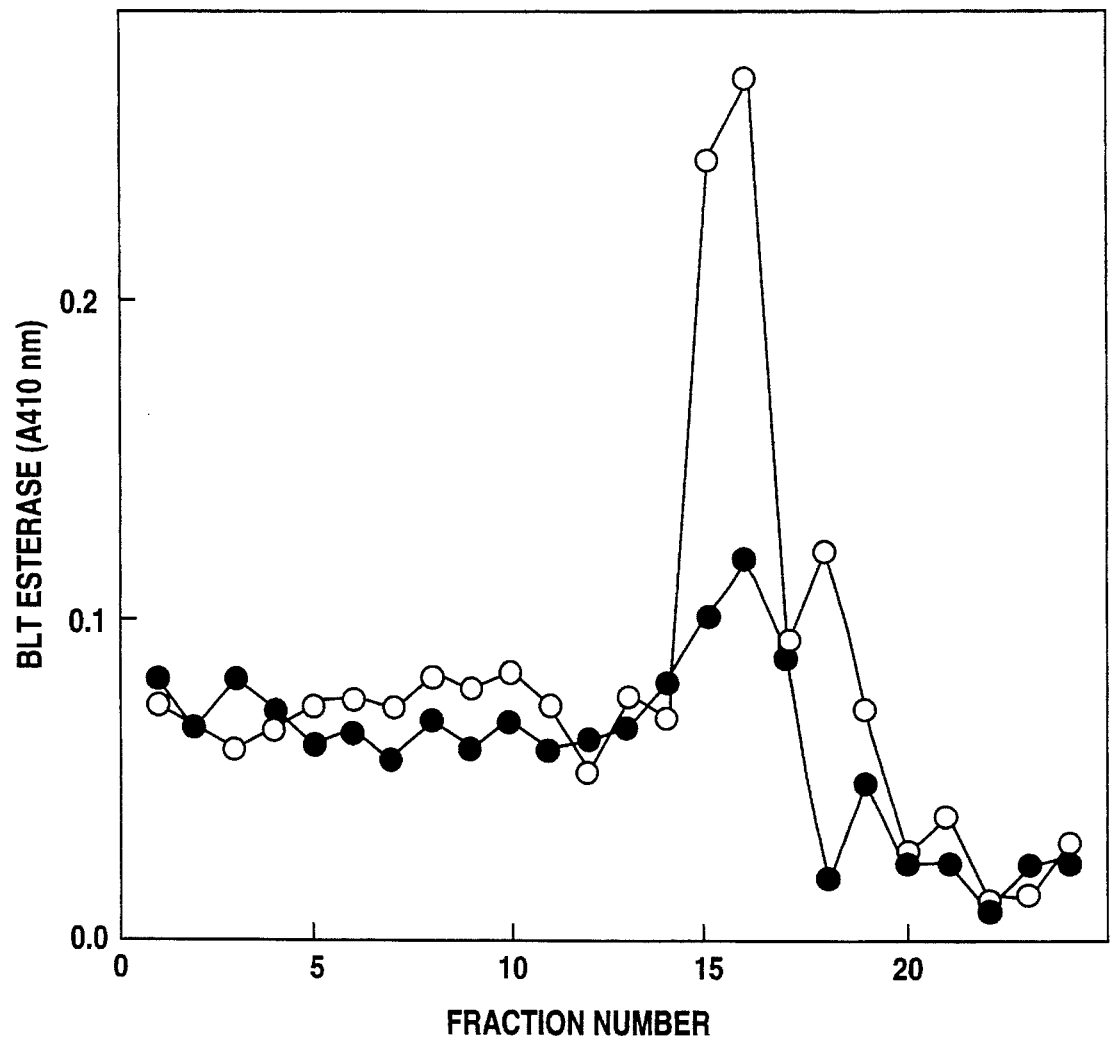
Figure 17A:
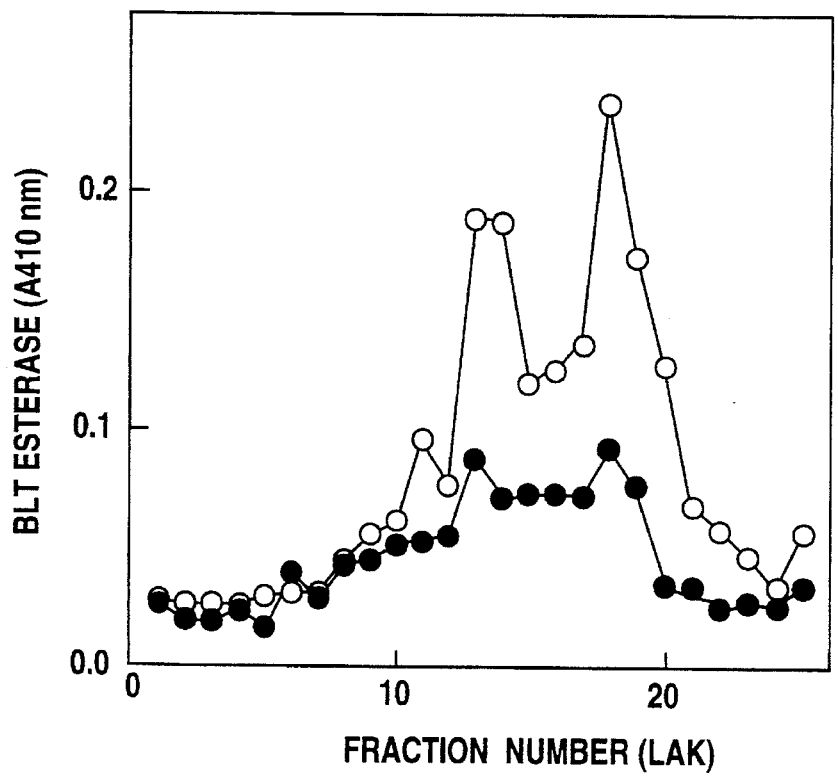
Figure 17B:
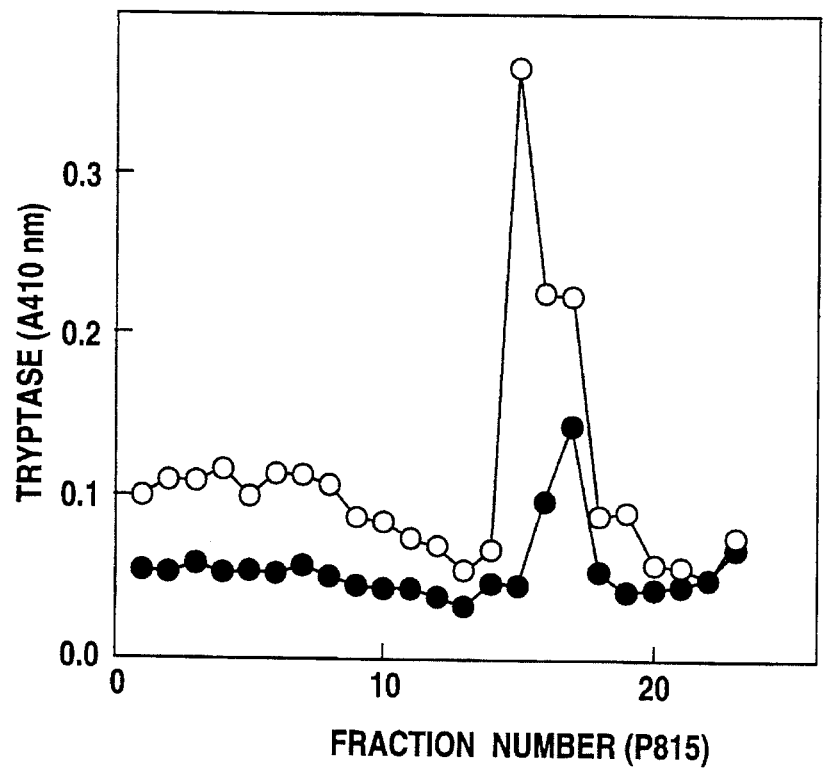
Figure 17C:
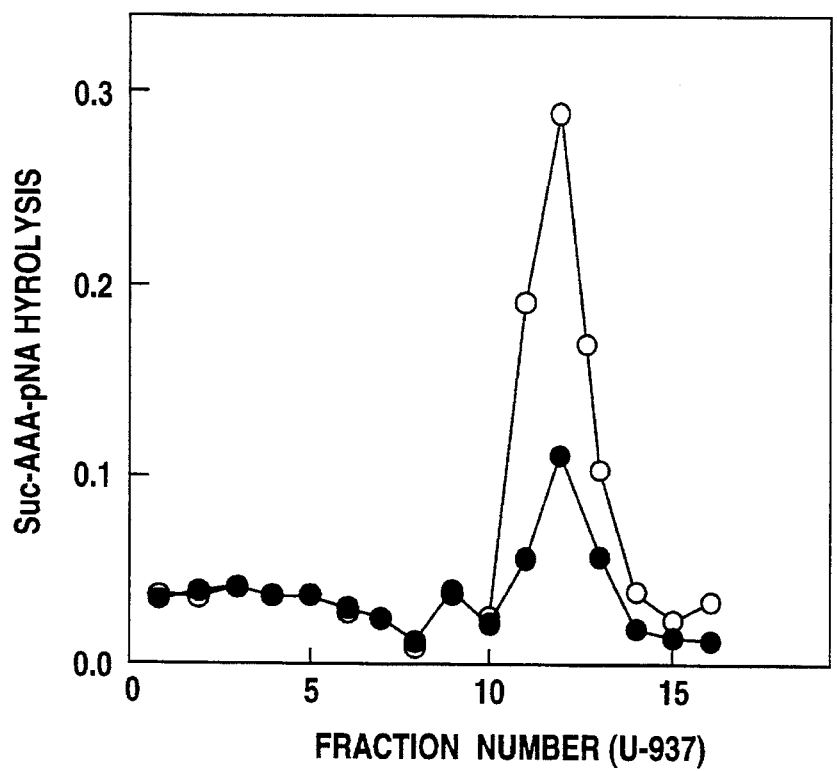
Figure 17D:
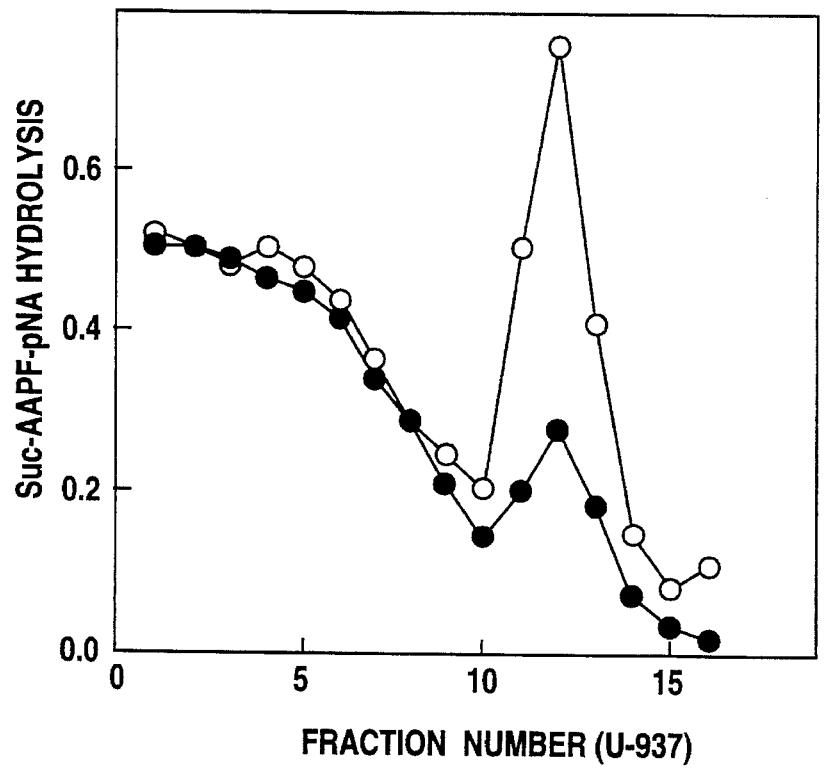

FIG. 16. Effect of Gly—Phe—$CHN_2$ on the generation of granule associated BLT esterase activity in murine CD8(+) alloantigen-stimulated T-cells. Murine CD8(+) T-cells were isolated and cultured as described herein in the presence (●) or absence (○) of 3 µM Gly—Phe—$CHN_2$, added at the start of culture and after 48 hours. Cells are harvested, homogenized and fractionated on Percoll gradients. Gradient fractions were assayed for BLT esterase activity and results are expressed as the change in $A_{410}$nm per 30 minutes. DPPI assays indicated >95% inhibition of this activity in cells cultured in the presence of Gly—Phe—$CHN_2$.

FIGS. 17A–17D. Effect of Gly—Phe—$CHN_2$ on the generation of granule serine protease activity in human and murine bone marrow derived cells. Human lymphocytes (FIG. 17A), murine mastocytoma cells (FIG. 17B), and a human myeloid cell line (FIG. 17C and FIG. 17D) were cultured in the presence or absence of 3 µM Gly—Phe—$CHN_2$, homogenized and fractionated on Percoll gradients. The gradient fractions were assayed for granzyme A (FIG. 17A), mast cell tryptase (FIG. 17B), leukocyte elastase (FIG. 17C) and cathepsin G (FIG. 17D) activities. (Open cirucles (○) equal control cultures (absence of Gly—Phe—$CHN_2$), closed circles (●) equal cultures in the presence of Gly—Phe—$CHN_2$).

Figure 18A:
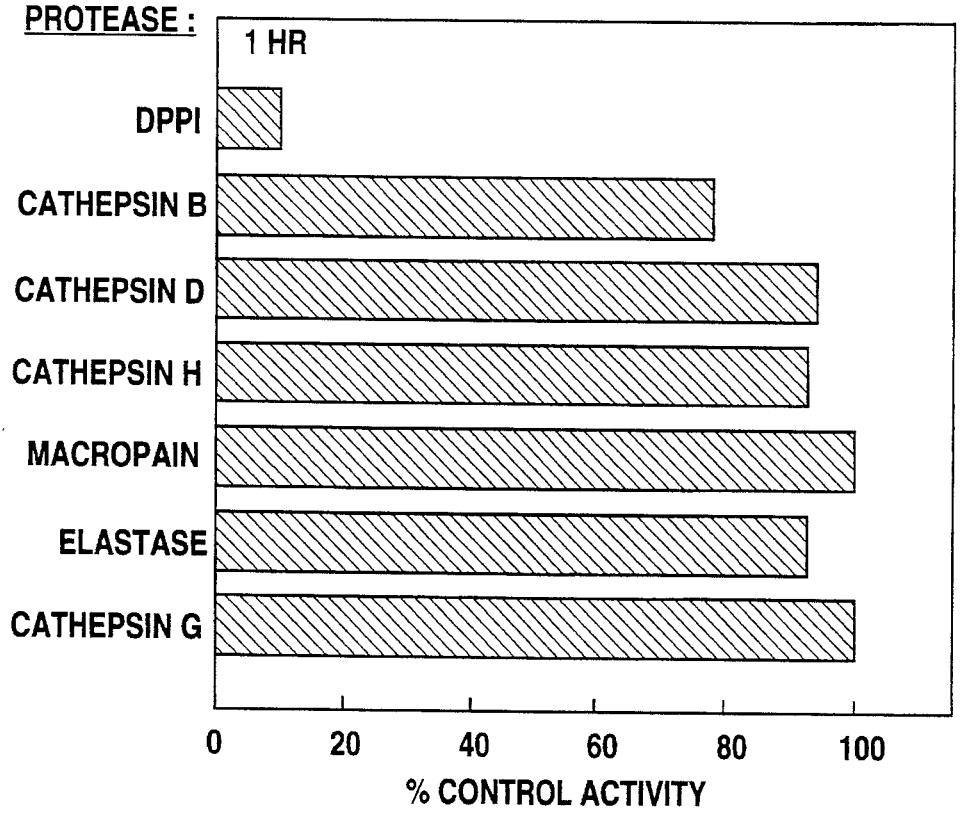
Figure 18B:
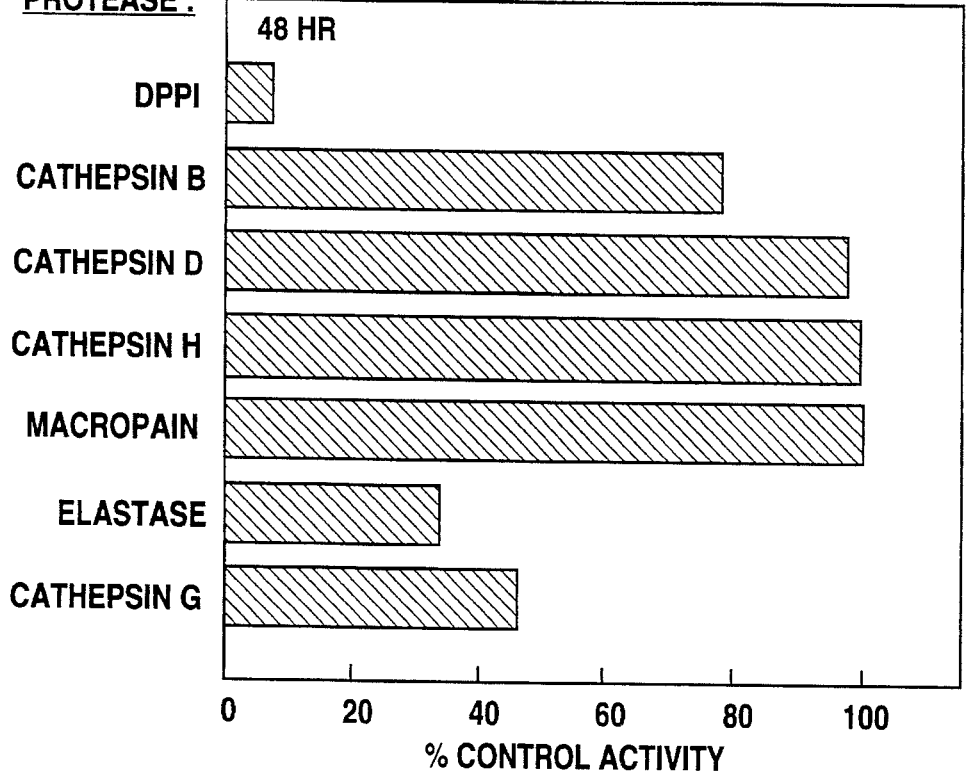

FIGS. 18A–18B. Effect of Gly—Phe—$CHN_2$ on the proteolytic activities of U-937 cells. U-937 cells were cultured in the presence or absence of Gly—Phe—$CHN_2$ for 1 hour (FIG. 18A) or 48 hours (FIG. 18B) prior to homogenization, Percoll gradient fractionation and assay of various proteolytic activities. For each proteolytic enzyme, the results are expressed as the % activity in cells exposed to Gly—Phe—$CHN_2$ compared to control cells incubated in 0.15% methyl sulfoxide.

Figures 19A, 19B:
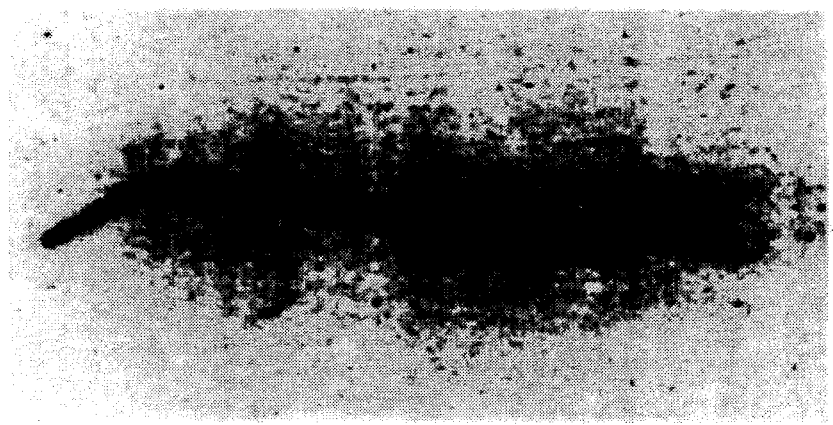

FIGS. 19A–19B. Levels of anti-cathepsin G immunoreactive protein are equivalent in U-937 cells cultured in the presence or absence of Gly—Phe—$CHN_2$. Granule proteins, from cells cultured in the presence (FIG. 19A) or absence (FIG. 19B) of Gly—Phe—$CHN_2$, were separated by SDS-PAGE and transferred to nitrocellulose and probed with rabbit anti-human cathepsin G antibodies (Calbiochem). Immunoreactive protein was visualized with goat anti-rabbit immunoglobulin-alkaline phosphatase conjugate and BCIP/NBT substrates.

Figure 20A:
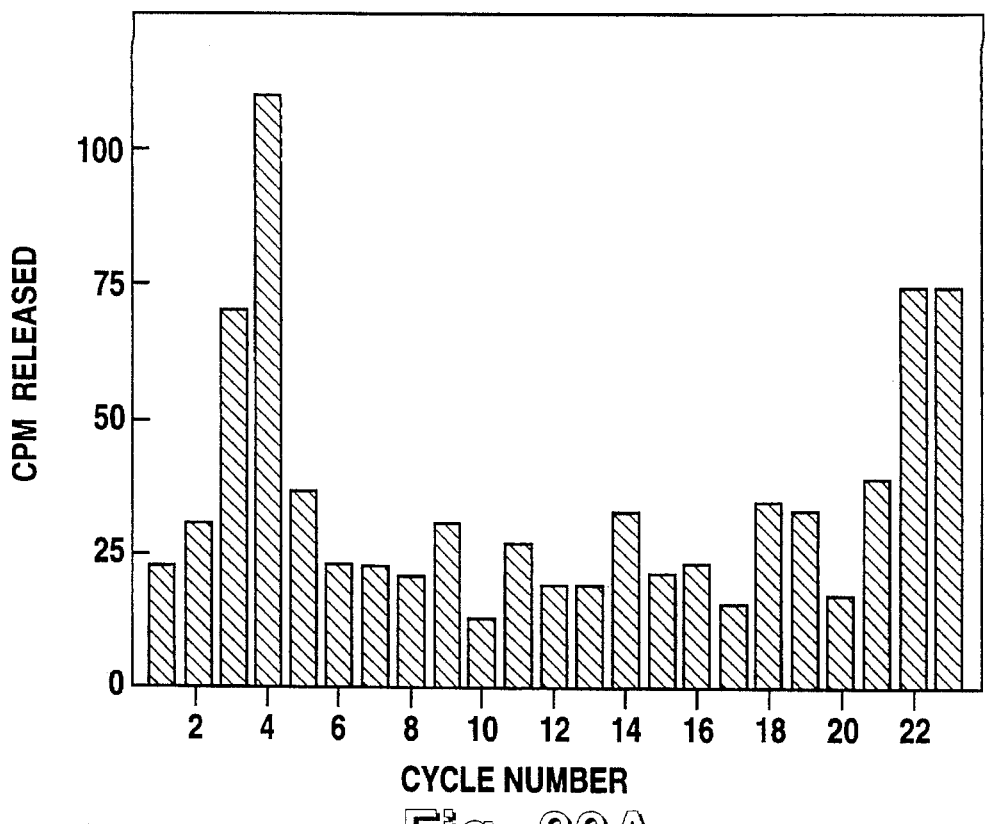
Figure 20B:
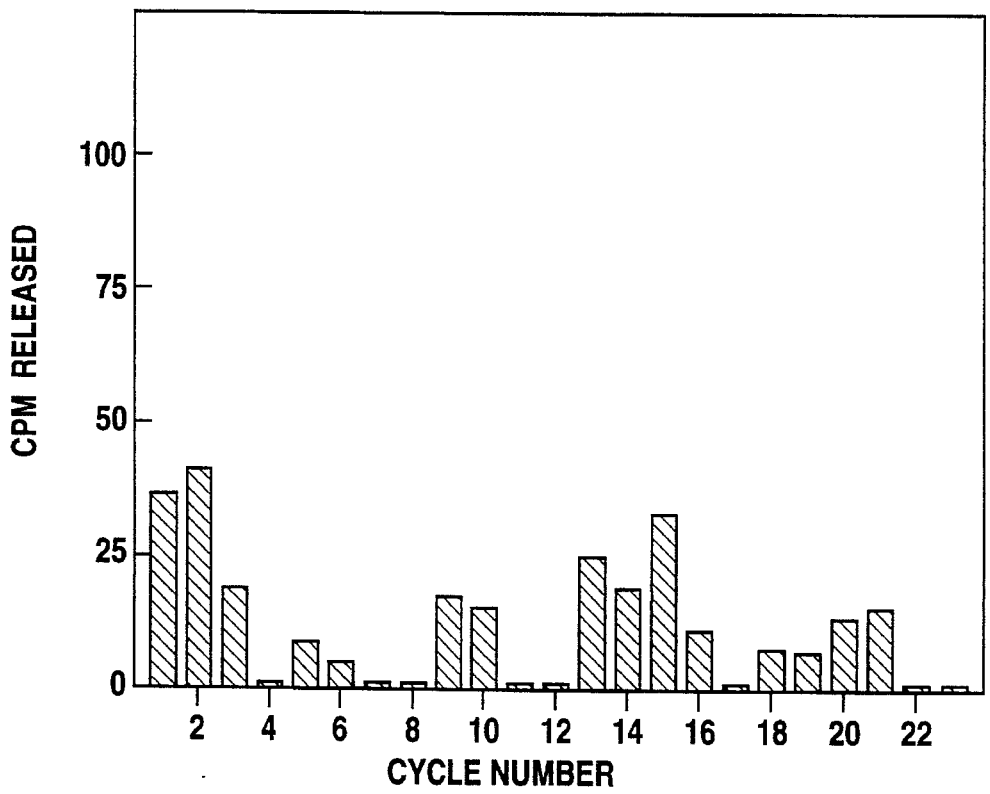

FIGS. 20A–20B. Radiosequence analysis of cathepsin G synthesized by U-937 cells cultured in the presence or absence of Gly—Phe—$CHN_2$. U-937 cell proteins were metabolically labeled with $^3$H-Ile as described herein in the presence (FIG. 20A) or absence (FIG. 20B) of Gly—Phe—$CHN_2$. After a 4 hour chase period, cells were disrupted and fractionated by aprotinin-agarose affinity chromatography. Unprocessed cathepsin G was further purified from the aprotinin unbound fraction by immunoadsoption with a rabbit anti-human cathepsin G antibody. The immunopurified proteins were subjected to Edman degradation and the position of Ile from the N-terminus determined by scintillation counting.

FIG. 21. Amino acid sequences of activation dipeptides of granule serine proteases synthesized by bone marrow derived cells. Amino acid sequences deduced from the cDNA's encoding human and murine granule serine proteases are shown with the predicted cleavage sites for the removal of each leader sequence and the activation dipeptide.

DETAILED DESCRIPTION OF THE PREFERRED EMBODIMENTS

The present invention discloses methods and compositions for inhibiting DPPI, as well as the pathologies which may subsequently be treated by eliminating DPPI mediated activation of particular cell types. The most preferred DPPI inhibitor of the invention is Gly—Phe—$CHN_2$.

The inventors disclose the isolation of the human DPPI protein, which has further enabled the determination of particular oligonucleotide sequences thereto, as well as the ability to isolate and further characterize the human DPPI gene. A cDNA for the human DPPI gene is also disclosed. Antisense oligonucleotides to human DPPI are proposed for potential use in the treatment of diseases found by the inventors to be related or consequent particular cell type activation by DPPI.

Methods of treating particular diseases, which the present inventors have found linked to the activity of the DPPI enzyme in particular cell types, include the use of both chemical inhibitors of DPPI and antisense oligonucleotides to the human DPPI gene, or a fragment thereof. These diseases include myeloid cell disorders, various inflammatory disorders, autoimmune diseases, graft rejection and graft-verses-host disease, to name a few. The specificity of action of the described inhibitors allow for normal functioning of non-threatening cell types while at the same time selectively inhibiting activation of particular cell enzyme pools involved in each of the above pathologial conditions.

The present invention also details specific methods for preparing the various DPPI inhibitors.

Cell Lines

U-937 (ATCC CRL1593) and P-815 (ATCC T1B64) cells were obtained from the American Type Culture Collection, Rockville, Md. and cultured in RPMI 1640 (Whittaker Bioproducts, Walkersville, Md.) supplemented with 10% fetal bovine serum (FBS, GIBCO BRL, Gaithersburg, Md., L-glutamine (0.3 mg/ml), penicillin G (200 U/ml) and gentamicin (10 µg/ml)).

Reagents

Rabbit antibodies to human leukocyte elastase and cathepsin G were purchased from Calbiochem. Protein-A-alkaline phosphatase conjugate was purchased from Cappel Worthington Biochemicals, Cooper Biomedical, Inc., Malvern, Pa.. Alkaline phosphatase substrates were purchased from Bio-Rad Inc., Richmond, Calif. Aprotinin-agarose, Percoll, buffer components and peptide substrates for assays of DPPI (Gly—Phe—βNA), leukocyte elastase (Suc—Ala—Ala—Ala—pNA), cathepsin G (Suc—Ala—Ala—Pro—Phe—pNA), and cathepsin H (Arg—βNA) were obtained from Sigma Chemical Co., St. Louis, Mo. Z—Arg—Arg—βNA, Z—Val—Leu—Arg—MNA and Gly—Phe—CHN$_2$ (catalog #DK-6)were purchased from Enzyme System Products, Dublin, Calif. BCA protein assay reagents were purchased from Pierce Chemical Co., Rockford, Ill. Minimal essential medium without isoleucine (MEM-Ile) was obtained from GIBCO BRL, Gaithersburg, Md. and prepared according to manufacturer's specifications.

Generation of Murine CD8(+) CTL

C57BL/6J (B6) and B6-C—H-2ml (bml) were purchased from The Jackson Laboratory, Bar Harbor, ME and bml×B6 F1 mice were produced in our animal care facility. Spleen cells from B6 female mice were treated with anti-CD4 (GK1.5, (Dialyras, et al. (1983) Immunol. Rev., 74:29.); 2B6, (Wassmer et al. (1985) J. Immunol. 135:2237), anti-NK (3A4, Sentman et al. (1989), J. Exp. Med., 170:191–202) and rabbit complement (Pel Freez, Rogers, Ark.) and then passed through nylon wool columns as previously described[2,3]. These CD8-enriched T-cells ($2\times10^6$/ml) were cultured for 5 days with irradiated (1,500 cGy) spleen cells from female bml or bml×B6 F1 mice ($2\times10^6$/ml) in RPMI 1640 supplemented with 10% FBS, 1 mM sodium pyruvate, $5\times10^{-6}$ M 2-mercaptoethanol, 5 mM Hepes, Penicillin G (200 U/ml), gentamicin (10 µg/ml), L-glutamine (0.3 mg/ml). At the onset of cultures and after 72 hours of culture, 1% phorbol dibutyrate-stimulated EL4 supernatant (produced as previously described and containing 200 u/ml IL2) was added as a source of supplemental cytokines.

Generation of Human Lymphokine Activated Killer Cells

Peripheral blood mononuclear cells were separated from heparinized venous blood of healthy donors by centrifugation on sodium diatrizoate/ficoll gradients (Sigma Chemical Co., St. Louis, Mo.). CD8(+) T-cell and NK-enriched lymphocytes were prepared bypassing peripheral blood mononuclear cells through nylon wood columns, incubation with OKT4 (anti-CD4) and L243 (anti-HLA-DR,) and panning on goat anti-mouse Ig-coated petri dishes as previously described[2]. CD8(+) T and NK-enriched cells ($5\times10^6$/ml) were then cultured in RPMI medium supplemented with 10% FBS and 100 U/ml recombinant IL2 (Cetus Corp., Emeryville, Calif.) for 48 hours.

Chronic Inhibition of Endogenous DPPI

Isolated cells or cell lines were cultured as described above in the presence or absence of 3 µM Gly—Phe—CHN$_2$ or equal concentrations of diluent (0.15% DMSO). In preliminary experiments, a single addition of 3 µM Gly—Phe—CHN$_2$ to long term cultures was found to lead to persistent >90% inhibition of DPPI activity. However, as recovery of DPPI was observed at time >72 hours after such additions, in longer term cultures, additional Gly—Phe—CHN$_2$ (3 µM) was added at 48–72 hour intervals to maintain continuous inhibition of DPPI.

Protease Assays

DPPI activity was assayed by the hydrolysis of Gly—Phe—βNA as previously described[4,5]. Macropain activity was assayed by the hydrolysis of Z—Val—Leu—Arg—MNA as previously described[66]. Cathepsin B activity was assayed by the hydrolysis of Z—Arg—Arg—βNA using the method of Barrett et al. ((1981) (Methods in Enzymology, 80:535–561). Cathepsin D activity was assayed by a modification of the assay of Takayuki and Tang using denatured hemoglobin as substrate (Barrett et al. (1981), In: Methods in Enzymology, edited by S. P. Colowick and L. Lorand, 80, p. 561 Academic Press, New York). Cathepsin G and elastase activities were assayed by the method of Baugh and Travis ((1976) Biochemistry, 15:836) with Suc—Ala—Ala—pNA and Suc—Ala—Ala—pNA, respectively. Cathepsin H activity was assayed by the hydrolysis of Arg—βNA by the method of Shaw et al. (Kirschke et al. (1987) Chemistry of lysosomal proteases, In:Lysosomes: Their Role in Protein Breakdown, edited by H. Glaumann and F. J. Ballard, p. 193, Academic Press, New York). Granzyme A and tryptase activities were measured by the hydrolysis of BLT substrate as previously described (Green et al. (1979) Anal. Biochem., 93:223)

Isolation of Cytoplasmic Granules from Cell Homogenates

Cells were incubated for 5 minutes on ice in hypotonic homogenization buffer (0.1× PBS salts, 1 mM MgCl$_2$). The cells were disrupted with a glass pestle homogenizer and isotonic conditions restored by the addition of 10× PBS salts. The homogenates were cleared of cell debris and intact cells by centrifugation at 600 xg for 2 minutes. The soluble extracts were layered on discontinuous Percoll gradients (6 ml 39%, 6 ml 90% Percoll) and centrifuged for one hour at 17,000 xg. The gradients were fractionated by removing 1 ml aliquots from the top.

Metabolic Labeling of Cathepsin G and Radiosequence Analysis

Protein labeling and sequencing were performed by a modification of the techniques described by Salvesen and Enghild[80]. Briefly, U-937 cells were harvested from culture and washed once with isoleucine-free MEM (MEM-Ile). Cells were resuspended in MEM-Ile at $5\times10^6$ cells/ml in the presence of 10 µM Gly—Phe—CHN$_2$ or diluent control (0.1% DMSO). After 1 hour of culture, cell aliquots were removed to assess DPPI activity and $^3$H-isoleucine, 0.5 mCi/ml, was added to the control and DPPI inhibited cultures. After an additional hour of culture with $^3$H-isoleucine, cells were washed and incubated for a 4 hour chase period at a density of $2\times10^6$ cells/ml in RPMI 1640 containing 10% bovine calf serum supplemented with 10µM Gly—Phe—CHN$_2$ or 0.1% DMSO as in initial cultures. Cells were harvested, washed with saline and stored at −70° C. Cells were disrupted by 2 freeze-thaw cycles and suspended in 50 mM Tris-HCl, pH 8.0, 1 M NaCl, 0.5% Triton X-100 at a ratio of $2\times10^6$ cells per ml. Active serine proteases were removed from the homogenates by adsorption to aprotinin-agarose (25 µl packed resin/ml homogenate). Inactive protease proteins were isolated from the aprotinin-agarose unbound fractions by immunoadsorption with anti-cathepsin G antibodies adsorbed to protein A-sepharose. Proteins bound to aprotinin-agarose were eluted in 50 mM sodium acetate, pH 4.0, 300 mM NaCl and further purified by immunoadsorption. Proteins specifically bound to either aprotinin-agarose or antibody-protein A-sepharose were eluted in SDS-PAGE sample buffer and analyzed by SDS-PAGE. The amino-terminal sequences of the isolated proteins were confirmed by radiosequence analysis. Immunopurified cathepsin G in SDS-PAGE sample buffer was spotted onto Immobilon paper (Millipore Corp., Bedford, Mass.) and processed for Edman degradation. The product of each sequencing cycle was collected and analyzed by scintillation counting.

Protein Purification

DPPI will be purified by the procedure developed in this laboratory (McGuire et al., submitted). Myeloid cell proteases will be purified the previous methods.[67,72,73] The proenzyme forms of these serine proteases will be purified from the aprotinin-agarose unbound fraction by isoelectric focusing. DPPI-inhibited U-937 cells will be homogenized and a granule fraction isolated by Percoll density gradient centrifugation. The Percoll will be removed by ultracentrifugation. The granules will be lysed and chromatographed on aprotinin-agarose. The unbound fraction of protein (devoid of serine protease activity but containing the proenzymes) will be fractionated in a preparative isoelectric focusing cell (Biorad's Rotofor IEF apparatus). The myeloid serine protease proenzymes are well resolved from the remaining granule proteins.

Isolation and Sequencing of the Carboxyl-Terminal Fragment of Human DPPI

To isolate the carboxyl-terminal portion of human DPPI, tryptic digests will be chromatographed on an anhydrotrypsin affinity matrix. All tryptic fragments with carboxyl-terminal arginine or lysine residues should bind to this affinity matrix. Only the carboxyl-terminus of the subunit should lack the basic residue for interacting with the matrix and, therefore, appear in the flow-through fraction from the column. If the human subunit has a carboxyl terminal basic residue the procedure would be performed with chymotrypsin and an anhydro-chymotrypsin affinity resin.

Vectors and Molecular Techniques

Several vectors will be used during the course of the present studies. The original cDNA libraries were prepared in lambda gt11. The cDNA's isolated from either library or prepared by PCR amplification will be ligated into pGEM3Zf or M13mp18 for the generation of single stranded DNA to be used for sequence analysis or mutagenesis. The pGEM vector contains sequences recognized by T7 and SP6 RNA polymerases and can be used for the synthesis of RNA in vitro. Transfection of Jurkat cell by electroporation[76] will make use of the pSV2neo vector or the pCB6 vector. The pCB6 vector was developed in the laboratory of Dr. David Russell of this institution. Eukaryotic cells transfected with either of these vectors can be selected by resistance to the antibiotic G418 due to the presence of the neo gene.[77] An SV40 promotor drives the synthesis of protein from the neo gene. Both vectors carry the pBR322 and SV40 origins of replication for replication in both prokaryotic and eukaryotic cells. These vectors have been used for production of both transient and stable transfected cells. The pCB6 vector uses the CMV promotor to drive the synthesis of the protein from the cloned cDNA inserted into a polylinker site. The vector also contains the human growth hormone termination and polyadenylation signals to insure the synthesis of mature transcripts.

Antisense oligonucleotide will be prepared synthetically and added directly to cells in culture as described previously (Bories et al. (1989) *Cell,* 59:959–968).

Even though the present invention has been described with a certain degree of particularity, it is evident that many alternatives, modifications, and variations will be apparent to those of skill in the art in light of the following disclosure. Accordingly, it is intended that all such alternatives, modifications, and variations which fall within the spirit and the scope of the invention be embraced by the defined claims.

The following examples are presented to describe preferred embodiments and utilities of the present invention, but should not be construed as limiting the claims thereof.

EXAMPLE 1

ISOLATION AND CHARACTERIZATION OF HUMAN DIPEPTIDYL PEPTIDASE-I (DPPI)

The present example is provided to demonstrate one preferred method for preparing the 1,000-fold purified preparation of human dipeptidyl peptidase-I from human tissue of the present invention. While the method may be employed to isolate human DPPI from any human organ or tissue which contains the DPPI enzyme, the tissue of preference is human spleen tissue.

Purification of DPPI

DPPI was purified to apparent homogeneity from human spleen by a combination of differential pH solubility, heat-treatment, affinity chromatography on Concanavalin A-agarose and p-hydroxymercuribenzoate-agarose, and gel filtration chromatography on Sephacryl S-300. The purification scheme developed in these studies is summarized in Table 3.

TABLE 3

| Purification of Human Dipeptidyl Peptidase-I | | | | |
|---|---|---|---|---|
| Step | Total Protein (mg) | Total Activity (nmol βNA/min) | Specific Activity (U/mg) | Yield (%) | Enrichment |
| Extract | 12000 | 38000 | 3 | 100 | 1 |
| Heat-treated/ pH adjusted | 9600 | 36000 | 4 | 93 | 1 |
| Concanavalin A-agarose | 89 | 19000 | 210 | 50 | 70 |
| pHMB-agarose | 6.7 | 7100 | 1100 | 19 | 370 |
| DEAE-Sephacel | 2.0 | 3700 | 1800 | 10 | 600 |
| Sephacryl S-300 | 0.2 | 640 | 3200 | 1.7 | 1100 |

Cadaveric spleen was collected within 12 hr. postmortem and stored at −70° C. until use. Approximately 200 g spleen was allowed to thaw and the tissue was trimmed of excess fat and minced in an acidic hypotonic homogenization buffer (10 mM sodium acetate-acetic acid, pH 4.0) The ratio of this buffer to tissue was 5 ml/g. The tissue was homogenized in an Oster blender at high speed for 15 s. The homogenate was centrifuged at 13,000 g for 20 min. The supernatant fluid was saved and the pellet was reextracted with the same buffer containing 0.1% Triton X-100 (2.5 ml/g). After centrifugation, the supernates were combined and heated to 55°–60° C. After 30 min, the extract was cooled to room temperature and adjusted to pH 7.5 with 1 M Tris base. Precipitate that formed during heating and pH adjustment was removed by filtration under gentle vacuum. The soluble sample was chromatographed on a concanavalin A-agarose column equilibrated with phosphate-buffered saline (PBS). The column was washed extensively with PBS before the elution of bound protein. Protein was eluted with 500 mM α-methylmannopyranoside in PBS. The eluted material from the concanavalin A-agarose was applied to a p-hydroxymercuribenzoate-agarose column equilibrated in PBS. After unbound protein was washed through the column, the column was washed extensively with 10 mM sodium phosphate, pH 7.0. A fraction of the bound protein was eluted in 10 mM sodium phosphate containing 50 mM β-mercaptoethanol. Other sulfhydryl-containing proteins were eluted in PBS containing 50 mM β-mercaptoethanol. Material from this second elution was diluted 5-fold with 10 mM sodium phosphate, pH 7.0, and chromatographed on a 1.5-ml DEAE-Sephacel column. Bound protein was eluted with 10× PBS and directly fractionated by chromatography on a Sephacryl S-300 gel filtration column equilibrated with 250 mM NaCl, 0.02% sodium azide. Gel filtration column fractions were monitored by SDS-PAGE using 15% polyacrylamide gels, in addition to assays of protein and dipeptidyl peptidase activity. This procedure yields approximately 100 μg of apparently homogeneous DPPI per 100 g tissue.

The total DPPI activity obtained after homogenization of spleen at neutral and acidic pH was found to be identical. However, since homogenization at neutral pH solubilized 2–2.5 times more protein than at pH 4, spleen was routinely homogenized in the acidic buffer. A second extraction of the insoluble material pelleted after acidic homogenization increased the level of total DPPI activity by up to 30% in various preparations.

Heat-treatment of tissue extracts at 60° C. for up to 45 min was found to have no apparent effect on DPPI activity. For enzyme purification, tissue extracts were routinely exposed to heat-treatment for 30 min. Since little visible precipitate formed during heat-treatment, the unfiltered extracts were adjusted to pH 7.5 by the addition of 1 M Tris base. Visible precipitate formed upon addition of Tris base and was removed by filtration under gentle vacuum. The combination of heat-treatment and pH adjustment results in the removal of approximately 25% of the original protein with a negligible loss of DPPI activity (Table 3).

The soluble protein fraction was loaded directly on a concanavalin A-agarose column. The vast majority of protein but no DPPI activity appeared in the flowthrough fractions. After extensive washing with PBS, bound protein was eluted by the addition of α-methylmannoside. Approximately 50% of the applied activity was recovered with a 70-fold increase in specific activity.

The material eluted from the lectin-affinity column was applied directly to a mercurial-affinity column. The majority of applied protein, but no DPPI activity, appeared in the flowthrough fraction. The column was washed extensively with PBS and then with 10 column volumes of 10 mM sodium phosphate, 1 mM EDTA, pH 7.0, to remove unbound protein. Bound protein was then eluted from the column in a two-step process. Washing the column with 50 mM β-mercaptoethanol eluted the majority of DPPI (Table 3).

Human DPPI eluted from the mercurial affinity chromatography was diluted with 5 vol of 10 mM sodium phosphate, 1 mM EDTA, pH 7.0, to decrease the ionic strength of the sample and chromatographed on a column of DEAE-Sephacel. DEAE-Sephacel chromatography resulted in an almost 2-fold increase in specific activity.

Previously published methods for the partial purification of DPPI have used Sephadex G-200 or Sephacryl S-200 for gel filtration chromatography. Neither of these gels yielded adequate resolution of DPPI from other high-molecular-weight proteins (data not shown). However, such resolution was achieved when DPPI was chromatographed on a Sephacryl S-300 gel filtration column. In the individual Sephacryl S-300 fractions, DPPI activity was correlated with the presence of a protein band determinated by SDS-PAGE corresponding to a molecular weight of 24,000.

Furthermore, in fractions corresponding to the peak of DPPI activity, this was the only protein band observed after SDS-PAGE. This protein band stained positively with periodic acid-Schiff's reagent, confirming the presence of carbohydrate. Polyacrylamide gel electrophoresis under nondenaturing conditions demonstrated a single protein band in the Sephacryl S-300 pool. After transfer of this protein to nitrocellulose, DPPI activity staining demonstrated that it was associated with the enzymatic activity. SDS-PAGE analysis of the protein band isolated in the nondenaturing gel system demonstrated a single 24,000 Da protein. The 24,000-Da protein was also correlated with DPPI activity by SDS-PAGE analysis of fractions obtained by preparative isoelectric focusing.

Comparison of the relative elution position of DPPI during gel filtration with proteins of known molecular weight indicated that DPPI had an estimated molecular mass of 200,000 Da. The elution position of DPPI was not altered by inclusion of 1M NaCl in the column buffer, suggesting that the high molecular weight of the enzyme is not the result of protein aggregation.

The purification scheme detailed here has resulted in a more than about 1000-fold purification of DPPI from the acidic extract of human spleen (Table 3). Approximately 100 μg of purified DPPI was obtained per 100 g wet wt of human tissue. Of note, tissue has been stored frozen for up to a year without noticeable loss of DPPI yield. Purified DPPI has also been stored frozen and at 4° C. for months with no significant loss of activity.

Since DPPI had not been purified previously, many of the properties of the enzyme were unclear or controversial. Particularly controversial from previous studies were the size and subunit composition of DPPI. Human DPPI is now established to constitute a 200,000 Da glycoprotein with 24,000 Da subunits. This human enzyme is further defined as having an isoelectric point of 5.4 and has been identified by the present inventors as being localized to the lysosomal/granule fraction of isolated cells. DPPI is a member of the cysteine class of peptide hydrolases and is inhibited by iodoacetate, mercurial, n-ethylmaleimide and cystatin. DPPI exhibits both peptidase and polymerase activity. Peptide hydrolysis is optimal at pH 5–6, and is generally measured by cleavage of the synthetic peptide, Gly—Phe—βNA. Peptide polymerization is optimal at pH 7–7.7. A novel assay for this activity, based on the lysis of red blood cells has also been developed by the present inventors using leu—leu—OMe as substrate.

Localization of DPPI Activity to Bone Marrow Derived Cells

Figure 1:
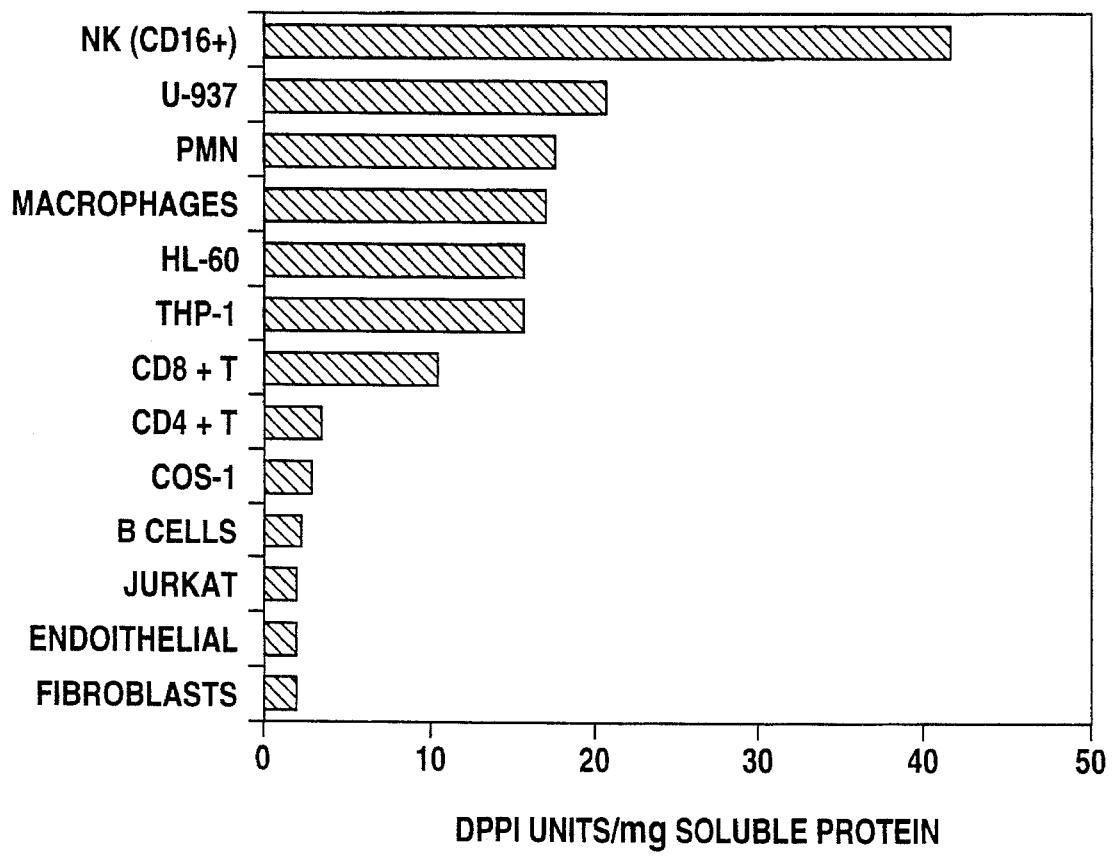
FIG. 1. DPPI activity in various cell types. The AMC= amino methyl coumarin dibutyrate stimulated EL4 cells activity of DPPI is based upon the hydrolysis of the synthetic AFC=aminofluorocoumarin peptide Gly—Phe—βNA.

DPPI is expressed at distinctly different levels in functional subsets of cells involved in the immune response. Based upon the hydrolysis of Gly—Phe—βNA, DPPI-like activity can be demonstrated in extracts of most mammalian cells. However, the level of enzyme expression in various cell types can vary by 20-fold or more. As seen in FIG. 1, the level of DPPI activity is considerably higher in natural killer cells, myeloid cells and CD8+ cytotoxic T-cells. These are the same cells that were shown to be susceptible to the toxic effects of Leu—Leu—OMe.[1-5] CD4+ T-cells, B-cells, and the T-lymphocyte line, Jurkat, express significantly lower levels of DPPI activity. COS-1 cells and other cells of non-bone marrow origin such as fibroblasts and endothelial cells have much lower levels of an apparent DPPI activity.

Amino Acid Sequencing of DPPI

DPPI purified from human spleen has been subjected to amino acid sequencing. The 24,000 molecular weight subunit isolated after SDS-PAGE described herein was used for this purpose. After resolution by SDS-PAGE, the subunit was transferred to PVDF-paper and subjected to N-terminal sequence analysis by Edman degradation. Based on the failure of N-terminal sequencing, the inventors concluded that the 24,000 Da sequence was chemically blocked. Therefore, the protein was digested with TPCK-treated trypsin or cyanogen bromide. The tryptic and cyanogen bromide peptides generated were isolated by reverse phase HPLC and analyzed by Edman degradation. The results are shown in Table 4. The letter "X" indicates the position of a residue unidentified by Edman sequencing.

TABLE 4

AMINO ACID SEQUENCES OF PEPTIDES ISOLATED FROM HUMAN DPPI

| PEPTIDE | AMINO ACID SEQUENCE |
| --- | --- |
| A | XLPTSXDVR |
| B | NVHGINFVSPVR |
| C | NQASCGSCYSFASMGMLEAR |
| D | IRILTXNSQTPILSPQEVVS |
| E | YAQDFGLVEEASFPYTXXD |
| F | YYSSEYHYVGGFYGGMNEALMK |
| G | LELVRHGPMAVAFEYVYD |
| H | GMLEARIR |
| I | AVAFEYVYDFLHY |

Based on a subunit molecular weight of 24,000, approximately 45% of the human DPPI subunit sequence has been determined at the amino acid level.

Most of the sequences obtained have not had significant homology to other sequences in the protein databases, except for 85% homology to the deduced sequence of rat DPPI and lesser homology to other members of the Papain family of cysteine proteases. Since only a tryptic digest of the human DPPI subunit has been analyzed, the relative positions of the sequenced peptides in the complete linear sequence of the subunit were unknown. The sequences obtained from the tryptic fragments of the human protein were aligned to the amino acid sequence deduced from the rat cDNA clone (see FIG. 2). The present inventors have found a greater than 85% identity at the protein level between the segments that have been sequenced. This identity includes the conserved region around the active site cysteine. Interestingly, this homology includes the tyrosine at position 29. This position is occupied by a tryptophan in every other member of the papain family sequenced to date. It has been suggested that this residue may play a role in substrate binding since DPPI is the only member of the papain family that is limited to exopeptidase activity.

The human sequence has not yet yielded a peptide sequence that matches anything in the carboxyl-terminal half of the rat protein. Many lysosomal enzymes are modified or processed at the carboxyl-terminus in vivo and this information is only revealed by studies at the protein level.

EXAMPLE 2

SUBSTRATE SPECIFICITY AND INHIBITORS OF HUMAN DIPEPTIDYL PEPTIDASE-I

The present example is provided to demonstrate the substrate specificity of human DPPI.

Isoelectric focusing in a gradient of pH from 3 to 10 resolved the DPPI activity into a single peak centered at pH 5.4. DPPI remained soluble at its isoelectric point and was enzymatically stable throughout the procedure.

The specificity of human DPPI was studied using a variety of synthetic peptide substrates. These substrates appear in Table 5.

TABLE 5

Substrate Specificity of Human DPPI

| | | Substrate peptide | | | Substrate concentration | |
| --- | --- | --- | --- | --- | --- | --- |
| $P_5$ | $P_4$ | $P_3$ | $P_2$ | $P_1$ | 100 μM | 500 μM |
| | | | | Ala- βNA | 0 | 0 |
| | | | | Arg- βNA | 0 | 0 |
| | | | | Gly- βNA | 0 | 0 |
| | | | | Leu- βNA | 0 | 0 |
| | | | | Phe- βNA | 0 | 0 |
| | | | | Pro- βNA | 0 | 0 |
| | | | CBZ- | Arg- βNA | 0 | 0 |
| | | | CBZ- | Phe- βNA | 0 | 0 |
| | | | Arg- | Arg- βNA | 0 | 0 |
| | | | Asp- | Ala- βNA | 250 | 1000 |
| | | | Gly- | Phe- βNA | 2380 | 4380 |
| | | | Gly- | Pro- βNA | 0 | 0 |
| | | | Ser- | Tyr- βNA | 1750 | 2000 |
| | | CBZ- | Arg- | Arg- βNA | 0 | 0 |
| | | | Gly- | Arg- MNA | 2500 | 4750 |
| | | | Gly- | Phe- MNA | 3500 | 5750 |
| | | | Gly- | Pro- MNA | 0 | 0 |
| | | | Ser- | Tyr- MNA | 1000 | 1750 |
| | CBZ- | Val- | Leu- | Arg- MNA | 0 | 0 |
| | | | Ala- | Ala- pNA | 380 | 1000 |
| | | | Gly- | Phe- pNA | 120 | 380 |
| | Suc- | Ala- | Ala- | Ala- pNA | 0 | 0 |
| | Ala- | Ala- | Val- | Ala- pNA | 120 | 120 |
| Suc- | Ala- | Ala- | Pro- | Phe- pNA | 0 | 0 |
| | | | CBZ- | Lys- AMC | 0 | 0 |
| | | | Gly- | Phe- AMC | 3500 | 6120 |
| | | Pro- | Phe- | Arg- AMC | 0 | 0 |
| | CBZ- | Gly- | Pro- | Arg- AMC | 0 | 0 |

Substrates with blocked amino-termini, with proline at the $P_1$ position, arginine at the $P_2$, or containing only single amino acids, were not hydrolyzed. DPPI was found to hydrolyze peptides with both polar and nonpolar side chains. The enzyme was able to hydrolyze an unblocked tetrapeptide nitroanilide but not a chemically blocked peptide substrates of similar composition. These results demonstrate that DPPI does not express endoproteolytic activity. Furthermore, purified DPPI did not exhibit endoproteolytic activity as assayed by the ability to generate acid soluble peptides from FITC-casein. The amino-terminal sequence of bovine α-casein, Arg—Pro, prohibits the processive cleavage of amino-terminal dipeptides from this protein and therefore should increase the ability to specifically detect endoproteolytic activity, if present.

Purified human DPPI was noted to hydrolyze fluorogenic peptides over a broad acidic pH range (FIG. 12). A similar pH profile was observed with each of the susceptible peptide substrates tested. Maximal peptidase activity occurs over the range of pH 4.5 to 6.8.

The inhibitor profile of human DPPI was found to be consistent with the classification of the enzyme as a cysteine peptidase (Table 6).

TABLE 6

Effect of Protease Inhibitors on DPPI Activity

| Inhibitor | Concentration | Percentage control activity |
| --- | --- | --- |
| PMSF | 1 mM | 98 |
| TLCK | 1 mM | 5 |
| TPCK | 1 mM | 10 |
| 1,10-Phenanthroline | 1 mM | 98 |
| Bestatin | 500 µg/ml | 103 |
| Cystatin | 50 µg/ml | 32 |
| N-Ethylmaleimide | 1 mM | 63 |
| Gly-Phe-diazomethane | 20 µM | 12 |
| Iodoacetic acid | 1 mM | 10 |
| Mersalyl acid | 1 mM | 3 |
| 2,2'-Dithiodipyridine | 400 µM | 9 |

Note. Purified human dipeptidyl peptidase-I (0.4 µg) was preincubated with each of the inhibitors at the stated concentration for 15 min at 37° C.. Each sample was diluted 3-fold with assay buffer containing substrate and incubated for an additional 20 min.

Thus, DPPI activity was potently inhibited by mersalyl acid, iodoacetic acid, and cystatin. Furthermore, DPPI activity was inhibited by dithiodipyridine at low pH. Under these conditions, this reagent is considered a specific inhibitor of enzymes with active site cysteine residues. DPPI activity was also inhibited by N-ethylmaleimide. However, under the conditions used for screening inhibitors (pH 5.5) the effect of N-ethylmaleimide was not complete.

At pH values above 6.5, the potency of this inhibitor increased as expected. Human DPPI activity was also potently inhibited by Gly—Phe—diazomethane, an inhibitor specifically designed for this activity. Surprisingly, DPPI was also potently inhibited by both TLCK and TPCK. While these inhibitors affect a variety of serine and cysteine peptidases, including papain, they have not been reported to be inhibitors of DPPI previously. Based on the substrate requirements for an unblocked amino-terminus and dipeptide length, inhibition of DPPI by TLCK and TPCK was unexpected. The general serine peptidase inhibitor PMSF, the aminopeptidase inhibitor bestatin, and metal chelators had no effect on DPPI activity.

EXAMPLE 3

HUMAN DPPI AND POST-TRANSLATIONAL PROCESSING OF MYELOID SERINE PROTEASES

The present example is provided to demonstrate the utility of DPPI-inhibitors, such as Gly—Phe—$CHN_2$, for inhibiting the activity of DPPI in cells. An in vitro system is employed as a model in the example. However, similar specificity of action is expected for cells in an in vivo system as well.

The Gly—Phe—$CHN_2$ was obtained from Enzyme System Products (catalog #DK-6) in Dublin, Calif. U-937 cells were obtained from a publicly available ATCC deposit, ATCC CRL1593, which is a human histiocytic lymphoma. HL60 (ATCC CCL240) and THP-1 (ATCC TIB202) cell lines were also obtained from the ATCC and are publicly available cell lines.

Inhibition of DPPI by Gly—Phe—$CHN_2$

In order to verify the specificity of inhibition of DPPI in cultured cells exposed to Gly—Phe—$CHN_2$, U-937 cells were cultured in the presence of 3 µM Gly—Phe—$CHN_2$ or diluent (0.15% DMSO, control) for one hour. A cell extract was prepared and assayed for the activity of both cytoplasmic and lysosomal/granule protease activities. The results shown in FIG. 3 are expressed as the relative specific activity of each protease in extracts of cells exposed to Gly—Phe—$CHN_2$ compared to those cultured with DMSO only. While DPPI activity was inhibited more than 90%, other proteases were largely unaffected. Specifically, cathepsin B, another lysosomal thiol protease, retained approximately 80% of the control activity. No inhibition of other thiol proteases, including cathepsin H and the cytoplasmic protease, macropain, was observed. Furthermore, the activities of cathepsins D and G as well as elastase were not directly inhibited by short term exposure to Gly—Phe—$CHN_2$. Studies by the inventors also demonstrate that the inhibitor does not affect the integrity of the granules. These results demonstrate that Gly—Phe—$CHN_2$ specifically inhibits DPPI while sparing the activity of other intracellular enzymes.

Myeloid Serine Protease Zymogen Activation Inhibited as a Result of DPPI Inhibition In additional experiments, U-937 cells were incubated for 48 hours in the presence or absence of 3 µM Gly—Phe—$CHN_2$. DPPI activity was decreased by an average of 95% in cells exposed to the diazomethane inhibitor. While the activities of cathepsin B, D, H, and macropain were 90–106% of control levels, the activities of elastase and cathepsin G were decreased approximately 65% in cells that received the Gly—Phe—$CHN_2$ for 48 hours (FIG. 4).

In contrast to the decrease in enzymatic activity, Western Blot analysis of granules isolated from DPPI-inhibited cells by homogenization and Percoll gradient fractionation, demonstrated similar quantities of immunoreactive cathepsin G and elastase antigen. These results show that in U-937 cells with diminished DPPI activity, serine proteases accumulate as inactive proenzymes. Thus, these results demonstrate that DPPI is the principal enzyme responsible for processing and activation of the serine proteases in bone marrow derived cells.

DPPI Inhibition and Myeloid Cell Growth and Proliferation

While Gly—Phe—$CHN_2$ has no discernible effect on U-937 cell proliferation during the first 48 hours after addition to culture, profound effects on cell growth are seen in longer term cultures. Thus, as shown in FIG. 5, cumulative proliferation of U-937 cells cultured for four days with 3 µM Gly—Phe—$CHN_2$ was decreased by 60% (right panel) while $^3$H-thymidine incorporation measured during the last 8 hours of such cultures was reduced by greater than 90%. The effects of this DPPI inhibitor on proliferation of the HL60 myeloid cell line were even more profound with virtually no viable cells recovered at the end of 4 days of culture with Gly—Phe—$CHN_2$ (see FIG. 5).

In contrast, proliferation of another myeloid tumor cell line, THP-1, was not affected by incubation with an identical concentration of the DPPI inhibitor.

Cell division in the relatively undifferentiated myeloid cell line, HL60, has been shown to require the functional expression of myeloblastin[123]. Myeloblastin mRNA and enzymatic activity have been demonstrated in U-937 cells[123]. Myeloblastin is a member of the bone marrow serine protease family and has a putative activation dipeptide that is a suitable substrate for DPPI, and therefore, the observed effect of the DPPI inhibitor on U-937 cell division is consistent with a role for DPPI in the processing and activation of myeloblastin as well as elastase and cathepsin G in U-937 cells.

Inhibition of DPPI Affects Differentiation

U-937 cells continuously exposed to the DPPI inhibitor also acquire characteristics of differentiation along the monocyte lineage. In the experiment detailed in FIG. 6, U-937 and THP-1 cells were cultured for four days in the presence or absence of 3 µM Gly—Phe—$CHN_2$ and assayed for cell surface expression of myelomonocytic markers, including CD14, CD11b (Type III complement receptor, CR3) and Class I MHC antigens. Fluorescent goat anti-mouse IgG was used to counterstain cells after incubation with murine monoclonal antibodies directed against the indicated cell membrane antigens or with an irrelevant control monoclonal antibody, P117. The expression of the antigen was assessed by fluorescence activated flow cytometric techniques (an excitation of 485n.m.±10 and employing a wavelength of 530±15). As shown in the right hand panels, THP-1 cells cultured under control conditions express the mature myelomonocytic phenotype. They express both CD14 and CD11b and Class I MHC antigens. Culture with Gly—Phe—$CHN_2$ had no effect on the expression of these antigens in THP-1 cells. In contrast, U-937 cells incubated under control conditions expressed a less mature phenotype. As shown in the upper left panel, U-937 cells did not express CD14 or CD11b and expressed low levels of Class I MHC antigen. However, as shown in the lower left panel, after four days in the presence of Gly—Phe—$CHN_2$, U-937 cells expressed CD11b (CR3) and increased levels of Class I MHC antigens. This effect of the DPPI inhibitor is also consistent with the proposed role of DPPI in the processing and activation of the myeloblastin, as myeloid tumor cells cultured with antisense oligonucleotides to DPPI inhibit myeloblastin synthesis undergo similar differentiation.

Of note, only partial inhibition of serine protease activity in the U-937 cells treated with the DPPI inhibitor has been observed in the study detailed in FIG. 5, above. This partial inhibition may have several explanations. The inventors have noted that when U-937 cells were pre-treated with the serine protease inhibitor, PMSF, and ammonium chloride prior to culture in the presence or absence of Gly—Phe—$CHN_2$, greater than 80% reduction in generation of newly synthesized cathepsin G and elastase was observed in cultures containing the DPPI inhibitor. The presence of residual serine protease activity in DPPI inhibited cells would be expected if other mechanisms for the removal of the activation dipeptide were available in the cells. Alternatively, the unprocessed precursors of cathepsin G and elastase may mediate low levels of serine esterase activity in assays employing synthetic peptide substrates.

As demonstrated by the results of the study detailed in FIG. 7 the apparent inhibition of serine protease activity in Gly—Phe—$CHN_2$-treated cells is higher when assayed by hydrolysis of the protein substrate, casein, relative to effects observed with assays using synthetic peptide substrates. The results obtained support that DPPI plays a requisite role in the processing and activation of the myeloid granule serine proteases.

EXAMPLE 4

IN VIVO EFFECT OF INHIBITOR
Gly—Phe—$CHN_2$

The present example is provided to demonstrate the utility of using dipeptidyl peptidase-I inhibitors for the in vivo treatment of DPPI-mediated diseases, particularly inflammatory diseases and those pathologies involving cells of myeloid origin. By way of example, such conditions include the treatment of graft versus host disease (GVHD) allograft rejection, malignancies of myeloid cell origin, such as leukemia in an animal, particularly in humans.

Dose Response In Vivo to DPPI-Inhibitors

Three groups (N=6) of B6×CBA F1 mice were injected intraperitoneally with one of three doses of Gly—Phe—$CHN_2$, 0.5 µg/g, 1.5 µg/g or 5 µg/g. At the end of 3 hours, one-half of the animals from each group were sacrificed and the spleen from each animal dissected. Spenic DPPI activity was measured for each tissue.

At the end of 24 hours post injection, the remaining one-half of the animals from each treatment group were sacrificed and the spleen from each animal harvested. Splenic DPPI activity was measured for each of those animals as well.

As shown by results detailed in FIG. 9, single intraperitoneal injections of 1.5 or 5 µg/g of Gly—Phe—$CHN_2$ (obtained from Enzyme Systems Products, Livermore, Calif.) resulted in 90% inhibition of DPPI within murine SpC harvested 3 hours later.

Recipients of a lower dose (0.5 µg/g) of this irreversible inhibitor regenerated significant levels of DPPI within 24 hours after injection. However, following higher doses (5 µg/g), the in vivo half-life of this inhibitor appeared sufficient to maintain 90% inhibition of this enzyme.

Selectivity of Inhibition of DPPI In Vivo

In the experiment detailed in Table 7, individual B6×CBA F1 mice were injected intraperitoneally with either 1.5 µg Gly—Phe—$CHN_2$/gram body weight or with vehicle control (0.5% DMSO in saline). The Yac-1 represents a standard target for natural killer (NK) cells.

TABLE 7

IN VIVO ADMINISTRATION OF THE DIPEPTIDYL PEPTIDASE-I (DPPI) INHIBITOR, GLY-PRE-$CHN_2$ SELECTIVELY INHIBITS DPPI IN MURINE SPLEEN CELLS AND PREVENTS LEU-LEU-OME-MEDIATED DEPLETION OF NK CELLS AND CTL PRECURSORS

| Intraperitoneal Injection | Thiol Protease Activity (AFU/µg Protein) | | Leu-Leu-Ome Treatment | NK Function % Specific Lysis Yac-1 | | MLC Activated Anti-H-2° Spec. CTL | |
|---|---|---|---|---|---|---|---|
| | DPPI | Cath.B | | 20:1 | 80:1 | 20:1 | 80:1 |
| saline | 294 | 382 | Nil | 10 | 15 | 69 | 78 |
| | | | 250 µM | <1 | <1 | 1 | 3 |
| 1.5 µg/g Gly-Phe-$CHN_2$ | 12 | 419 | Nil | 11 | 19 | 69 | 85 |
| | | | 250 µM | 10 | 19 | 58 | 79 |

As shown by the results depicted in table 7, in vivo administration of Gly—Phe—CHN$_2$ resulted in 95% inhibition of splenic DPPI activity (12/294=4.1%) without altering the activity of another lysosomal thiol protease, cathepsin B.

The results also importantly demonstrate that Gly—Phe—CHN$_2$ employed in vivo also prevents Leu—Leu—OMe mediated depletion of NK cells and CTL precursors.

EXAMPLE 5

ROLE OF DPPI FUNCTION IN GENERATING CYTOLYTIC ACTIVITY

Unlike control cells, spleen cells in which DPPI activity was inhibited were resistant to any discernible toxic effects of Leu—Leu—OMe on NK function of the capacity to generate anti-H-2$^d$ specific CTL. In the present example and in studies performed with human PBL, inhibition of DPPI activity by preincubation with Gly—Phe—CHN$_2$ does not impair cytotoxic activity of NK cells when examined immediately after exposure to this inhibitor, nor does a brief exposure of this inhibitor significantly impair subsequent generation of cytotoxic activity. However, when assessed at the end of 5 day MLC, similar, high levels of DPPI were found to be regenerated within lymphocytes derived from precursors derived from SpC exposed in vivo to Gly—Phe—CHN$_2$. These results indicated that DPPI activity was induced during MLC.

Continuous DPPI inhibition during in vitro MLC was examined to determine the effect on the generation of CTL.

When the irreversible DPPI inhibitor Gly—Phe—CHN$_2$ ($3\times10^{-6}$M) was added directly to MLC at onset and again after 48 hours, continuous inhibition of the activity of DPPI was noted and, as demonstrated by results of the study detailed in Table 8, a reduction in the allospecific cytotoxicity generated in such cultures was noted.

TABLE 8

INHIBITION OF DPPI ACTIVITY DURING MIXED LYMPHOCYTE CULTURE IMPAIRS GENERATION OF CTL ACTIVITY

| Study | Addition to Culture | | Allospecific CTL | | |
|---|---|---|---|---|---|
| | Gly-Phe-CHN$_2$ | EL$^4$ Supernatant | 2.5:1 | 10:1 | 40:1 |
| 1 | – | – | 18 | 34 | 52 |
| | + | – | 1 | 1 | 9 |
| | – | + | 24 | 47 | 65 |
| | + | + | 3 | 8 | 18 |
| 2 | – | – | 4 | 11 | 22 |
| | + | – | 2 | 1 | 2 |
| | – | + | 0 | 21 | 41 |
| | + | + | 6 | 14 | 34 |
| 3 | – | + | 7 | 21 | 40 |
| | + | + | <1 | 5 | 19 |

However, some detectable CTL activity was still noted in assays performed at higher ET ratios. Moreover, when exogenous cytokines from phorbol dibutyrate stimulated EL4 cells were added to MLC containing Gly—Phe—CHN$_2$, the level of cytotoxicity generated was increased further. However, as shown by the results of the representative experiment detailed in FIG. 10, when cells were harvested 24 hours before CTL assay, extensively washed and placed into cultures free of Gly—Phe—CHN$_2$, both DPPI activity and CTL activity returned to levels similar to that seen with control MLC activated CTL cultured in this manner, indicating that upon recovery of DPPI function, cytolytic activity can be rapidly generated.

DPPI is therefore unlikely to be directly involved in target cell lysis mediated by cytotoxic lymphocytes. However, DPPI activity appears to be required for generating some aspects of CTL effector function. In considering the potential role of DPPI in generating the effector mechanisms previously suggested to play a role in CTL function, it became apparent that dipeptides separating putative signal sequences from the amino terminus of mature enzymatically active forms of each of the granzymes[19,62] were in every case known substrates of DPPI. These dipeptides are absent from granzymes isolated from activated CTL.[19,62]

To assess whether DPPI and granzyme A (BLT esterase) are coexpressed in the granules of activated cytotoxic lymphocytes, human peripheral blood lymphocytes (PBL) were cultured for 4 days with 50 µ/ml rIL2. The cells were then harvested, disrupted in a dounce homogenizer, the nuclei pelleted and residual intact cells removed by centrifugation and the granule fraction localized on discontinuous Percoll gradients. As shown in FIG. 11, granzyme A (BLT esterase) activity and DPPI activity co-isolated in the same granular fraction within these lymphokine activated cells. Of note, however, such BLT esterase activity could not be detected within IL2 activated Leu—Leu—OMe treated PBL. Thus, Leu—Leu—OMe sensitive, DPPI enriched cells are the source of BLT esterase in such IL2 activated cultures.

To assess the role of DPPI in generating BLT esterase activity in murine CTL, anti-CD4 and 3A4 (61, anti-NK)+C treated, nylon wool nonadherent B6 SPC were cultured for 5 days with irradiated anti-Thy1+C treated bml SpC and supplemental lymphokines (phorbol stimulated DL4 supernatant, 2% v/v) in the presence or absence of the DPPI inhibitor, Gly—Phe—CHN$_2$. Cells were disrupted and the granule fractions were isolated on discontinuous percoll gradients. The amount of granule associated BLT esterase activity within CD8(+) murine T-cells activated in the presence of continuous DPPI inhibition with Gly—Phe—CHN$_2$ also was found to be dramatically decreased (FIG. 16).

These results demonstrate the direct effect of DPPI on BLT esterase activity, and how BLT esterase activity may be specifically inhibited through the use of DPPI inhibitors, such as Gly—Phe—CHN$_2$.

EXAMPLE 6

EFFECT OF Gly—Phe—CHN$_2$ ON CULTURED CYTOTOXIC LYMPHOCYTES

The studies detailed in Table 10 were designed to evaluate the effects of chronic exposure to Gly—Phe—CHN$_2$ on other enzymatic activities expressed by cytotoxic lymphocytes (CTL). CD8(+) T cell-enriched B6 spleen cells were cultured with H-2K$^{bm1}$ disparate stimulator cells and supplemental cytokines in the presence or absence of 3 µM Gly—Phe—CHN$_2$.

BLT esterase activity was assessed as described herein. Cultures of SpC cells were prepared and maintained as also described herein. Gly—Phe—CHN$_2$ was obtained from Enzyme Systems Products.

The results from this study are provided in Table 9.

TABLE 9

GENERATION OF BLT ESTERASE ACTIVITY IS SELECTIVELY
IMPAIRED IN ALLOREACTIVE CD8(+) T-CELLS ACTIVATED
IN THE PRESENCE OF THE DPPI INHIBITOR GLY-PHE-CHN$_2$

| Expt. | Gly-Phe-CHN$_2$ Addition* | DPPI Activity[+] | Cathepsin B Activity[+] | Macropain Activity[+] | DPP IV Activity[+] | BLT Esterase Activity[J] |
|---|---|---|---|---|---|---|
| 1 | − | 34 | 57 | 7.4 | 2400 | 15.6 |
|   | + | 1  | 45 | 7.2 | 2450 | 3.3  |
| 2 | − | 44 | 92 | 9.7 | 1620 | 12.4 |
|   | + | <1 | 92 | 8.8 | 1900 | 3.2  |

*Cultures containing CD8(+) T-cell enriched B6 responder SpC and irradiated Class MHC disparate B6 X bml F1 stimulator SpC were supplemented with 3 × 10$^{-6}$ M Gly-Phe-CHN$_2$ or diluent control (0.15% DMSO) at onset and after 72 hours of culture.
[+]Activity expressed as nanomoles β-naphthylamine released per minute per 10$^7$ cells.
[J]Activity expressed as Δabsorbance$_{410}$/hour/10$^6$ cells.

These results demonstrate that DPPI activity can be chronically inhibited in cultured cells without diminishing the activities of other thiol proteases, such as the lysosomal enzyme cathepsin B or the cytosolic protease macropain. Similarly, DPP IV serine protease activity, associated with the T-cell surface activation antigen CD26, See Vivler, J. D. et al. (1991) J. Immunol. 147:447 for description of CD26 antigen) was not impaired in cultures containing the DPPI inhibitor, Gly—Phe—CHN$_2$. However, a selective reduction of BLT esterase activity in CD8(+) CTL generated in the presence of this DPPI inhibitor was observed.

That gly—phe—CHN$_2$ had no direct effect on BLT esterase was demonstrated by the results of experiments detailed in FIG. 15. Thus, addition of gly—phe—CHN$_2$, one hour before harvest of alloantigen reactive CD8(+) T cells (at hour 119 in 120 hour MLC, bottom left panel of figure) had no effect on BLT esterase activity despite efficient inhibition of DPPI. Rather, the decrease in BLT esterase activity was only observed when the DPPI inhibitor was present for more prolonged intervals during culture. While the greatest impairment of BLT esterase generation was noted when gly—phe—CHN$_2$ was present for the last 72 hours or throughout 5 day alloantigen stimulated cultures, a significant reduction in BLT esterase activity was observed even when DPPI was inhibited during only the last 24–48 hours of culture. Recent studies have shown that mRNA encoding granzyme A, the predominant lymphocyte granule enzyme associated with BLT esterase activity, is only detected during the last 72 hours of 5 day murine MLC (34). Thus, the same time period that DPPI inhibition has the most profound effect on the generation of BLT esterase activity appeared to coincide with the time of anticipated synthesis of granzyme A in alloantigen-activated CD8(+) T cells.

The granule serine proteases, granzyme A, has been reported to be the predominate lymphocyte enzyme associated with BLT esterase activity. To verify that generation of granule serine protease activity was indeed impaired during inhibition of DPPI, studies were performed to assess the localization of BLT esterase activity in different subcellular fractions of CD8(+) CTL activated in the presence or absence of Gly—Phe—CHN$_2$.

Alloreactive CD8(+) T-cells were homogenized and fractionated on discontinuous Percoll gradients. CD8(+) CTL incubated in the presence of Gly—Phe—CHN$_2$ were virtually devoid of DPPI activity while in control cells this enzymatic activity co-localized with the major peak of BLT esterase activity in the granule fractions of the Percoll gradient. As demonstrated in FIG. 16, CD8(+) CTL activated in control cultures (open circle, o) exhibited a peak of BLT esterase activity in the granule fraction that was largely absent from CD8(+) T-cells activated in the presence of the DPPI inhibitor Gly—Phe—CHN$_2$ (closed circle, ●). BLT esterase activity in the granule fractions of control cells was inhibited by >95% after in vitro incubation with 1 mM PMSF, but was not affected by 10$^{-5}$ M Gly—Phe—CHN$_2$. Thus, these observations suggest that chronic inhibition of DPPI activity during generation of CTL resulted in decreased levels of granzyme A activity within cytolytic granules.

EXAMPLE 7

CONTINUOUS DPPI INHIBITION AND SERINE
PROTEASE ACTIVITY IN CELLS OF BONE
MARROW ORIGIN

To even further define the possible role of DPPI in the processing and activation of bone marrow serine proteases, representative cell types including human LAK cells, a murine mastocytoma cell line (P-815 cells) and a human myelomonocytic cell line (U-937) were cultured in the presence or absence of 3 μM Gly—Phe—CHN$_2$ and assayed for the effect on the generation of granule protease activities. These cell lines were obtained from publicly available cell line deposits at the ATCC.

Cells were homogenized, fractionated on Percoll gradients and the fractions were assayed for activity of DPPI as described and the specific granule-associated serine proteases synthesized by each cell type. Chronic inhibition of endogenous DPPI was associated with significant decreases in the activities of the known granule-associated serine proteases from each cell type (FIG. 17). Thus, in human LAK cells, granzyme A activity (BLT esterase) was reduced up to 90% (FIG. 17, Panel A). The activity of tryptase was reduced to a similar extent after inhibition of DPPI activity in P-815 cells (FIG. 17, Panel B). Furthermore, in U-937 cells the activities of both elastase and cathepsin G were significantly reduced in cells exposed to the DPPI inhibitor for 48 hours (FIG. 17, Panels C and D).

In control cultures of each cell type, DPPI activity co-localized with the granule serine protease. Chronic inhibition of endogenous DPPI was associated with significant decreases in the activities of the known granule-associated serine proteases from each cell type (FIG. 17). Thus, in human LAK cells, granule BLT esterase (granzyme A) activity was reduced significantly (FIG. 17, Panel A). the activity of tryptase was reduced to a similar extent after inhibition of DPPI activity in P815 cells (FIG. 17, Panel B). Finally, in U-937 cells the activities of both elastase (FIG. 17, Panel C) and cathepsin G (FIG. 17, Panel D) were significantly reduced in cells exposed to the DPPI inhibitor for 48 hours. As observed with the murine CD8(+) T cells, incubation of the human LAK cells, U-937 cells or P185 cells for 1 hour in the presence of gly—phe—$CHN_2$ had no effect on serine protease activity while inhibiting DPPI activity 95–98%. Thus, in distinct bone marrow derived cell lineages, extended inhibition of endogenous DPPI was associated with selective reduction of the granule associated serine protease activities.

To verify the specificity of the DPPI inhibitor, Gly—Phe—$CHN_2$, in myeloid cells, the study detailed in FIG. 18 was performed. Incubation of U-937 cells in the presence of 3 μM Gly—Phe—$CHN_2$ for 1 or 48 hours was found to lead to 90–99% inhibition of the DPPI activity. The activities of all other proteases examined were largely unchanged after exposure to this inhibitor for 1 hour (FIG. 18, Panel A). Specifically, the activities of elastase, cathepsin G, cathepsin B, D and H, and macropain were not found to be decreased directly by this diazomethane inhibitor. The activity of cathepsin B remained greater than 80% of control levels, while the activities of macropain and lysosomal cathepsins D and H were unchanged following 48 hour exposure to Gly—Phe—$CHN_2$ (FIG. 18, Panel B). In contrast to these results, incubation of U-937 cells for 48 hours in the presence of 3 μM Gly—Phe—$CHN_2$ resulted in a 65% reduction in granule associated elastase and cathepsin G activities (FIG. 18, Panel B) in these cells. These data suggested that the effect of Gly—Phe—$CHN_2$ was specific for direct inhibition of endogenous DPPI and an indirect reduction in generation of granule serine protease activity within the cells.

Immunoblot analysis of granule fractions from U-937 cells demonstrated equivalent cathepsin G in samples prepared from control and DPPI-inhibited cells (FIG. 19). However, cathepsin G enzymatic activity was reduced by >65% in the granule fraction of U-937 cells cultured in the presence of Gly—Phe—$CHN_2$. These results, therefore, demonstrate that reduced expression of cathepsin G activity in U-937 cells was not the result of decreased protease synthesis, but rather was associated with the presence of immunoreactive but enzymatically inactive cathepsin G in the granules of these DPPI inhibited cells.

EXAMPLE 8

THE EFFECT OF INHIBITION OF INTRACELLULAR DPPI ON THE PROCESSING OF CATHEPSIN G IN U-937 CELLS

To examine the potential role of DPPI in pro-enzyme activation, proteins were metabolically labeled by culturing U-937 cells in the presence of [$^3$H]isoleucine in the presence of 3 μM Gly—Phe—$CHN_2$. Since isoleucine occupies the first two residues of mature cathepsin G but is not present in the pro-dipeptide, the form of cathepsin G isolated after inhibition of endogenous DPPI can be distinguished by radiosequence analysis. After the labeling period, the cells were cultured for up to 4 hours in the continuous presence or absence of the DPPI inhibitor to allow for endogenous processing of newly synthesized cathepsin G. At the end of this chase period, cells were disrupted and assayed for the presence of unprocessed and mature forms of cathepsin G. The unprocessed form of cathepsin G was separated from the enzymatically active, mature protease by aprotinin-agarose affinity chromatography. Both active and inactive forms of cathepsin G were further purified by immunoaffinity using specific antibodies adsorbed to protein A-Sepharose. At the end of the 4 hour chase period, cells exposed to the DPPI inhibitor (Gly—Phe—$CHN_2$) had accumulated less than 10% of the level of newly synthesized, active cathepsin G present in the control U-937 cells (Table 10).

TABLE 10

EFFECT OF Gly-Phe-$CHN_2$ ON THE ACCUMULATION OF UNPROCESSED INACTIVE CATERPSIN G IN U-937 CELLS

| SAMPLE | APROTININ-AGAROSE BOUND cpm (% total) | APROTININ-AGAROSE UNBOUND cpm (% total) |
|---|---|---|
| CONTROL | 22,900 (48%) | 24,400 (52%) |
| + Gly-Phe-$CHN_2$ | 2,385 (4%) | 57,300 (96%) |

U-937 cell proteins were labeled by incorporation of $^3$H-isoleucine in the presence or absence of Gly-Phe-$CHN_2$ an detailed in Methods. After a 4 hour chase period in the absence of $^3$H-isoleucine, cell extracts were prepared and incubated with the serine protease affinity matrix, aprotinin-agarose. Cathepsin G-immunoreactive protein was further purified from the aprotinin-agarose bound and eluted or unbound fractions by immunoadsorption. The results are given an cpm in each fraction and as % of the total cathepsin G-immunoreactive cpm in the control or DPPI inhibited cell extract. The aprotinin-agarose unbound, anti-cathepsin G immunopurified protein were subjected to Edman degradation and radiosequence determination (FIG. 20).

While a major fraction of the cathepsin G synthesized in control cells bound to the aprotinin-agarose, virtually all of the cathepsin G synthesized in the presence of the DPPI inhibitor did not bind to this affinity resin. The results shown in FIG. 20 demonstrate the accumulation of the propeptide-bearing form of cathepsin G (incapable of binding aprotinin-agarose) only in cells treated with Gly—Phe—$CHN_2$. Thus, direct protein radiosequence determination of the aprotinin-agarose unbound, immunoaffinity-purified cathepsin G demonstrated the presence of $^3$H-isoleucine in the third and fourth sequencing cycles (FIG. 20) indicating that the cathepsin G protein isolated from DPPI-inhibited cells still had the N-terminal activation dipeptide. The small amount of cathepsin G isolated in parallel from the aprotinin-agarose unbound fraction of control cultures contained isoleucine in the first and second sequencing cycles. This data demonstrates that all of the serine protease synthesized in the control cells had been processed to the active form. Thus, these results demonstrate the accumulation of the inactive proenzyme form of cathepsin G in cells devoid of DPPI activity.

EXAMPLE 9

THE EFFECT OF ACTIVATION DIPEPTIDE ON THE ACTIVITY OF HUMAN CATHEPSIN G

On the basis of the results detailed in FIG. 20, the inventors sought to determine if U-937 cells chronically incubated in the presence of Gly—Phe—$CHN_2$ would be devoid of cathepsin G and elastases activity. However, as demonstrated previously, U-937 cells cultured in the presence of the DPPI inhibitor for 48 hours express approximately one-third of the level of serine protease activity of control cells when assayed with synthetic peptide substrate. This low level of proteolytic activity was observed even when U-937 cells were treated with PMSF prior to initiation of cultures with the DPPI inhibitor to prevent the carryover of active enzymes synthesized prior to DPPI inhibition.

The experiments detailed in FIG. 7 were designed to assess effects of DPPI inhibition during granule serine protease generation on endoproteolytic activity based on the hydrolysis of casein to acid-soluble fragments.

These studies demonstrate a more pronounced effect of DPPI inhibition on granule serine protease activity directed against intact proteins than activity based on peptide substrate assays.

These results demonstrate that the cathepsin G pro-enzyme which accumulates in DPPI-inhibited cells retains partial activity against low molecular weight peptide substrates but is incapable of interacting with protein substrates and inhibitors.

PROPHETIC EXAMPLE 10

PROPOSED ROLE OF DPPI IN POST-TRANSLATIONAL PROCESSING OF MURINE GRANZYME A AND B

The effects of DPPI inhibition on Granzyme A and Granzyme B gene activation and generation of enzymatic activity will be measured to determine if the observed effects of DPPI inhibition were mediated at a post-translational level.

CTL will be generated by culture of NK cell depleted, nylon column nonadherent B6 SpC with irradiated T-cell depleted DBA/2 SpC in the presence or absence of Gly—Phe—$CHN_2$. As an additional control, Z—Phe—Gly—Phe—$CHN_2$ will be added to some cultures. This N-terminal blocked inhibitor is 3 orders of magnitude less reactive with DPPI than Gly—Phe—$CHN_2$. This inhibitor has also been described as possibly having similar non-specific reactivity with thiol groups or other classes of proteases.[60]

At daily intervals, cells will be harvested from culture and assayed for DPPI and BLT esterase activity in granule fractions of cell lysates as previously detailed[4,5] and for granzyme B, using 100 μM BOC—Ala—AspSBzl (obtained by Dr. Martin Poe, Merck Sharp and Dohme Research Laboratories, Rahway, N.J.), as substrates as previously described.[23] Levels of cathepsin B, a lysosomal thiol protease, and macropain, a cytosolic thiol protease,[66] will also be addressed to verify specificity of inhibitory effects mediated by Gly—Phe—$CHN_2$ messenger RNA for granzyme A, granzyme B2 and perforin will be assessed by Northern Blot analysis using cDNA probes provided by Dr. Eckhard Podack, University of Miami, Miami, Fla. (perforin-1 cDNA), Dr. I. Weissman, Stanford, Palo Alto, Calif. (HF/Granzyme A cDNA), and Dr. R. Chris Bleackley, University of Alberta, Alberta, CAN. (CCPI/Granzyme B cDNA) using techniques previously detailed.[68]

If normal levels of granzyme A and granzyme B mRNA are induced in cultures in which DPPI activity is inhibited while levels of granzyme A and granzyme B activity remain low, the accumulation of catalytically inactive granzyme A and granzyme B proenzymes will be assessed. One approach will be to use highly purified DPPI to activate granzyme A and B. In these studies, large numbers of B6 anti-DBA/2 allospecific T-cells will be generated and the granule fraction purified on percoll gradients. Granules will be diluted 10-fold with 10 mM Na acetate, pH 4.0, and chondroitin sulfate associated granzymes precipitated by centrifugation at 4° C., 10,000 g., as previously detailed.[69,70] Pellets will be resuspended in pH 5.0 phosphate buffered saline and incubated with purified DPPI prepared as previously described.[69,70] After varying lengths of coincubation of DPPI and putative granzyme proenzymes, these preparations will be assayed for BLT esterase and granzyme B activity.

Because of the apparent specificity of Gly—Phe—$CHN_2$ for DPPI, the finding that CTL's generated in the presence of Gly—Phe—$CHN_2$ have decreased BLT esterase activity, may be explained in that inhibition of DPPI activity during CTL generation leads to a block in post-translational processing of newly synthesized granzyme A. This is proposed to cause an accumulation of unprocessed, functionally inactive granzyme A proenzyme. Because of the structural similarity of all of the granzyme precursor proteins, this hypothesis would predict similar effects on generation of granzyme B activity. It is anticipated that the above studies will demonstrate normal initial transcription of the genes for both granzyme A and B and the associated granule protein perforin. In addition, while this hypothesis predicts that active, processed granzyme A and B will be absent from CTL granules, regeneration of these activities by addition of exogenous processing enzyme, DPPI may also occur.

As the nature and sequence of post-translational processing and the means whereby granzymes are sorted into cytolytic granules are not yet fully understood, other effects may also be observed. As removal of activation peptides from the N-termini of pancreatic serine proteases leads to major changes in protein folding and final tertiary structure, similar differences in the tertiary structure of precursor and mature granzymes may occur. Such differences may have effects on the intracellular fate and/or half-life of nonprocessed granzymes.

Therefore, if despite normal induction of granzyme mRNA, granzyme activity cannot be generated by addition of exogenous DPPI to granule fractions isolated from CTL generated in the presence of Gly—Phe—$CHN_2$, additional studies will be performed to determine whether such activity can be generated by addition of purified human DPPI to other subcellular fractions. Such experiments may also fail because of unexpected difficulties in reproducing pH and ionic requirements conducive to proper protein folding after DPPI processing of granzyme proenzyme.

As an additional approach to detection of unprocessed granzyme A or granzyme B, these granule proteins will be purified and subjected to N-terminal amino acid sequence analysis. Granule fractions will be prepared as previously detailed and separated from Percoll by disruption in 1.5 M NaCL and ultracentrifugation. The sample will be depleted of perforin by passage of the soluble fraction through a Sephacryl S-300 gel filtration column. Individual granzyme proteins will be further purified by strong cation exchange chromatography (mono S-Column, FPLC).[69] As inactive granzymes are obtained from DPPI inhibited CTL, granzyme preparations isolated from control CTL will first be isolated by this procedure to establish fractions in which these enzymes are expected to appear. Periodic SDS-PAGE analysis of these fractions for presence of proteins of appropriate molecular weight will also be used to aid in isolating granzyme proenzymes.

Following assessment of purity of such fractions by SDS-PAGE, bands of appropriate molecular weight will be submitted for N-terminal amino acid sequence analysis by automated Edman degradation. Granzyme A proenzymes with Glu—Arg and granzyme B proenzymes with Gly—Glu sequences preceding the mature Ile—Ile—Gly—Gly N-terminal residues may in this manner be found according to the above-described procedure.

PROPHETIC EXAMPLE 11

CLONING THE GENE THAT ENCODES HUMAN DPPI

The present example is provided to demonstrate a preferred method for isolating the human dipeptidyl peptidase-I gene. The present example outlines two approaches: (1) use of peptide sequences obtained from fragmented DPPI (human protein) to predict degenerate oligonucleotide probes, and use of the oligonucleotide probe to screen a human cDNA library, selecting positive clones and verifying the sequence; and (2) PCR technique to generate specific cDNA or screen a human cDNA library.

Vectors and Molecular Techniques

Several vectors will be used during the course of these studies. The original cDNA libraries were prepared in lambda gt11. The cDNA's, isolated from either library or prepared by PCR amplification, will be ligated into pGEM3Zf or M13mp18 for the generation of single stranded DNA to be used for sequence analysis or mutagenesis. The pGEM vector contains sequences recognized by T7 and SP6 RNA polymerases and can be used for the synthesis of RNA in vitro. Transfection of Jurkat cells by electroporation[77] will make use of the pSV2neo vector or the pCB6 vector. Eukaryotic cells transfected with either of these vectors can be selected by resistance to the antibiotic G418 due to the presence of the neo gene[78]. An SV40 promoter drives the synthesis of protein from the neo gene. Both vectors carry the pBR322 and SV40 origins of replication for replication in both prokaryotic and eukaryotic cells. These vectors have been used for production of both transient and stable transfected cells. The pCB6 vector uses the CMV promoter to drive the synthesis of the protein from the cloned cDNA inserted into a polylinker site. The vector also contains the human growth hormone termination and polyadenylation signals to insure the synthesis of mature transcripts.

Anti-sense oligonucleotides will be prepared synthetically and added directly to cells in culture as described previously (Bories et al. (1989) Cell, 59:959–968).

Design of Oligonucleotide Probe

Based upon the sequence of the tryptic peptides obtained in Example 1 (see Table 4), the following sequences were chosen for the design of a set of synthetic oligonucleotides:

5'-CC-AAA-GTC-CTG-GGC-ATA-3'

5'-GC-ATC-ATT-CAT-ICC-ICC-ATA-3'

These amino acid sequences were chosen to minimize degeneracy while maximizing length. These probes were synthesized using an Applied Biosystems DNA synthesizer and purified per the manufacturer's recommended protocol. The oligonucleotides were 5' end-labeled with $^{32}P$ before use in screening for the human DPPI gene. The commerical source for $[^{32}P]$-ATP most preferred is ICN or New England Nuclear.

Screening of λgt11 cDNA Libraries

The lambda gt11 cDNA libraries had been prepared from poly(A)$^+$ mRNA obtained from both PHA-stimulated T-cells and peripheral blood monocytes in λgt11 bacteriophage vectors according to the method of Maniatis et al. *Molecular Cloning* (Cold Spring Harbor Laboratory, Cold Spring Harbor, N.Y.) incorporated herein by reference. Plaques were obtained at high density on nitrocellulose filters, and replica filters were prepared for hybridization (Maniatis, supra). To reduce nonspecific background, baked filters were washed overnight in 50 mM Tris-HCl, pH 8/1 mM EDTA/1 M NaCl/0.1% NaDodSO$_4$ at 37° or 42° C., then incubated at 65° C. for 3 hr in 4×SSC (1×SSC=0.15M NaCl/15 mM sodium citrate), 10× Denhardt's solution (1×=0.02% poly-vinylpryrrolidine/0.02% bovine serum ablumin/0.02% Ficoll) (Maniatis, supra) and sonicated and denatured *E. coli* DNA at 1,000 μg/ml.

Replicate filters independently probed with oligonucleotides (designated DP8A and DPPI 12) deduced from human DPPI protein sequences (see FIG. 13A (DP8A) and FIG. 13B (DPPI 12)) were probed with independent oligonucleotides. Hybridization was performed overnight in the latter solution containing $^{32}$P-5'-end-labeled oligonucleotide ($6×10^6$ cpm/pmol at 1 pmol/ml). Filters were washed three times in 4×SSC at the hybridization temperature for 30 minutes per wash, dried at room temperature, and subjected to autoradiography. Positive plaques annealing to both independent probes were picked from the master plate and purified through several rounds of screening on plates prepared at lower placque density.

Only about 1 out 100,000 of the screened cDNA provided a positive clone.

PCR Protocol for Isolating Human DPPI Gene

The PCR technique will be used both to provide a double screen for the positive clones obtained using standard cDNA screening, as well as to do initial synthesis of cDNA's.

The relative position of oligonucleotide probes within the cDNA sequence can be predicted by homology to the rat cDNA. The peptide sequences available from the purified human DPPI match the N-terminal portion of the rat enzyme. Therefore, specific oligonucleotide primers have been made, based on the human enzyme structure. The various primers, and their relation to the rat cDNA, are listed below.

The primers will be used to amplify by PCR the sequence that spans the cDNA encoding the most N-terminal and most C-terminal human peptides. As well as a primer encoding the most N-terminal rat DPPI sequence and an engineered primer in the 3' RACE protocol (Froham, M. A. et al. (1988), Proc. Natl. Acad. Sci. USA, 85:8998–9002). The Frohman et al. (1988) reference is specifically incorporated herein by reference for this purpose. The oligo primers have been made including 5' and 3' restriction enzyme cleavage sites. This will make it possible to insert the amplification product into the multiple cloning site of M13mp18 sequencing vector or the PGEM3ZF vector. The amplified sequence will provide a superior probe for screening the initial lambda gt11 libraries in order to obtain a full length cDNA, if required. The pGEM vector carries sites for initiation of transcription by T7 and SP6 RNA polymerases on opposite sides of the multiple cloning site. Therefore, this vector will be useful for in vitro transcription/translation of cloned sequences as well as for generating template for sequencing.

Once identified and cloned (by either one of the above methods), the cDNA for human DPPI will be separated from the lambda vector by EcoR1 restriction endonuclease digestion and separation on agarose gels or the PCR product will be isolated directly on agarose gels. The isolated cDNA will be characterized by size, restriction endonuclease digestion and then subcloned for sequence analysis. The nucleotide sequence obtained will be analyzed for the presence of a continuous open reading frame and the translation to amino acid sequence. The deduced amino acid sequence will be searched for the presence of the peptide fragments used to design the original oligonucleotide probes as well as other peptide sequences obtained from purified protein. This will directly confirm the appropriateness of the cloning process. This information will also provide a better comparison with the rat DPPI protein and nucleotide sequences and other members of the papain protease family.

The isolated cDNA will be used in the generation of probes for Northern and Southern blot analysis, and subcloned into pGEM3Zf for expression in cell-free expression systems. Based on the size of the isolated protein subunit, a full length cDNA copy of the DPPI transcript would be approximately one kilobase in length, including a portion of the poly-A tail. However, based on the cDNA sequence of rat DPPI and the results of Northern blots of rat tissue mRNA, the DPPI transcript is considerably larger (2.1 kb) than might be expected. The size of the rat cDNA was over 1800 bases[79]. The open reading frame of the rat DPPI cDNA predicted a translation product with a molecular weight of 52,000. The pro-peptide predicted from the cDNA was, in fact, larger than the mature enzyme subunit.

Assessment of the Expression of DPPI in Human Cell Lines

Any sizable (300 base pairs or larger) fragment of the cloned cDNA will be useful for additional Northern Blot analysis and nucleotide sequencing. For the Northern Blot analysis, the cDNA fragment can be used directly as a template for the synthesis of a radiolabeled probe. The Northern blot analysis will demonstrate directly the steady state level of DPPI mRNA in various cell and tissue types. Cell lines that do not express DPPI mRNA or enzymatic activity could be useful for the transfection experiments. Thus, COS-1 cells and the panel of human cells and cell lines detailed in Table 13 will be assessed for DPPI mRNA by Northern blot analysis.

TABLE 13

HUMAN CELLS AND CELL LINES

| | | |
|---|---|---|
| NK (CD16+) | THP-1 | JURKAT |
| U-937 | CD8+T | ENDOTHELIAL |
| PMN | CD4+T | FIBROBLASTS |
| MACROPHAGES | COS-1 | |
| HL-60 | B cells | |

If discrepancies are noted between levels of DPPI enzymatic activity and mRNA levels in any of the cells studied, alternative approaches will be employed to characterize DPPI expression in those cells. Specifically, PCR amplification will be used to detect low levels of DPPI mRNA in cells that express a DPPI-like enzymatic activity. If DPPI mRNA is not detected in these cells, the apparent DPPI activity will be compared to the activity of spleen DPPI by determining subcellular localization, substrate and inhibitor specificity, chromatographic and electrophoretic behavior and antigenic identity.

Preparation of Anti-DPPI Antibodies

Antibodies to human DPPI will be produced in rabbits. Since it is difficult to purify large amounts of DPPI from human spleen, alternate sources of antigenic material are desirable. As cloning and sequence analysis of DPPI cDNA progresses, an alternate strategy for generating DPPI antigen becomes available. The deduced amino acid sequence of human DPPI cDNA will be analyzed for sequences considered suitable for use as a synthetic peptide antigen. The main features considered important for the selection of a peptide sequence for use as an antigen are uniqueness, length (minimum of 10 residues) and hydrophilicity. To date, the peptide sequences obtained from purified human DPPI have been short and predominantly hydrophobic (Table 4). Once identified, the most suitable peptide sequence would be prepared by chemical synthesis and cross-linked to a carrier protein for immunizing rabbits.

PROPHETIC EXAMPLE 12

PREPARATION OF ANTISENSE OLIGONUCLEOTIDES FOR INHIBITION OF EXPRESSION OF DPPI GENE

The present example is provided to describe in detail the method which will be used to prepare antisense oligonucleotides which specifically bind the human dipeptidyl peptidase-I gene, and thereby inhibit human DPPI synthesis.

It is contemplated that the following antisense oligonucleotides specific for fragments of the human DPPI gene may be used in the present invention as primers or probes:

(1) 5'-AC-AAA-GTT-GAT-GCC-ATG-3' (17-mer)

(2) 5'-TT-GAT-ICC-ATG-IAC-ATT-3' (17-mer)

(3) 5'-CC-AAA-GTC-CTG-GGC-ATA-3' (17-mer)

(4) 5'-CC-AAA-ATC-TTG-IGC-ATA-3' (17-mer)

(5) 5'-CC-AAA-GTC-CTG-IGC-ATA-3' (17-mer)

(6) 5'-CC-AAA-ATC-CTG-IGC-ATA-3' (17-mer)

(7) 5'-CC-AAA-GTC-TTG-IGC-ATA-3' (17-mer)

(8) 5'-GC-ATC-ATT-CAT-ICC-ICC-ATA-3' (20-mer)

(9) 5'-TTC-AAA-GGC-AAC-TGC-CAT-GGG-3' (21-mer)

(10) 5'-CTA-CAA-TTT-AGG-AAT-CGG-TAT-GGC-3' (24-mer)

It is contemplated that the sequences may be useful for antisense therapy for the herein described methods and therapeutic agents.

Identification of the Clone Containing DPPI Gene and its Sequencing

Recombinant λ phage DNA will be purified from positive plaques and subjected to restriction mapping. Restriction fragments will be hybridized to the oligonucleotide probe to confirm the initial screening and to localize a restriction fragment for DNA sequence analysis. The DNA sequence will confirm the identity of the clone containing the gene that encodes DPPI. Unique 17–24 base sequences complementary to the coding sequence will be chosen for the construction of antisense oligonucleotides.

Oligonucleotide Synthesis

The oligonucleotides are preferably phosphorothioate-modified to enhance their stability in vivo and their resistance to nuclease degradation, and may be prepared according to the following protocol.

The phosphorothioate-modified oligonucleotides may be obtained commercially, however, methods known to those of skill in the art of oligonucleotide synthesis may also be employed in synthesizing the oligonucleotides described. For example, a 20-mer oligodeoxynucleotide may be synthesized with a phosphorothioate substitution at each base and purified by HPLC.

A general method for preparing oligonucleotides of various lengths and sequences is described by Caracciolo et al. (1989) *Science,* 245:1107 and by Stein and Cohen (1989) In: Oligodeoxynucleotides, Antisense Inhibitors of Gene expression J. S. Cohen, ed CRC Press, Boca Raton, Fla.) which reference is specifically incorporated herein by reference for the purpose.

In general, there are two commonly used solid phase-based approaches to the synthesis of oligonucleotides containing conventional 5'-3' linkages, one involving intermediate phosphoramidites and the other involving intermediate phosphonate linkages. In the phosphoramidite synthesis a suitably protected nucleotide having a cyanoethylphosphoramidate at the position to be coupled is reacted with the free hydroxyl of a growing nucleotide chain derivatized to a solid support. The reaction yields a cyanoethylphosphite, which linkage must be oxidized to the cyanoethylphosphate at each intermediate step, since the reduced form is unstable to acid.

The phosphonate based synthesis is conducted by the reaction of a suitably protected nucleotide containing a phosphonate moiety at a position to be coupled with a solid phase-derivatized nucleotide chain having a free hydroxyl group, in the presence of a suitable activator to obtain a phosphonate diester linkage, which is stable to acid. Thus, the oxidation to the phosphate or thiophosphate can be conducted at any point during synthesis of the oligonucleotide or after synthesis of the oligonucleotide is complete.

The phosphonates can also be converted to phosphoramidate derivatives by reaction with a primary or secondary amine in the presence of carbon tetrachloride. To indicate the two approaches generically, the incoming nucleotide is regarded as having an "activated" phosphite/phosphate group. In addition to employing commonly used solid phase synthesis techniques, oligonucleotides may also be synthesized using solution phase methods such as triester synthesis. These methods are workable, but in general, less sufficient for oligonucleotides of any substantial length.

Each lot of oligonucleotide will be characterized with respect to the completion of synthesis, and will be gel purified. Gel purification is used for purposes of the present invention to remove oligonucleotide strands which do not include the desired nucleotide length. Antisense oligonucleotides having a length of at least 15 nucleotides will be selected for formulation into the therapeutic preparations of the present invention. For example, therapeutic formulations may be prepared according to those methods described in: Antisense Nucleic Acids and Proteins, Fundamentals and Applications, (Joseph Moll and Alexander Van der Krol, editors (1991) Marcel Deckker, Inc), which reference is specifically incorporated herein by references for this purpose.

PROPHETIC EXAMPLE 13

SELECTION OF HUMAN DPPI ANTISENSE OLIGONUCLEOTIDES AS DPPI INHIBITORS

The present example is provided to demonstrate the technique to be used for selecting the most potent antisense oligonucleotides generated in Example 13 for use as DPPI-inhibitor therapeutic agents. Both an in vitro transcription assay and cell culture system to test for growth/maturation inhibitory action of the oligonucleotide will be used to select the most potent antisense oligonucleotides to be used in therapeutic agents as human DPPI inhibitors.

In Vitro Transcription/Translation Assay cDNA inserted in the polylinker site of pGEM rector will be transcribed in vitro with T7 or SP6 polynerose. The RNA will be translated in a reticulocyte extract in the presence or absence of canine pancreatic membranes. The protein product will then be assayed for enzymatic activity and for reactivity with a specific anti-DPPI antibody.

Culture of Myeloid Cells with Antisense Oligonucleotides

Synthetic oligonucleotides will be prepared with sequences that are complementary to the DPPI sense RNA strand as described in Example 12. These antisense oligonucleotides will be taken up by cells and should block the translation of human DPPI mRNA. The sequences of these synthetic antisense oligonucleotides will be determined after the human DPPI cDNA sequence has been analyzed. Since many of the related human cysteine proteases have been cloned and sequenced, the synthetic oligonucleotides will be made so as to minimize cross-hybridization of their mRNAs. As a control for these experiments, cells will be exposed to DPPI "sense" oligonucleotides of equal length. Specifically, short (5- to 35-mer) synthetic oligonucleotide segments will be used to inhibit the synthesis of specific proteins. This strategy has been used in HL-60 cells to inhibit the synthesis of myeloblastin.[59] The uptake and stability of the synthetic oligonucleotides in U-937 cells will be measured by incorporating a radioactive label during synthesis or by end-labeling with 5' polynucleotide kinase. Before incubating the cells with the oligonucleotide, its specificity will be verified by Northern blotting. If required, longer antisense strands will be generated from cloned sequences using the pGEM vector and in vitro transcription.

Additionally, the level of DPPI activity remaining in the antisense treated cells will be determined as a gauge for the effectiveness of the treatment. If DPPI activity is not completely depressed in cells treated with antisense oligonucleotides, high expression antisense transfectants will be prepared to insure that the antisense sequence is in excess over sense transcripts.

PROPHETIC EXAMPLE 14

PROPOSED TREATMENT AND THERAPIES OF MALIGNANCIES OF MYELOID CELL ORIGIN OR IMMUNOLOGICALLY MEDIATED DISEASE WITH hDPPI ANTISENSE OLIGONUCLEOTIDE PREPARATIONS

The present example is provided to define a proposed method by which the described oligonucleotides may be employed in a therapeutic regimen in the treatment of humans with malignancies of myeloid cell origin or immunologically-mediated disease.

Intravascular Administration

The antisense oligonucleotides specific for the inhibition of human DPPI gene expression described in Example 12 may be formulated in an excipient suitable for systemic administration to a human. Such requires that the formulation be prepared at a suitable pH, etc., so as to be pharmacologically acceptable for human administration. By way of example, the most preferred excipient or carrier solution of the formulation is a sterile Ringers solution.

The antisense oligonucleotide formulation may be prepared as described in Example 3 at a concentration of about 10 mg/ml in the liquid sterile carrier solution of choice.

The formulation is to be prepared most preferably in a Ringers solution at a pH and concentration which is pharmacologically acceptable as an intravascular, particularly intravenous, treatment for a human patient. Oligonucleotide preparations for systemic administration which are physiologically compatible may be prepared employing solutions and techniques described in general in Remmingtons Pharmaceutical Sciences (1990),[81] which reference is specifically incorporated herein by reference for the purpose of describing solutions suitable for human administration.

Most preferably, the oligonucleotide preparation should be formulated so as to constitute a concentration of about 10 mg antisense oligonucleotide/ml carrier solution. A most preferred dose of the oligonucleotide formulation for an average human subject having a malignancy of myeloid cell origin or an immunologically mediated disease is between about 50 mg/kg and 100 mg/kg. Thus, an average human male weighing about 70 kg would be treated with an infusion volume of between 50 ml and 100 ml of a 1 mg/ml oligonucleotide preparation of the herein described antisense oligonucleotide.

Within the above described range of treatment doses, the most preferred dose of oligonucleotide formulation to be used is about 75 mg/kg. A most preferred regimen for the treatment of an adult human male having a malignancy of myeloid cell origin or an immunologically mediated disease would therefore constitute about 75 ml of a 10 mg/ml solution of antisense oligonucleotide in a Ringers solution physiologically suitable for administration to a human.

Systemic administration, particularly intravascular, such as intravenous administration, provides a most preferred mode of administering the described antisense oligonucleotide preparations to a patient as they provide for systemic the widespread distribution of the oligonucleotides.

PROPHETIC EXAMPLE 15

PROPOSED ROLE OF DPPI ACTIVITY INHIBITION IN CTL ACTIVATION AND EFFECTOR FUNCTIONS DEPENDENT UPON GRANULE SERINE PROTEASE ACTIVITY

Addition of Gly—Phe—CHN$_2$ to murine mixed lymphocyte cultures has been shown by the present inventors not only to inhibit generation of granzyme A (BLT esterase) activity within the granules of alloactivated T-cells, but also to impair allospecific cytolytic activity of these granzyme deficient effector cells. In parallel with studies detailed in the previous section, the following additional studies will be performed to assess the possibility that such impairment of cytotoxic activity is directly or indirectly related to failure to generate granzyme activity.

In initial studies, B6 anti-H-$2^d$ CTL will be generated in the presence or absence of Gly—Phe—CHN$_2$ or Z—Phe—Gly—Phe—CHN$_2$ as detailed herein. The function of these effector cells will be assessed in cytotoxicity assays designed to detect functions previously ascribed to granzyme effector function. Thus, assessments of CTL induced DNA fragmentation will be made and contrasted to rates of $^{51}$Cr release. In addition, the kinetics of target cell lysis will be assessed to determine whether delays in effector cell recycling occur in granzyme deficient CTL. Therefore, both $^{51}$Cr- and [$^3$H]-thymidine labeled P-815 (H-$2^d$) targets will be employed in assays varying from 1–18 hours in length. Similarly labeled EL4 (H-$2^b$) will be included in some experiments to establish the role of allospecific CTL versus lymphokine activated killer cells. All assays will be performed in the presence or absence of $10^{-5}$ M Gly—Phe—CHN$_2$ to delineate the role of any newly synthesized DPPI in modulating cytolytic activity during longer assay intervals.

The degree of impairment of lytic activity observed in CTL generated in the presence of continuous DPPI inhibition will be further investigated to determine if the culture conditions employed did not generate significant perforin activity, or if DPPI inhibition in some way indirectly impaired generation of perforin lytic activity. To assay perforin or related lytic mechanisms more directly, independent of nuclear degradation, additional 1–4 hour assays will utilize $^{51}$Cr labeled TNP-modified SRBC as targets of cytotoxicity triggered by anti-CD3/anti-TNP heteroconjugated antibodies as previously described.[51]

Where capacity for SRBC lysis is found to be significantly impaired in CTL generated under culture conditions in which levels of perforin mRNA expression are not decreased, additional studies will be performed to determine whether active perforin proteins can be isolated from granules of CTL generated in the presence of DPPI inhibition. Large numbers of allospecific CTL will be generated in the presence or absence of Gly—Phe—CHN$_2$ and after washing the CTL will be disrupted in Ca$^{++}$-free medium and the granules isolated on discontinuous Percoll gradients. Aliquots of the purified granules will then be added to $^5$Cr labeled SRBC suspended in pH 7.2 (10 mM Tris.HCl) buffered 0.15M saline supplemented with 5 mM CaCl$_2$. After 30 minute incubations, samples will be centrifuged and $^{51}$Cr release analyzed.

Where hemolytic activity is not detected in granule fractions of CTL activated in the presence of DPPI inhibition, granules will be extracted by mixing with an equal volume of 1M NH$_4$ acetate, pH 5.0, 1 mM EGTA, 3 mM NaN$_3$, 0.2 μ/ml aprotinin, 0.5 mM PMSF and sonicated as previously described.[31] After centrifugation at 100,000 g and dialysis against pH 7.0 Hepes-buffered saline with 0.1 mM EGTA and 3 mM NaN$_3$, extracted granule proteins will be assayed for hemolytic activity. If deficient hemolytic activity is still noted, aliquots of purified human DPPI or granzyme fractions isolated from control CTL as detailed herein will be added, and the capacity to activate perforin via either processing of inactive perforin precursors or synergistic effects on RBC membrane structures will be assessed.

Additional studies will also be performed to assess whether impairment of DPPI mediated post-translational processing of granzymes leads to accumulation of aberrant protein molecules that alters granule organization in ways that nonspecifically affect transport of other proteins to this intracellular compartment. A major component of the cytoplasmic granules in CTL is chondroitin sulfate proteoglycan.[8] Therefore, the organization of cytoplasmic granules will be assessed by the presence of newly synthesized proteoglycan. Na$_2^{35}$SO$_4$ will be added to control and DPPI inhibited MLC for 24 hours before harvesting CTL and granule fractions isolated as previously detailed. Granule fractions will be assessed for $^{35}$S, and SDS-PAGE analysis will be performed to assess presence of $^{35}$S-labeled 400 KDa proteoglycans.

PROPHETIC EXAMPLE 16

THE ROLE OF DPPI ENRICHED EFFECTOR CELLS AND DPPI ENZYMATIC ACTIVITY IN IN VIVO ALLOIMMUNE RESPONSES

The close association between in vitro or in vivo generation of CTL effector function and the expression of granzyme serine protease activity may relate to the role these enzymes play in the effector functions of these cells. The present example outlines additional studies to assess whether indirect inhibition of granzyme generation by DPPI inhibition has discernible effects on the course of GVHD or skin allograft rejection. In these studies, the course of disease mediated by control or CTL depleted (Leu—Leu—OMe treated) donor cells will be compared to that generated in the presence of continuous DPPI inhibition and putative impaired generation of active granzyme protease activity.

Initial studies will be performed to establish regimens of repetitive subcutaneous Gly—Phe—$CHN_2$ injection or continuous subcutaneous infusion of Gly—Phe—$CHN_2$ by osmotic pumps (Alzet Corp.) that achieve sustained >95% inhibition of in vivo SpC DPPI activity. Once such regimens are established and preliminary studies with CTL activated in the presence or absence of Gly—Phe—$CHN_2$ indicate optimal assay conditions for demonstrating the effects of this inhibitor on cytolytic effector mechanism, studies will be performed to analyze in vivo effects of Gly—Phe—$CHN_2$ on generation of granzyme enzymatic activity and capacity for lysing a nucleated or nucleated target cells. In these studies, 3–5 B6 mice per group will be infused with DPPI inhibitor, Z—Phe—Gly—Phe—$CHN_2$ (control inhibitor) or vehicle control and peritoneal exudate lymphocytes (PEL) will be harvested either 7 days after a primary I.P. injection of Class I + II. $H-2^d$ expressing 70Z/3 cells or on days 3–5 after a secondary I.P. injection with P-815 cells.

In preliminary studies, the present inventors have found that under these conditions $1$–$2 \times 10^7$ cytolytic PEL per animal are routinely obtained. Sufficient cells from each animal will be obtained to perform both multiple lytic assays and to obtain isolated granule fractions for enzymatic assays. As PEL have been reported to be agranular BLT esterase deficient CTL,[43] an additional regimen (Thiele et al. (1988) J. Immunol. 141:3377–3382) described below will be employed to elicit splenic CTL during allogeneic GVHD responses.

Irradiated B6D2F1 mice will be infused by lateral tail vein injection with $30 \times 10^6$ B6 SpC. Recipient spleens will be harvested 5 days later and assayed for allospecific CTL activity and granule BLT esterase and granzyme B activity. It is expected that these studies will demonstrate that inhibition of DPPI activity has effects on in vivo generated CTL lytic activity and granzyme activity similar to those demonstrated for in vitro activated CTL. In addition, these studies will establish Gly—Phe—$CHN_2$ administration regimens for subsequent assessment of effects of this inhibitor on the evolution of GVHD or skin allograft rejection. As in vivo administration of enzyme inhibitors may be associated with upregulation of DPPI mRNA, relatively high inhibitor doses may be required. However, as a single injection of Gly—Phe—$CHN_2$ has been found to induce sustained inhibition of DPPI over 24 hours, this Gly—Phe—$CHN_2$ inhibitor seems to not have an unduly short in vivo half-life, and even if daily doses need to be increased by an order of magnitude or more, such doses would represent several mg per animal per day.

As prior studies in the inventors laboratory have demonstrated a role for Leu—Leu—OMe sensitive cytotoxic effector cells in the generation of lethal GVHD in B6→B6D2F1 mice and in mediating acute rejection of B6D2F1 skin by B6 effector T-cells, these transplant models will be employed in initial studies with DPPI-inhibitors. Leu—Leu—OMe sensitive B6 effector cells have also been shown to play a requisite role in generating destructive lesions of the intralobular bile ducts in Class I MHC disparate B6×bm1 F1 mice or multiple non MHC antigen disparate Balb. B×B6 F1 mice. In additional studies, similar hepatic lesions have been seen in the Class I+II MHC disparate and multiple non-MHC antigen disparate B6→B6D2F1 mice.

In contrast to the GVHD lesions generated in many other organs during GVHD, the periductular lesions generated between 11 and 42 days post-BMT in these mice have been found to be composed of an almost purely lymphocytic inflammatory infiltrate and therefore effects of any of the agents to be tested on DPPI enriched myeloid cells is not likely to affect interpretation of results. Thus, in addition to assessing GVHD induced mortality, the course of hepatic GVHD in B6→B6D2F1 mice will be followed.

Following preliminary studies defining in vivo regimens adequate to provide sustained inhibition of DPPI, studies will be performed in which 3–5 irradiated B6D2F1 will receive in vivo DPPI inhibitors such as Gly—Phe—$CHN_2$ in conjunction with $5 \times 10^6$ B6 BMC and $2 \times 10^7$ B6 SpC. Survival will be compared to that of groups of B6D2F1 recipients of control or Leu—Leu—OMe treated donor cells in which reservoirs containing only vehicle control will be implanted. All animals will be sacrificed 14 days after transplantation. Spleen cells will be assessed for DPPI, cathepsin B, BLT esterase and granzyme B activity, and livers will be sectioned and assessed histologically for degree of periportal inflammatory infiltrates and frequency of destructive bile duct lesions utilizing a scoring system as previously detailed.[54]

As one of the demonstrated activities of granzyme A is the capacity to degrade extracellular matrix proteins, these studies will be of value in evaluating the effects of DPPI inhibition on bile duct epithelial damage postulated to result from cell mediated cytotoxicity, and in assessing the role of granzymes in the migration of effector lymphocytes into tissues.

In additional studies performed in this same strain combination, mortality rates will be followed in the same study groups. Drug reservoirs will be replaced at 2 week intervals. However, as lethal GVHD usually develops within 14–25 days post-transplantation, results will be drawn from 28 day study terms. In these studies, additional animals will be added to each experimental group with plans to sacrifice these animals at weekly intervals for assessment of SpC DPPI, BLT esterase, and cathepsin B activity. Such studies will assess the efficacy and specificity of the DPPI inhibitor regimen employed.

PROPHETIC EXAMPLE 17

EFFECTS OF DPPI INHIBITORS ON GVHD

Depending on the results of Example 16, additional studies will be performed to assess the effects of DPPI inhibitors on GVHD directed at more limited histocompatibility antigen disparity. Thus, if positive benefits of DPPI inhibition are observed, bm12 Class II MHC disparities that have been observed to generate predominately CD4 T helper cell responses will be utilized to determine whether any role for DPPI or granzyme function can be shown in GVHD or allograft rejection mediated by such effector cells. Additional experiments employing non-MHC encoded antigenic disparities will be performed to determine whether effects of DPPI inhibition can be seen in GVHD generated in response to less potent immunologic stimuli.

PROPHETIC EXAMPLE 18

EFFECTS OF DPPI INHIBITORS ON SKIN ALLOGRAFT REJECTION

The effects of DPPI inhibition on B6D2F1 skin allograft rejection by B6 mice will be assessed. Because of the presence of host-derived CTL precursors in adult thymectomized T-cell depleted mice, these studies will be performed in normal B6 recipient mice. Prior to such studies, in vivo regimens for dipeptide methyl ester mediated CTL depletion will be assessed. The benzyl ester derivative of Leu—Leu—OMe has been found by the present inventors to be 5-fold more potent that Leu—Leu—OMe in mediating depletion of NK cells. The inventors' recent studies have also demonstrated that norleucyl-norleucine methyl ester is 2-fold more active that Leu—Leu—OMe. Therefore, these Leu—Leu—OMe animals as well as those given norLeu—norLeu—OBenzyl will be assessed for efficacy of in vivo CTL depletion. The present inventors have found that nor eucaine containing dipeptides are taken up by leukocytes and are substrates for DPPI, and thus are potentially useful in fashioning specific norleucine—norleucine DPPI inhibitos.

Following screening of these agents, studies will be performed in which bolus injections of these agents will be given at various intervals to B6 recipients of B6D2F1 skin grafts. Skin graft survival in these mice will be compared to that of control recipients, recipients of sham reservoir implants and recipients of continuous infusions of Gly—Phe—$CHN_2$. Depending upon the results of initial experiments, additional studies will be performed using skin grafts with Class I MHC only, Class II MHC only or multiple non-MHC encoded antigenic differences, to determine whether putative roles of CTL or CTL generated granule serine proteases play greater or lesser roles in immune responses elicited by these separate classes of alloantigenic differences.

BIBLIOGRAPHY

The following references are specifically incorporated herein by reference in pertinent part for the purposes indicated.

1. Thiele, D. L. and Lipsky, P. E. (1985), *Proc. Natl. Acad. Sci. USA*, 82:2468–2472.
2. Thiele, D. L. and Lipsky, P. E. (1986), *J. Immunol.*, 136:1038–1048.
3. Thiele, D. L., Charley, M. R., Calomeni, J. A., and Lipsky, P. E. (1987), *J. Immunol.*, 138:51–57.
4. Thiele, D. L. and Lipsky, P. E. (1990), *Proc. Natl. Acad. Sci. USA*, 87:83–87.
5. Thiele, D. L. and Lipsky, P. E. (1990), *J. Exp. Med.*, 172:183–194.
6. Rosenberg, A. G., Muzuochi, T., Sharrow, S. O. and Singer, A. (1987), *J. Exp. Med.*, 165:1296–1315.
7. Clark, W. R. (1988), *Immunol. Today*, 9:101–104.
8. Tschopp, J. and Nabholz, M. (1990), *Annu. Rev. Immunol.*, 8:279–302.
9. Golding, H. and Singer, A. (1985), *J. Immunol.*, 135:1610.
10. Mizuochi, T., Golding, H., Rosenberg, A. S., Gilmcher, L. H., Malek, T. R. and Singer, A. (1986), *J. Exp. Med.*, 162:427.
11. Korngold, R. and Sprent, J. (1987), *Transplantation (Baltimore)*, 44:335–339.
12. Lobe, C. G., Havele, C. and Bleackley, R. C. (1986), *Proc. Natl. Acad. Sci. USA*, 83:1448–1452.
13. Gershenfeld, H. K. and Weissman, L. (1986), *Science*, 232:854–858.
14. Brunet, J. F., Dosseto, M., Denizot, F., Mattel, M. G., Clark, W. R., Haqqi, T., Ferrier, M., Nabholz, P., Schmitt, M., Verhulst, A. M., Luciani, M. F. and Goldstein, P. (1986), *Nature*, 322:268–271.
15. Kwon, B. S., Kestler, D., Lee, E., Wakulchik, M. and Young, J. D. E. (1988), *J. Exp. Med.*, 168:1839–1954.
16. Bleackley, R. C., Duggan, B., Ehrman, N. and Lobe, C. G. (1988), *FEBS Lett.*, 234:153–159.
17. Jenne, D., Rey, C., Masson, D., Stanley, K. K., Herz, J., Plaetinck, G. and Tschopp, J. (1988), *J. Immunol.*, 140:318–323.
18. Jenne, D. E., Masson, D., Zimmer, M., Haefliger, J. A., Li, W-H. and Tschoop, J. (1989), *Biochemistry*, 28:7953–7960.
19. Bleackley, R. C., Lobe, C. G., Duggan, B., Ehrman, N., Fregeau, C., Meier, M., Letellier, M., Havele, C., Shaw, J., and Paetkau, V. (1988), *Immunol. Rev.*, 103:5–19.
20. Peters, P. J., Geuze, H. J., van der Donk, H. A. and Borst, J. (1990), *Immunol. Today*, 11:28–32.
21. Peters, P. J., Borst, J., Oorschot, V., Fukuda, M., Krahenbuhl, O., Tschoop, J., Slot, J. W. and Geuze, H. J. (1991), *J. Exp. Med.*, 173:1099–1109.
22. Griffiths, G. M., Namikawa, R., Mueller, C., et al. (1991), *Eur. J. Immunol.*, 21:687–692.
23. Okade, S., Kam, C-M., Narasimhan, L. et al. (1991), *Biochemistry*, 30:2217–2227.
24. Munger, W. E., Berrebi, G. A. and Henkart, P. A. (1988), *Immunol. Rev.*, 103:99–109.
25. Munger, W. E. (1988), Nat. *Immun. Cell Growth Regul.*, 7:61–62.
26. Tschopp, J. and Nabholz, M. (1987), *Ann. Inst. Pasteur Immunol.*, 138:290–295.
27. Simon, M. M., Fruth, Y., Simon, H. G. and Kramer, M. D. (1987), *Ann. Inst. Pasteur Immunol.*, 138:309–314.
28. Bogenberger, J. and Haas, M. (1988), *Oncogene Res.*, 3:301–312.
29. Simon, M. M., Simon, H. G., Fruth, U. et al. (1987), *Immunology*, 60:219–230.
30. Masson, D. and Tschopp, J. (1985), *J. Biol. Chem.*, 260:9069–9072.
31. Liu, C. C., Perussia, B., Cohn, Z. A. and Young, J. D-E. (1986), *J. Exp. Med.*, 164:2061–2076.
32. Podack, E. R., Young, J. D.-E. and Cohn, Z. A. (1985), *Proc. Natl. Acad. Sci. USA*, 82:8629–8633.
33. Zalman, L. S., Martin, D. E., Jung, G. and Mueller-Eberhard, H. J. (1987), *Proc. Natl., Acad., Sci. USA*, 84:2426–2429.
34. Young, J. D.-E., Cohn, Z. A, Podack, E. R. (1986), *Science*, 233:184–190.
35. Blumenthal, R., Millard, P. J., Henkart, M. P., Reynolds, C. W. and Henkart, P. A. (1984), *Proc. Natl. Acad. Sci. USA*, 81:5551–5555.
36. Young, J. D.-E., Hengartner, H., Podack, E. R. and Cohn, Z. A. (1986), *Cell*, 44:849.
37. Young, L. H. Y., Klavinskis, L. S., Oldstone, M. B. A. and Young J. D.-E. (1989), *J. Exp. Med.*, 169:2159–2171.
38. Mueller, C., Kaegi, D., Aebischer, T. et al. (1989), *Eur. J. Immunol.*, 19:1253–1259.

39. Russell, J. H., Masakowski, V. R. and Dobos, C. B. (1980), *J. Immunol.*, 124:1100–1105.
40. Hameed, A., Olsen, K. H., Lee, M.-K. et al. (1989), *J. Exp. Med.*, 169:765–777.
41. Zheng, L. M., Zychlinsky, A., Liu, C.-C., et al. (1991), *J. Cell. Biol.*, 112:279–288.
42. Dennert, G., Anderson, C. G. and Prochazka, G. (1987), *Proc. Natl. Acad. Sci. USA*, 84:5004–5008.
43. Berke, G. and Rosen, D. (1988), *J. Immunol.*, 141:1429–1436.
44. Wyllie, A. H. (1980), *Nature*, 284:555–556.
45. Haas, R. (1989), *J. NIH. Res.*, 1:91–94.
46. Larrick, J. W. and Wright, S. C. (1990), *FASEB J.*, 4:3215–3223.
47. Liu, C.-C., Steffen, M., King, F. and Young, J. D.-E. (1987), *Cell*, 51:393–403.
48. Shi, L., Kraut, R. P. and Greenberg, A. H. (1991), *FASEB J.*, 5:A601.
49. Patel, S. S., Thiele, D. L. and Lipsky, P. E. (1987), *J. Immunol.*, 139:3886–3895.
50. Thiele, D. L. and Lipsky, P. E. (1989), *Immunol. Today*, 10:375–381.
51. Lancki, D. W., Hsleh, C.-S. and Fitch, F. W. (1991), *J. Immunol.*, 146:3242–3249.
52. McDonald, J. K. and Barrett, A. J. (1986),In: Mammalian Proteases: A Glossary and Bibliography Volume 2, Exopeptidases; Academic Press, London, Orlando, San Diego, New York, Austin, Montreal, Sydney, Tokyo, Toronto.
53. Vallera, D. A., Soderling, C. C. B. and Kersey, J. H. (1982), Transplantation, 33:243.
54. Williams, F. H. and Thiele, D. L. (1990), *Hepatology*, 12:911 (Abstract).
55. Rosenberg, A. S., Munitz, T. I., Maniero, T. G. and Singer, A. (1991), *J. Exp. Med.*, 163:1463–1471.
56. Thiele, D. L. and Lipsky, P. E. (1986), *J. Immunol.*, 137:1399–1406.
57. Thiele, D. L. and Lipsky, P. E. (1988), *Clin. Immunol. Immunopathol.*, 49:405–423.
58. Patel, S. S., Duby, A. D., Thiele, D. L. and Lipsky, P. E. (1988), *J. Immunol.*, 141:3726–3736.
59. Thiele, D. L. and Lipsky, P. E. (1991), *FASEB J.*, 5:A973.
60. Green, G. D. J. and Shaw, E. (1981), *J. Biol. Chem.*, 256:1923–1928.
61. Sentman, C. L., Hackett, J., Jr., Kumar, V. and Bennett, M. (1989), *J. Exp. Med.*, 170:191–202.
62. Jenne, D. E. and Tschopp, J. (1988), *Curr. Top. Microbiol. Immunol.*, 140:33–47.
63. Murphy, M. E. P., Moult, J., Bleackley, R. C. et al. (1988), *Proteins: Structure, Functions and Genetics*, 4:190–204.
64. Martin, S. J., Lennon, S. V., Bonham, A. M. and Cotter, T. G. (1990), *J. Immunol.*, 145:1859–1867.
65. Cohen, J. J. and Duke, R. C. (1984), *J. Immunol.*, 132:38–42.
66. McGuire, M. J. and Demartino, G. H. (1986), *Biochem. Biophys. Acta.*, 873:279–289.
67. Lowrey, D. M., Aebischer, T., Olsen, K., Lichten held, M., Rupp, F., Hengartner, H. and Podack, E. R. (1989), *Proc. Natl. Acad. Sci. USA*, 86:247.
68. Minakuchi, R., Wacholtz, M. C., Davis, L. S. and Lipsky, P. E. (1990), *J. Immunol.*, 145:2616–2625.
69. Krahenbuhl, O., Rey, C., Jenne, D. et al. (1988), *J. Immunol.*, 141:3471–3477.
70. Masson, D., Peters, P. J., Geuze, H. J. et al. (1990), *Biochemistry*, 29:11229–11235.
71. McGuire, M. J., Lipsky, P. E. and Thiele, D. L. (1991), *FASEB J.*, 5:A827 (abstract).
72. Geppert, T. D. and Lipsky, P. E. (1988), *J. Clin. Invest.*, 81:1497.
73. Yokota, T., Arai, N., Lee, F. et al. (1985), *Proc. Natl. Acad. Sci. USA*, 82:68–72.
74. Mosmann, T. R., Cherwinski, H., Bond, M. W. et al. (1986), *J. Immunol.*, 136:2348–2357.
75. Widmer, M. B. and Grabstein, K. H. (1987), *Nature*, 326:795–800.
76. Lee, F., Yokota, T., Otsuka, T. et al. (1986), *Proc. Natl. Acad. Sci. USA*, 83:2061–2065.
77. Thiele, D. L. and Lipsky, P. E. (1985), *J. Immunol.*, 134:786–793.
78. Thiele, D. L. and Lipsky, P. E. (1991), *Blood*, 79:964–971.
79. Bouma, J. M. W. and Gruber, M. (1964), *Biochim. Biophys Acta*, 89:545–547.
80. Isumiya, N and Fruton, J. S. (1956), *J. Biol. Chem.*, 218:59–76.
81. Fruton, J. S. and Mycek, M. J. (1956), *Arch. Biochem. Biophys*, 65: 11–20.
82. Voynick, J. M, and Fruton, J. S. (1968), *Biochemistry*, 7:40–44.
83. McDonald, J. K et al. (1969), *J. Biol. Chem.*, 244–2693–2709.
84. McDonald, J. K., Zeitman, B. B. and Ellis, S. (1972), *Biochem. Biophys, Res. Comm.*, 46:62–70.
85. McDonald, J. K., Callahan, P. X. and Ellis, S. (1972), *Meth. Enzymol.*, 25:272–281.
86. Calam, D. H. and Thomas, H. J (1972), *Biochim. Biophys. Acta*, 276:328–332.
87. Thompson, S. A., andrews, P. R. and Hanzlik, R. P. (1986), *J. Med. Chem.*, 29:104–111.
88. Shaw, E. (1990), in *Advances in Enzymology and Related Areas of Molecular Biology*, volume 63 A Meister, ed., J. Wiley Pubb. pp 271–347.
89. Fruton, J. S. et al. (1953), *J. Biol. Chem.*, 204:891–902.
90. C. Cazenave and Claude Helene, (1991) In: *Antisense Nucleic Acids and Proteins, Fundamentals and Applications*, Chapter 3, pg. 47–57, Joseph Mol and Alexander Van der Krol, editors, Marcel De Ker, Inc., New York. Bael. Hong Kong.
91. Wurz H., Tanaka, A. and Fruton, J. S. (1962), *Biochemistry*, 1:19–29.
92. Heinrich, C. P. and Fruton, J. S. (1968), *Biochemistry*, 7:3556–3565.
93. Huang, F. L. and Tappel, A. L. (1972), *Biochim, Biophys, Acta*, 268:527–538.
94. Takayama, H., Treen, G., Humphrey, W., Bluestone, J. A., Henkart, P. A. and Sitkovsky M. V. (1987), *J. Immunol.*, 138:566–569.
95. Lobe, C. G., Finlay, B. B., Paranchych, W., Paetkau, V. H. and Bleackley, R. C. (1986), Science, 232:858–861.
96. Gershenfeld, H. K., Hershberger, R. J., Shows, T. B. and Weissman, I. L., (1988), *Proc. Natl. Acad. Sci. USA*, 85:1184–1188.
97. Henkart, P. A., Berrebi, G. A., Takayama, I. I., Munger, W. E., Sitkosky, M. V. (1987), *J. Immunol.*, 139:2398–2405.
98. Pasternack, M. S., Verret, C. R., Llu, M. A. and Eisen, H. N. (1986), *Nature*, 322–740–743.
99. Young, J. D., Leong, L. G., Liu, C., Damiano, A., Wall, D. A. and Cohn, Z. A. (1986), *Cell*, 47:183–194.
100. Garcia-Sanz, J. A., MacDonald, H. R., Jenne, D. E., Tschopp, J. and Nabholz, M. (1990), *J. Immunol.*, 145:3111–3118.
101. Hameed, A., Lowrey, D. M., Lichtenheld, M., Podack, E. R. (1988), *J. Immunol.*, 141:3142–3147.

102. Redmond, M. J., Letellier, M., Parker, J. M. R., Lobe, C., Havele, C., Paetkau, V., Bleackley R. C. (1987), *J. Immunol.*, 139–3184–3188.
103. Schmid, J., Weissmann, C. (1987), *J. Immunol.*, 139:250–256.
104. Masson, D., Tschoop, J., (1987), *Cell*, 49:679–685.
105. Jenne, D., Tschopp, J. (1988), *Immunol. Rev.*, 103:53–71.
106. Jenne, D., Rey, C., Haefliger, J., Qiao, B., Groscurth, P., Tschopp, J. (1988), *Immunology*, 85:4814–4818.
107. Janoff, A. (1973), *Lab. Invest.*, 20:458–464.
108. Takahashi, H., Nukiwa, T., Yoshimura, K., Quick, C. D., States, D. J., Holmes, M. D., Whang-Peng, J., Knutsen, T., Crystal R. G. (1988), *J. Biol. Chem.*, 263:14739–14747.
109. Sinha, S., Watorek, W., Karr, S., Giles, J., Bobe, W., Travis, J. (1987), *Proc. Natl. Acad. Sci.*, 84:2228–2232.
110. Farley, D., Salvensen, G., Travis, J. (1988), *Biol. Chem. Hoppe-Seyler*, 369:Suppl.3–7.
111. Senior, R. M., Campbell, E. J. (1984), *J. Immunol.*, 132:2547–2551.
112. Salvensen, G., Farley, D., Shuman, JH., Przybyla, A., Reilly, C., Travis, J. (1987), *Biochemistry*, 26:2289–2293.
113. Kraut, J. (1977), *Ann. Rev. Biochem.*, 46:331–358.
114. Stroud, R. M., Kossiakoff, A. A., Chambers, J. L. (1977), *Ann. Rev. Bioeng.*, 6:177–193.
115. Shotton, D. M., Harley, B. S. (1970), *Nature*, 225:802–806.
116. Emi, M., Nakamura, Y., Ogawa, M., Tamamoto, T., Nishide, T., Mori, T., Matsubara, K. (1986), *Gene*, 41:305–310.
117. Fletcher, T. S., Shen, W., Largman, C. (1987), *Biochemistry*, 26:7256–7261.
118. Kaul, R. K., Hildebrand, B., Roberts, S., Jagadeeswaran, P. (1986), *Gene*, 41:311–314.
119. Salvesen, G. and Enghild J. J. (1990), *Biochemistry*, 29:5304–5308.
120. Okano, K., Aoki, Y., Shimizu, H. and Naruto, M. (1990), *Biochem. Biophys. Res. Comm.*, 167:1326–1332.
121. Ishidoh, K., Muno, D., Sato, N. and Kominami, E., (1991), *J. Biol. Chem.*, 266:16312–16317.
122. Angliker, H., Wikstrom, P., Kirschke, H. and Shaw, E. (1989), *Biochem. J.*, 262:63–68.
123. Bories, D., Raynal, M. D., Solomon, D. H., Darzynkiewiez, Z. and Cayre, Y. E. (1989), *Cell*, 59:959–968.
124. Lathe, R. (1985), *J. Mol. Biol.*, 183:1–12.
125. Sambrook, J., Fritsch, E. F., Maniatis, T. (1989) *Molecular cloning a laboratory manual*, 2nd Ed., Chapter 11.
126. Murphy, E. P., Moult, J., Bleackley, R. C., Gershenfeld, H., Weissman, I. L. and James, M. N. G. (1988), Proteins: Structure, Function and Genetics 4:190–204.
127. Nolle, B., Specks, U., Ludemann, J., Rohrbach M. S., DeRemee, R. A. and Gross, W. L. (1989), *Ann. Int. Med.*, 111:28–40.
128. Niles, J. L., McCluskey, R. T., Ahmad, M. F. and Arnarout, M. A. (1989), *Blood*, 74:1888–1893.
129. Ludemann, J., Utecht, B. and Gross W. L. (1990), *J. Exp. Med.*, 171:357–362.
130. Jenne, D. E., Tschopp, J., Ludemann, J., Utecht, B. and Gross, W. L. (1990), *Nature*, 346:520.
131. Senior, R. M., Campbell, E. J., Landis, J. A., Cox, F. R., Kuhn, C. and Koren, H. S. (1982), *J. Clin. Invest.* 69:384–393.
132. Fischer, D. G., Pike, M. C., Koren, H. S. and Snyderman, R. S. (1980), *J. Immunol.*, 125:463–465.
133. Osserman, E. F. and Lawlor, D. P. (1966), *J. Exp. Med.*, 124:921–955.
134. Campbell, E. J., Cury, J. D., Shapiro, S. D., Goldberg, G. I. and Welgus, H. G. (1991), *J. Immunol.*, 146:1286–1293.
135. Maison, C. M., Villiers, C. L. and Colomb, M. G. (1991), *J. Immunol.* 147:921–926.
136. Kao, R. C., Wehner, N. G., Skubitz, K. M., Gray, B. H. and Hoidal, J. R. (1988), *J. Clin. Invest.*, 82:1963–1973.
137. Wilde, C. G., Snable, J. L., Griffith, J. E. and Scott, R. W. (1990), *J. Biol. Chem.*, 265: 2038–2041.
138. Rao, N. V., Wehner, N. G., Marshall, B. C., Gray, W. R., Gray, B. H. and Hoidal, J. R. (1991), *J. Biol. Chem.*, 266:9540–9548.
139. Sambrook, J., Fritsch, E. F., Maniatis, T. (1989), *Molecular cloning a laboratory manual*, 2nd Ed., Chapter 16.
140. Planta, R. J., Gruber, M. (1963), *Anal. Biochem.*, 5:360–367.
141. Bury, A. F., Pennington, R. J. (1975), *J. Biochem.*, 145:413–416.
142. Jadot, M. et al. (1984), *J. Biochem.*, 219:965–970.
143. Gur, H., El-Zaatarl, F., Geppert, T. D., Wacholtz, M. C., Taurog, J. D., Lipsky, P. E. (1990), *J. Exp. Med.*, 172:1267–1270.
144. Southern, P. J. and Berg, P. (1982), *J. Mol. Appl. Genet.*, 1:327–341.
145. Remmingtons Pharmaceutical Sciences (1990) 18th Edition

---

What is claimed is:

1. A method for treating organ allograft rejection or graft-versus-host disease in a mammal comprising administering to said mammal an effective amount of a compound having the following structure:

$$H_2N-CH(R^1)-CO-NH-CH(R^2)-CO-X$$

wherein $R^1$ is H, $-CH_2OH$, $-CH(CH_3)_2$, $-CH_2CH(CH_3)_2$, or a $C_1-C_6$ alkyl group;

$R^2$ is benzyl, $-CH_2$-(para-hydroxyphenyl), or a $C_1-C_6$ alkyl group;

X is $-CHN_2$ or $-CH_2S^+(CH_3)_2$.

2. The method of claim 1 wherein the compound is selected from the group consisting of Gly—Phe—$CH_2S^+(CH_3)_2$, Ser—Leu—$CHN_2$, Ser—Tyr—$CHN_2$, Norleucyl—Norleucyl—$CHN_2$, Val—Phe—$CHN_2$, Ser—Leu—$CH_2S^+(CH_3)_2$, Gly—Leu—$CHN_2$, and Gly—Phe—$CHN_2$.

3. The method of claim 1 wherein the organ allograft rejection is a skin graft rejection, a kidney transplant rejection or a heart transplant rejection.

4. The method of claim 1 wherein the effective amount is between 3 mg/kg and 30 mg/kg.

5. The method of claim 1 wherein the effective amount is between 10 mg/kg and 100 mg/kg.

6. The method of claim 1 wherein the compound is Gly—Phe—$CHN_2$.

7. The method of claim 1 wherein said mammal is a human.

* * * * *

SEQUENCE LISTING ( 1 ) GENERAL INFORMATION:

( i i i ) NUMBER OF SEQUENCES: 38

( 2 ) INFORMATION FOR SEQ ID NO: 1:

( i ) SEQUENCE CHARACTERISTICS:
( A ) LENGTH: 233 amino acid residues
( B ) TYPE: amino acid
( D ) TOPOLOGY: linear ( x i ) SEQUENCE DESCRIPTION: SEQ ID NO: 1:

Leu Pro Glu Ser Trp Asp Trp Arg Asn Val Arg Gly Ile Asn Phe

```
          1                   5                      10                         15
    Val  Ser  Pro  Val  Arg  Asn  Gln  Glu  Ser  Cys  Ser  Gly  Cys  Tyr  Ser
                         20                      25                         30

Phe  Ala  Ser  Leu  Gly  Met  Leu  Glu  Ala  Arg  Ile  Arg  Ile  Leu  Thr
                         35                      40                         45

Asn  Asn  Ser  Gln  Thr  Pro  Ile  Leu  Ser  Pro  Gln  Glu  Val  Val  Ser
                         50                      55                         60

Cys  Ser  Pro  Tyr  Ala  Gln  Gly  Cys  Asp  Gly  Gly  Phe  Pro  Tyr  Leu
                         65                      70                         75

Ile  Ala  Gly  Lys  Tyr  Ala  Gln  Asp  Phe  Gly  Val  Val  Glu  Glu  Asn
                         80                      85                         90

Cys  Phe  Pro  Tyr  Thr  Ala  Thr  Asp  Ala  Pro  Cys  Lys  Pro  Lys  Glu
                         95                     100                        105

Asn  Cys  Leu  Arg  Tyr  Tyr  Ser  Ser  Glu  Tyr  Tyr  Val  Gly  Gly
                        110                     115                        120

Phe  Tyr  Gly  Gly  Cys  Asn  Glu  Ala  Leu  Met  Lys  Leu  Glu  Leu  Val
                        125                     130                        135

Lys  His  Gly  Pro  Met  Ala  Val  Ala  Phe  Glu  Val  His  Asp  Asp  Phe
                        140                     145                        150

Leu  His  Tyr  His  Ser  Gly  Ile  Tyr  His  His  Thr  Gly  Leu  Ser  Asp
                        155                     160                        165

Pro  Phe  Asn  Pro  Phe  Glu  Leu  Thr  Asn  His  Ala  Val  Leu  Ile  Val
                        170                     175                        180

Gly  Tyr  Gly  Lys  Asp  Pro  Val  Thr  Gly  Leu  Asp  Tyr  Trp  Ile  Val
                        185                     190                        195

Lys  Asn  Ser  Trp  Gly  Ser  Gln  Trp  Gly  Glu  Ser  Gly  Tyr  Phe  Arg
                        200                     205                        210

Leu  Arg  Arg  Gly  Thr  Asp  Glu  Cys  Ala  Ile  Glu  Ser  Ile  Ala  Met
                        215                     220                        225

Ala  Ala  Ile  Pro  Ile  Pro  Lys  Leu
                        230
```

( 2 ) INFORMATION FOR SEQ ID NO: 2:

( i ) SEQUENCE CHARACTERISTICS:
        ( A ) LENGTH: 61 amino acid residues
        ( B ) TYPE: amino acid
        ( D ) TOPOLOGY: linear ( x i ) SEQUENCE DESCRIPTION: SEQ ID NO: 2:

```
    Xaa  Leu  Pro  Thr  Ser  Xaa  Asp  Val  Arg  Asn  Val  His  Gly  Ile  Asn
    - 1    1                   5                      10

Phe  Val  Ser  Pro  Val  Arg  Asn  Gln  Ala  Ser  Cys  Gly  Ser  Cys  Tyr
     15                      20                      25

Ser  Phe  Ala  Ser  Met  Gly  Met  Leu  Glu  Ala  Arg  Ile  Arg  Ile  Leu
     30                      35                      40

Thr  Xaa  Asn  Ser  Gln  Thr  Pro  Ile  Leu  Ser  Pro  Gln  Glu  Val  Val
     45                      50                      55

Ser
     60
```

( 2 ) INFORMATION FOR SEQ ID NO: 3:

( i ) SEQUENCE CHARACTERISTICS:
        ( A ) LENGTH: 19 amino acid residues
        ( B ) TYPE: amino acid
        ( D ) TOPOLOGY: linear ( x i ) SEQUENCE DESCRIPTION: SEQ ID NO: 3:

Tyr Ala Gln Asp Phe Gly Leu Val Glu Glu Ala Ser Phe Pro Tyr
 1               5                  10                  15

Thr Xaa Xaa Asp ( 2 ) INFORMATION FOR SEQ ID NO: 4:

( i ) SEQUENCE CHARACTERISTICS:
        ( A ) LENGTH: 44 amino acid residues
        ( B ) TYPE: amino acid
        ( D ) TOPOLOGY: linear ( x i ) SEQUENCE DESCRIPTION: SEQ ID NO: 4:

Tyr Tyr Ser Ser Glu Tyr His Tyr Val Gly Gly Phe Tyr Gly Gly
 1               5                  10                  15

Met Asn Glu Ala Leu Met Lys Leu Glu Leu Val Arg His Gly Pro
                20                  25                  30

Met Ala Val Ala Phe Glu Tyr Val Tyr Asp Phe Leu His Tyr
                35                  40

( 2 ) INFORMATION FOR SEQ ID NO: 5:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 5:

GGCCACGCGT CGACTAGTAC TTTTTTTTTT TTTTTTT         37

( 2 ) INFORMATION FOR SEQ ID NO: 6:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 6:

CUACUACUAC UAGGCCACGC GTCGACTAGT AC         32

( 2 ) INFORMATION FOR SEQ ID NO: 7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 7:

GCATCATTCA TNCCNCCATA         20

( 2 ) INFORMATION FOR SEQ ID NO: 8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 8:

CCAAAGTCCT GGGCATA         17

( 2 ) INFORMATION FOR SEQ ID NO: 9:

( i ) SEQUENCE CHARACTERISTICS:
    ( A ) LENGTH: 6 amino acid residues
    ( B ) TYPE: amino acid
    ( D ) TOPOLOGY: linear ( x i ) SEQUENCE DESCRIPTION: SEQ ID NO: 9:

```
Glu  Lys  Ile  Ile  Gly  Gly
 -1    1
```

( 2 ) INFORMATION FOR SEQ ID NO: 10:

( i ) SEQUENCE CHARACTERISTICS:
    ( A ) LENGTH: 6 amino acid residues
    ( B ) TYPE: amino acid
    ( D ) TOPOLOGY: linear ( x i ) SEQUENCE DESCRIPTION: SEQ ID NO: 10:

```
Gly  Glu  Ile  Ile  Gly  Gly
 -1    1
```

( 2 ) INFORMATION FOR SEQ ID NO: 11:

( i ) SEQUENCE CHARACTERISTICS:
    ( A ) LENGTH: 6 amino acid residues
    ( B ) TYPE: amino acid
    ( D ) TOPOLOGY: linear ( x i ) SEQUENCE DESCRIPTION: SEQ ID NO: 11:

```
Ser  Glu  Ile  Val  Gly  Gly
 -1    1
```

( 2 ) INFORMATION FOR SEQ ID NO: 12:

( i ) SEQUENCE CHARACTERISTICS:
    ( A ) LENGTH: 6 amino acid residues
    ( B ) TYPE: amino acid
    ( D ) TOPOLOGY: linear ( x i ) SEQUENCE DESCRIPTION: SEQ ID NO: 12:

```
Ala  Glu  Ile  Val  Gly  Gly
 -1    1
```

( 2 ) INFORMATION FOR SEQ ID NO: 13:

( i ) SEQUENCE CHARACTERISTICS:
    ( A ) LENGTH: 6 amino acid residues
    ( B ) TYPE: amino acid
    ( D ) TOPOLOGY: linear ( x i ) SEQUENCE DESCRIPTION: SEQ ID NO: 13:

```
Glu  Arg  Ile  Ile  Gly  Gly
 -1    1
```

( 2 ) INFORMATION FOR SEQ ID NO: 14:

( i ) SEQUENCE CHARACTERISTICS:
    ( A ) LENGTH: 6 amino acid residues
    ( B ) TYPE: amino acid
    ( D ) TOPOLOGY: linear ( x i ) SEQUENCE DESCRIPTION: SEQ ID NO: 14:

```
Glu  Glu  Ile  Ile  Gly  Gly
 -1    1
```

( 2 ) INFORMATION FOR SEQ ID NO: 15:

( i ) SEQUENCE CHARACTERISTICS:

(A) LENGTH: 6 amino acid residues
(B) TYPE: amino acid
(D) TOPOLOGY: linear (xi) SEQUENCE DESCRIPTION: SEQ ID NO: 15:

```
Glu Glu Ile Val Gly Gly
 -1           1
```

(2) INFORMATION FOR SEQ ID NO: 16:

(i) SEQUENCE CHARACTERISTICS:
(A) LENGTH: 10 amino acid residues
(B) TYPE: amino acid
(D) TOPOLOGY: linear (xi) SEQUENCE DESCRIPTION: SEQ ID NO: 16:

```
Gly Ala Glu Ala Gly Glu Ile Ile Gly Gly
 -5                   -1           1
```

(2) INFORMATION FOR SEQ ID NO: 17:

(i) SEQUENCE CHARACTERISTICS:
(A) LENGTH: 10 amino acid residues
(B) TYPE: amino acid
(D) TOPOLOGY: linear (xi) SEQUENCE DESCRIPTION: SEQ ID NO: 17:

```
Thr Ala Leu Ala Ser Glu Ile Val Gly Gly
 -5                   -1           1
```

(2) INFORMATION FOR SEQ ID NO: 18:

(i) SEQUENCE CHARACTERISTICS:
(A) LENGTH: 10 amino acid residues
(B) TYPE: amino acid
(D) TOPOLOGY: linear (xi) SEQUENCE DESCRIPTION: SEQ ID NO: 18:

```
Ala Ala Arg Ala Ala Glu Ile Val Gly Gly
 -5                   -1           1
```

(2) INFORMATION FOR SEQ ID NO: 19:

(i) SEQUENCE CHARACTERISTICS:
(A) LENGTH: 10 amino acid residues
(B) TYPE: amino acid
(D) TOPOLOGY: linear (xi) SEQUENCE DESCRIPTION: SEQ ID NO: 19:

```
Glu Asp Val Cys Glu Lys Ile Ile Gly Gly
 -5                   -1           1
```

(2) INFORMATION FOR SEQ ID NO: 20:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 20:

```
ACAAAGTTGA TGCCATG                                                        17
```

(2) INFORMATION FOR SEQ ID NO: 21:

(i) SEQUENCE CHARACTERISTICS:
(A) LENGTH: 17 base pairs
(B) TYPE: nucleic acid ( C ) STRANDEDNESS: single
            ( D ) TOPOLOGY: linear ( x i ) SEQUENCE DESCRIPTION: SEQ ID NO: 21:

TTGATTCCAT GNACATT                                                          1 7

( 2 ) INFORMATION FOR SEQ ID NO: 22:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 22:

CCAAAATCTT GNGCATA                                                          1 7

( 2 ) INFORMATION FOR SEQ ID NO: 23:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 23:

CCAAAGTCCT GNGCATA                                                          1 7

( 2 ) INFORMATION FOR SEQ ID NO: 24:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 24:

CCAAAATCCT GNGCATA                                                          1 7

( 2 ) INFORMATION FOR SEQ ID NO: 25:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 25:

CCAAAGTCTT GNGCATA                                                          1 7

( 2 ) INFORMATION FOR SEQ ID NO: 26:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 26:

TTCAAAGGCA ACTGCCATGG G                                                     2 1

( 2 ) INFORMATION FOR SEQ ID NO: 27:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 27:

CTACAATTTA GGAATCGGTA TGGC  24

( 2 ) INFORMATION FOR SEQ ID NO: 28:

( i ) SEQUENCE CHARACTERISTICS:
        ( A ) LENGTH: 4 amino acid residues
        ( B ) TYPE: amino acid
        ( D ) TOPOLOGY: linear ( x i ) SEQUENCE DESCRIPTION: SEQ ID NO: 28:

Ala Ala Pro Phe
1

( 2 ) INFORMATION FOR SEQ ID NO: 29:

( i ) SEQUENCE CHARACTERISTICS:
        ( A ) LENGTH: 9 amino acid residues
        ( B ) TYPE: amino acid
        ( D ) TOPOLOGY: linear ( x i ) SEQUENCE DESCRIPTION: SEQ ID NO: 29:

Xaa Leu Pro Thr Ser Xaa Asp Val Arg
-1   1               5

( 2 ) INFORMATION FOR SEQ ID NO: 30:

( i ) SEQUENCE CHARACTERISTICS:
        ( A ) LENGTH: 12 amino acid residues
        ( B ) TYPE: amino acid
        ( D ) TOPOLOGY: linear ( x i ) SEQUENCE DESCRIPTION: SEQ ID NO: 30:

Asn Val His Gly Ile Asn Phe Val Ser Pro Val Arg
1               5                   10

( 2 ) INFORMATION FOR SEQ ID NO: 31:

( i ) SEQUENCE CHARACTERISTICS:
        ( A ) LENGTH: 20 amino acid residues
        ( B ) TYPE: amino acid
        ( D ) TOPOLOGY: linear ( x i ) SEQUENCE DESCRIPTION: SEQ ID NO: 31:

Asn Gln Ala Ser Cys Gly Ser Cys Tyr Ser Phe Ala Ser Met Gly
1               5                   10                  15
Met Leu Glu Ala Arg
                20

( 2 ) INFORMATION FOR SEQ ID NO: 32:

( i ) SEQUENCE CHARACTERISTICS:
        ( A ) LENGTH: 20 amino acid residues
        ( B ) TYPE: amino acid
        ( D ) TOPOLOGY: linear ( x i ) SEQUENCE DESCRIPTION: SEQ ID NO: 32:

Ile Arg Ile Leu Thr Xaa Asn Ser Gln Thr Pro Ile Leu Ser Pro
1               5                   10                  15
Gln Glu Val Val Ser
                20

( 2 ) INFORMATION FOR SEQ ID NO: 33:

( i ) SEQUENCE CHARACTERISTICS:

```
            ( A ) LENGTH: 22 amino acid residues
            ( B ) TYPE: amino acid
            ( D ) TOPOLOGY: linear ( x i ) SEQUENCE DESCRIPTION: SEQ ID NO: 33:

Tyr  Tyr  Ser  Ser  Glu  Tyr  His  Tyr  Val  Gly  Gly  Phe  Tyr  Gly  Gly
 1               5                         10                         15

Met  Asn  Glu  Ala  Leu  Met  Lys
                20
```

( 2 ) INFORMATION FOR SEQ ID NO: 34:

```
    ( i ) SEQUENCE CHARACTERISTICS:
            ( A ) LENGTH: 18 amino acid residues
            ( B ) TYPE: amino acid
            ( D ) TOPOLOGY: linear ( x i ) SEQUENCE DESCRIPTION: SEQ ID NO: 34:

Leu  Glu  Leu  Val  Arg  His  Gly  Pro  Met  Ala  Val  Ala  Phe  Glu  Tyr
 1               5                         10                         15

Val  Tyr  Asp
```

( 2 ) INFORMATION FOR SEQ ID NO: 35:

```
    ( i ) SEQUENCE CHARACTERISTICS:
            ( A ) LENGTH: 8 amino acid residues
            ( B ) TYPE: amino acid
            ( D ) TOPOLOGY: linear ( x i ) SEQUENCE DESCRIPTION: SEQ ID NO: 35:

Gly  Met  Leu  Glu  Ala  Arg  Ile  Arg
 1                5
```

( 2 ) INFORMATION FOR SEQ ID NO: 36:

```
    ( i ) SEQUENCE CHARACTERISTICS:
            ( A ) LENGTH: 13 amino acid residues
            ( B ) TYPE: amino acid
            ( D ) TOPOLOGY: linear ( x i ) SEQUENCE DESCRIPTION: SEQ ID NO: 36:

Ala  Val  Ala  Phe  Glu  Tyr  Val  Tyr  Asp  Phe  Leu  His  Tyr
 1                5                         10
```

( 2 ) INFORMATION FOR SEQ ID NO: 37:

```
    ( i ) SEQUENCE CHARACTERISTICS:
            ( A ) LENGTH: 4 amino acid residues
            ( B ) TYPE: amino acid
            ( D ) TOPOLOGY: linear ( x i ) SEQUENCE DESCRIPTION: SEQ ID NO: 37:

Ala  Ala  Val  Ala
 1
```

( 2 ) INFORMATION FOR SEQ ID NO: 38:

```
    ( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 38:

TTGATNCCAT GNACATT                                                    17
```